(12) United States Patent
Bhat et al.

(10) Patent No.: US 9,198,866 B2
(45) Date of Patent: *Dec. 1, 2015

(54) PHARMACEUTICAL FORMULATIONS OF A SUBSTITUTED DIAMINOPURINE

(71) Applicant: Signal Pharmaceuticals, LLC, San Diego, CA (US)

(72) Inventors: Sreenivas S. Bhat, Kendall Park, NJ (US); Xiaozhong Liang, Edison, NJ (US); Anthony Tutino, New Providence, NJ (US); Anthony Joseph Frank, Easton, PA (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/074,765

(22) Filed: Nov. 8, 2013

(65) Prior Publication Data

US 2014/0093566 A1    Apr. 3, 2014

Related U.S. Application Data

(63) Continuation of application No. 13/277,615, filed on Oct. 20, 2011, now Pat. No. 8,603,527.

(60) Provisional application No. 61/406,292, filed on Oct. 25, 2010, provisional application No. 61/481,378, filed on May 2, 2011, provisional application No. 61/528,427, filed on Aug. 29, 2011, provisional application No. 61/537,963, filed on Sep. 22, 2011.

(51) Int. Cl.
| | |
|---|---|
| *A61K 9/28* | (2006.01) |
| *A61K 9/20* | (2006.01) |
| *A61K 9/48* | (2006.01) |
| *A61K 31/505* | (2006.01) |
| *A61K 31/52* | (2006.01) |

(52) U.S. Cl.
CPC ............ *A61K 9/2866* (2013.01); *A61K 9/2018* (2013.01); *A61K 9/2054* (2013.01); *A61K 9/2059* (2013.01); *A61K 9/485* (2013.01); *A61K 9/4866* (2013.01); *A61K 31/505* (2013.01); *A61K 31/52* (2013.01)

(58) Field of Classification Search
None
See application file for complete search history.

(56) References Cited

U.S. PATENT DOCUMENTS

| | | | |
|---|---|---|---|
| 5,858,968 A | 1/1999 | Weiner et al. | |
| 7,521,446 B2 | 4/2009 | Albers et al. | |
| 7,723,340 B2 | 5/2010 | Albers et al. | |
| 7,759,342 B2 | 7/2010 | Bennett et al. | |
| 8,603,527 B2 * | 12/2013 | Bhat et al. | 424/474 |
| 2009/0048275 A1 | 2/2009 | Beauchamps et al. | |
| 2009/0275564 A1 | 11/2009 | Albers et al. | |
| 2009/0312320 A1 | 12/2009 | Albers et al. | |
| 2010/0249066 A1 | 9/2010 | Bennett et al. | |
| 2011/0293716 A1 | 12/2011 | Fernandez De Gatta Garcia et al. | |
| 2012/0129807 A1 | 5/2012 | Bennett et al. | |

FOREIGN PATENT DOCUMENTS

| | | |
|---|---|---|
| WO | WO 99/15155 A1 | 4/1999 |
| WO | WO 2006/076595 A1 | 7/2006 |
| WO | WO 2007/062338 A2 | 5/2007 |
| WO | WO 2007/127382 A1 | 11/2007 |
| WO | WO 2008/057252 A2 | 5/2008 |
| WO | WO 2011/071491 A1 | 6/2011 |

OTHER PUBLICATIONS

Aljaberi et al., 2009, "Functional performance of silicified microcrystalline cellulose versus microcrystalline cellulose: a case study," Drug Development and Industrial Pharmacy 35(9): 1066-1071.

Tobyn et al., 1998, "Physiochemical comparison between microcrystalline cellulose and silicified microcrystalline cellulose," International Journal of Pharmaceutics 169(2):183-194.

Edge et al., 1999, Polysaccharide applications: Cosmetic and Pharmaceutics, 1999, pp. 98-112, chapter 7.

* cited by examiner

*Primary Examiner* — Hasan Ahmed
(74) *Attorney, Agent, or Firm* — Jones Day

(57) ABSTRACT

Provided herein are pharmaceutical formulations, comprising 4-((9-((3S)-tetrahydro-3-furanyl)-8-((2,4,6-trifluorophenyl)amino)-9H-purin-2-yl)amino)-trans-cyclohexanol, including pharmaceutically acceptable salts, solvates, isomers, isotopologues, tautomers and racemic mixtures thereof, and a pharmaceutically acceptable excipient; and their use for treating or preventing disease.

18 Claims, 17 Drawing Sheets

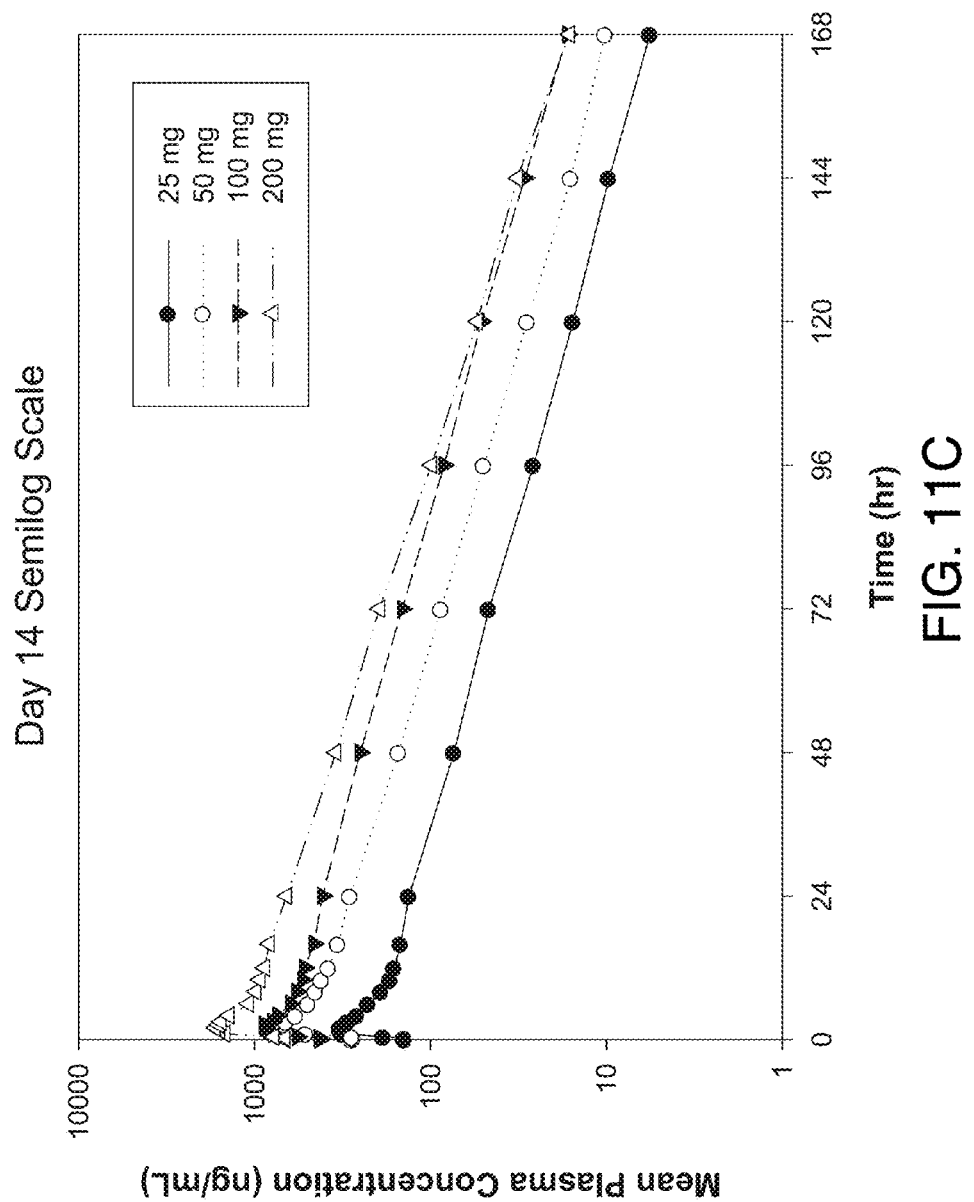

PHARMACEUTICAL FORMULATIONS OF A SUBSTITUTED DIAMINOPURINE

1. CROSS-REFERENCE TO RELATED APPLICATIONS

Figure 1:
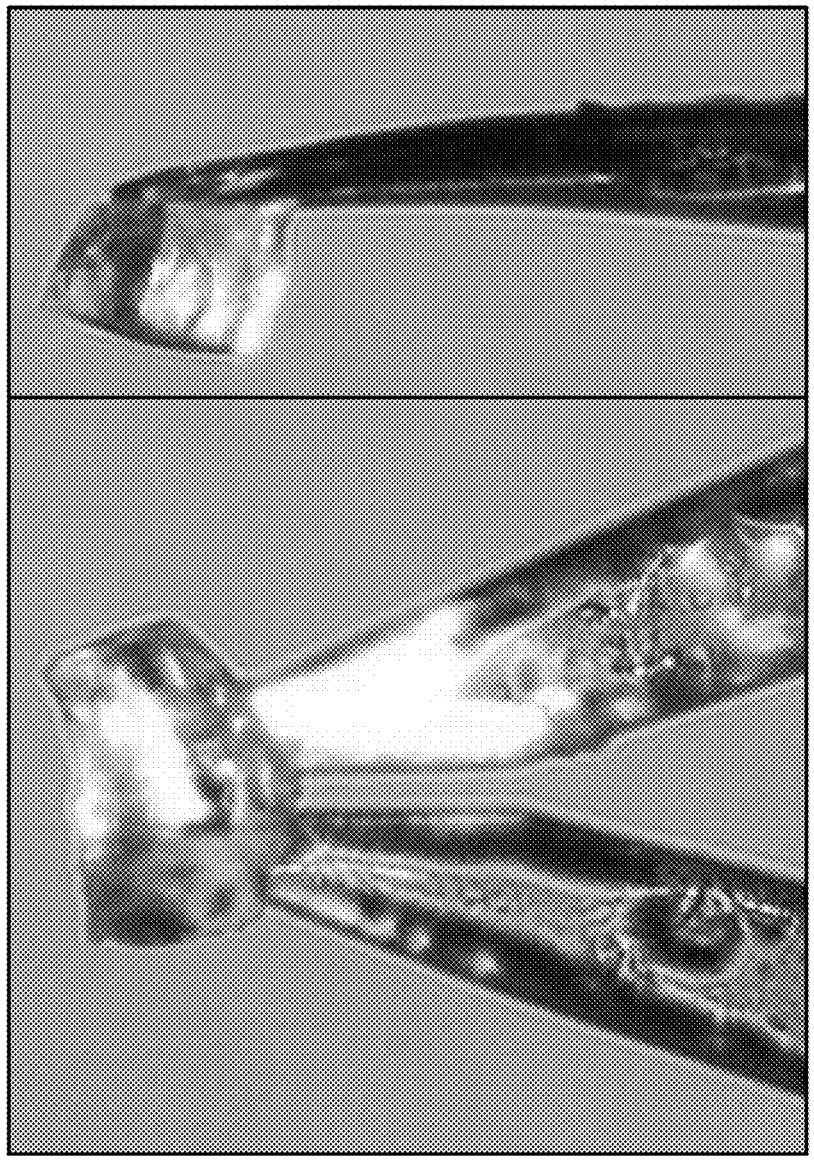

This application is a continuation of U.S. patent application Ser. No. 13/277,615, filed Oct. 20, 2011, currently allowed, which claims the benefit of U.S. Provisional Application No. 61/406,292, filed Oct. 25, 2010, claims the benefit of U.S. Provisional Application No. 61/481,378, filed May 2, 2011, claims the benefit of U.S. Provisional Application No. 61/528,427, filed Aug. 29, 2011, and claims the benefit of U.S. Provisional Application No. 61/537,963, filed Sep. 22, 2011, the entire contents of each of which are incorporated herein by reference.

2. FIELD

Provided herein are compounds and pharmaceutical formulations comprising 4-((9-((3S)-tetrahydro-3-furanyl)-8-((2,4,6-trifluorophenyl)amino)-9H-purin-2-yl)amino)-trans-cyclohexanol, including pharmaceutically acceptable salts, solvates, isomers, isotopologues, tautomers and racemic mixtures thereof, and a pharmaceutically acceptable excipient; and pharmaceutical uses thereof.

3. BACKGROUND

The preparation and certain uses of 4-((9-((3S)-tetrahydro-3-furanyl)-8-((2,4,6-trifluorophenyl)amino)-9H-purin-2-yl)amino)-trans-cyclohexanol, alternatively referred to as (1S,4r)-4-(9-((S)-tetrahydrofuran-3-yl)-8-(2,4,6-trifluorophenylamino)-9H-purin-2-ylamino)cyclohexanol and 4-(9-(tetrahydro-furan-3-yl)-8-(2,4,6-trifluoro-phenylamino)-9H-purin-2-ylamino)-cyclohexan-1-ol, have been described in U.S. Pat. Nos. 7,521,446, 7,723,340, and 7,759,342; U.S. Pat. App. Pub. Nos. 2009/275564, 2009/312320, 2010/249066, and 2009/0048275; and International Pub. Nos. WO 2006/076595, WO 2007/127382, and WO 2008/057252; the disclosure of each of which is incorporated herein by reference in its entirety.

The identification and selection of a formulation of a pharmaceutical compound is complex, given that a change in a formulation may affect a variety of physical and chemical properties, which may provide benefits or drawbacks in safety, processing, stability, solubility and bioavailability, among other important pharmaceutical characteristics.

Notably, the various excipients employed in a formulation of a pharmaceutical compound can have a profound effect on the manufacturing process, wherein characteristics such as flowability (e.g., blend flow), hardness, compressibility, sticking, filming and capping can be affected by the identity and amount of the excipients employed.

Potential formulations include, but are not limited to solid, liquid and aerosol formulations. Potential solid formulations include, but are not limited to, tablet and capsule formulations. The variety of possible formulations creates potential diversity in physical and chemical properties for a given pharmaceutical compound. The discovery and selection of the optimal formulation is of great importance in the development of a safe, effective, stable and marketable pharmaceutical product.

Notably, 4-((9-((3S)-tetrahydro-3-furanyl)-8-((2,4,6-trifluorophenyl)amino)-9H-purin-2-yl)amino)-trans-cyclohexanol is a fine white powder with a fluffy appearance, which exhibits poor flow. In addition, 4-((9-((3S)-tetrahydro-3-furanyl)-8-((2,4,6-trifluorophenyl)amino)-9H-purin-2-yl)amino)-trans-cyclohexanol exhibits low aqueous solubility, at a level of less than 1 mg/mL.

Accordingly, there is a need in the art for formulations that impart more desirable chemical and physical properties.

Teratogenic agents can disturb the growth of an embryo or fetus. Accordingly, exposure to teratogenic agents should be avoided by females who are pregnant or may become pregnant and by males who may come into contact with such females. One strategy for reducing or minimizing such exposure for teratogenic pharmaceutical agents is to provide the final product in a form that minimizes such exposure, such as a capsule formulation or a coated tablet formulation. Such formulations can reduce the exposure of, for example, workers who might come into contact with the teratogenic agent in a manufacturing setting, as well as patients being administered the teratogenic agent, in addition to health care providers and others who might come into contact with the teratogenic agent.

Accordingly, there is a need in the art for formulations that reduce the risk of exposure to teratogenic pharmaceutical agents.

Capsule formulations, wherein the drug is contained within a capsule shell, offer a route to such formulations. Capsule formulations can comprise a hard outer shell that contains the drug formulation inside, thus reducing exposure to the drug after the manufacturing process is complete. In addition, capsule formulations allow for manufacturing processes that can reduce the handling of the solid formulation. For instance, with the appropriate choice of excipients, it may be possible to direct-fill into capsules, thus reducing exposure to the drug during compression (tablet), film coating and packaging operations. Thus, capsule formulations also may reduce exposure to the drug during the manufacturing process.

Citation or identification of any references in this application is not to be construed as an admission that the references are prior art to the present application.

4. SUMMARY

Formulations of pharmaceutical agents are critical for proper drug delivery. Formulations achieving an effective bioavailability, while also protecting the patient and health care provider are needed. Furthermore, formulations that allow for scaled up manufacturing processes to be carried out in a time and cost-efficient manner are also needed. In addition, formulations with desirable dissolution profiles (i.e., correlating to desirable bioavailability) are also needed.

Accordingly, provided herein are pharmaceutical formulations comprising 4-((9-((3S)-tetrahydro-3-furanyl)-8-((2,4,6-trifluorophenyl)amino)-9H-purin-2-yl)amino)-trans-cyclohexanol, having the following structure:

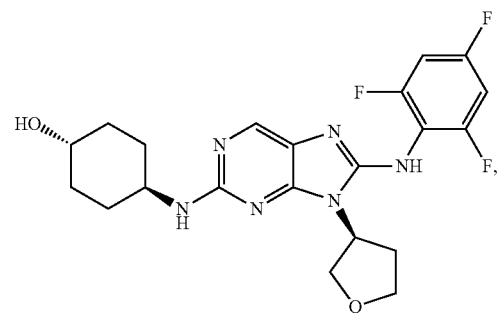 [SMILES: O[C@H]1CC[C@H](Nc2ncc3nc(Nc4c(F)cc(F)cc4F)n([C@H]4CCOC4)c3n2)CC1]

or pharmaceutically acceptable salts, solvates, isomers, isotopologues, tautomers or racemic mixtures thereof (all of which are included within the term "Compound I" as used herein), useful for the treatment, prevention or management of disease, wherein the formulation reduces the risk of unintended exposure to the active agent, has desirable manufacturing properties and has a desirable dissolution profile. Alternative names for 4-((9-((3S)-tetrahydro-3-furanyl)-8-((2,4,6-trifluorophenyl)amino)-9H-purin-2-yl)amino)-trans-cyclohexanol include (1S,4r)-4-(9-((S)-tetrahydrofuran-3-yl)-8-(2,4,6-trifluorophenylamino)-9H-purin-2-ylamino)cyclohexanol (chemical name generated using ChemBioDraw Ultra, version 11.0.1; Cambridgesoft, Cambridge, Mass.) and 4-(9-(tetrahydro-furan-3-yl)-8-(2,4,6-trifluoro-phenylamino)-9H-purin-2-ylamino)-cyclohexan-1-ol (both of which are included within the term "Compound I" as used herein). In one embodiment, the tautomer of 4-((9-((3S)-tetrahydro-3-furanyl)-8-((2,4,6-trifluorophenyl)amino)-9H-purin-2-yl)amino)-trans-cyclohexanol is (1S,4r)-4-((E)-9-((S)-tetrahydrofuran-3-yl)-8-(2,4,6-trifluorophenylimino)-8,9-dihydro-7H-purin-2-ylamino)cyclohexanol (chemical name generated using ChemBioDraw Ultra, version 11.0.1; Cambridgesoft, Cambridge, Mass.). In certain embodiments, 4-((9-((3S)-tetrahydro-3-furanyl)-8-((2,4,6-trifluorophenyl)amino)-9H-purin-2-yl)amino)-trans-cyclohexanol exists as amine-imine tautomers as shown below:

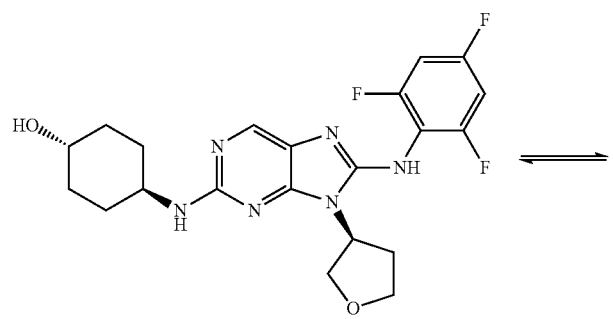 ⇌ 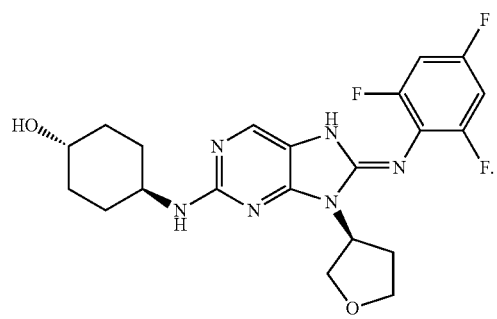

In one embodiment, provided herein are pharmaceutical formulations comprising 4-((9-((3S)-tetrahydro-3-furanyl)-8-((2,4,6-trifluorophenyl)amino)-9H-purin-2-yl)amino)-trans-cyclohexanol, or pharmaceutically acceptable salts, solvates, isomers, isotopologues, tautomers or racemic mixtures thereof, useful for the treatment, prevention or management of disease, wherein the pharmaceutical formulation is formulated as a capsule.

In one embodiment, provided herein are pharmaceutical formulations comprising 4-((9-((3S)-tetrahydro-3-furanyl)-8-((2,4,6-trifluorophenyl)amino)-9H-purin-2-yl)amino)-trans-cyclohexanol, or pharmaceutically acceptable salts, solvates, isomers, isotopologues, tautomers or racemic mixtures thereof, useful for the treatment, prevention or management of disease, wherein the pharmaceutical formulation is formulated as a coated tablet.

In one embodiment, provided herein are pharmaceutical formulations comprising 4-((9-((3S)-tetrahydro-3-furanyl)-8-((2,4,6-trifluorophenyl)amino)-9H-purin-2-yl)amino)-trans-cyclohexanol, or pharmaceutically acceptable salts, solvates, isomers, isotopologues, tautomers or racemic mixtures thereof, and silicified microcrystalline cellulose.

Also provided herein are pharmaceutical formulations comprising 4-((9-((3S)-tetrahydro-3-furanyl)-8-((2,4,6-trifluorophenyl)amino)-9H-purin-2-yl)amino)-trans-cyclohexanol, or pharmaceutically acceptable salts, solvates, isomers, isotopologues, tautomers or racemic mixtures thereof, and silicified microcrystalline cellulose, in combination with one or more diluent, disintegrant, and/or lubricant.

In one embodiment, provided herein are pharmaceutical formulations comprising 4-((9-((3S)-tetrahydro-3-furanyl)-8-((2,4,6-trifluorophenyl)amino)-9H-purin-2-yl)amino)-trans-cyclohexanol, or pharmaceutically acceptable salts, solvates, isomers, isotopologues, tautomers or racemic mixtures thereof, and silicified microcrystalline cellulose, in combination with lactose, croscarmellose sodium, and/or magnesium stearate.

Provided herein are pharmaceutical formulations comprising from about 10 to about 60% by weight (also referred to herein is w/w) of 4-((9-((3S)-tetrahydro-3-furanyl)-8-((2,4,6-trifluorophenyl)amino)-9H-purin-2-yl)amino)-trans-cyclohexanol, or pharmaceutically acceptable salts, solvates, isomers, isotopologues, tautomers or racemic mixtures thereof, and from about 20 to about 70% w/w of silicified microcrystalline cellulose.

In one embodiment, provided herein are pharmaceutical formulations comprising 4-((9-((3S)-tetrahydro-3-furanyl)-8-((2,4,6-trifluorophenyl)amino)-9H-purin-2-yl)amino)-trans-cyclohexanol, or pharmaceutically acceptable salts, solvates, isomers, isotopologues, tautomers or racemic mixtures thereof, and about 45-60% w/w microcrystalline cellulose. In one embodiment, the microcrystalline cellulose is silicified.

In one embodiment, provided herein are pharmaceutical formulations comprising 4-((9-((3S)-tetrahydro-3-furanyl)-8-((2,4,6-trifluorophenyl)amino)-9H-purin-2-yl)amino)-trans-cyclohexanol, or pharmaceutically acceptable salts, solvates, isomers, isotopologues, tautomers or racemic mixtures thereof, and about 0.5% w/w or less of a lubricant.

In one embodiment, provided herein are pharmaceutical formulations comprising 4-((9-((3S)-tetrahydro-3-furanyl)-8-((2,4,6-trifluorophenyl)amino)-9H-purin-2-yl)amino)-trans-cyclohexanol, or pharmaceutically acceptable salts, solvates, isomers, isotopologues, tautomers or racemic mixtures thereof, in combination with a microcrystalline cellulose and a starch. In one embodiment, the microcrystalline cellulose is silicified.

In one embodiment, provided herein are pharmaceutical formulations comprising 4-((9-((3S)-tetrahydro-3-furanyl)-8-((2,4,6-trifluorophenyl)amino)-9H-purin-2-yl)amino)-trans-cyclohexanol, or pharmaceutically acceptable salts, solvates, isomers, isotopologues, tautomers or racemic mixtures thereof, and about 40-60% w/w lactose.

In one embodiment, provided herein are pharmaceutical formulations comprising 4-((9-((3S)-tetrahydro-3-furanyl)-8-((2,4,6-trifluorophenyl)amino)-9H-purin-2-yl)amino)-trans-cyclohexanol, or pharmaceutically acceptable salts, solvates, isomers, isotopologues, tautomers or racemic mixtures thereof, in combination with microcrystalline cellulose, lactose and Cab-O-Sil®. In one embodiment, the microcrystalline cellulose is silicified.

In one embodiment, provided herein are pharmaceutical formulations comprising 4-((9-((3S)-tetrahydro-3-furanyl)-8-((2,4,6-trifluorophenyl)amino)-9H-purin-2-yl)amino)-trans-cyclohexanol, or pharmaceutically acceptable salts, solvates, isomers, isotopologues, tautomers or racemic mixtures thereof, in combination with AVICEL® PH 105 and/or AVICEL® PH 302.

In one embodiment, provided herein are unit-dosage forms of a pharmaceutical formulation comprising 4-((9-((3S)-tetrahydro-3-furanyl)-8-((2,4,6-trifluorophenyl)amino)-9H-purin-2-yl)amino)-trans-cyclohexanol, or pharmaceutically acceptable salts, solvates, isomers, isotopologues, tautomers or racemic mixtures thereof, and silicified microcrystalline cellulose. In one embodiment, the pharmaceutical formulation is formulated as a capsule.

In one embodiment, provided herein are unit-dosage forms of a pharmaceutical formulation comprising 4-((9-((3S)-tetrahydro-3-furanyl)-8-((2,4,6-trifluorophenyl)amino)-9H-purin-2-yl)amino)-trans-cyclohexanol, or pharmaceutically acceptable salts, solvates, isomers, isotopologues, tautomers or racemic mixtures thereof, and silicified microcrystalline cellulose, in combination with a diluent, a disintegrant, and/or a lubricant.

In one embodiment, provided herein are unit-dosage forms of a pharmaceutical formulation comprising 4-((9-((3S)-tetrahydro-3-furanyl)-8-((2,4,6-trifluorophenyl)amino)-9H-purin-2-yl)amino)-trans-cyclohexanol, or pharmaceutically acceptable salts, solvates, isomers, isotopologues, tautomers or racemic mixtures thereof, and silicified microcrystalline cellulose, in combination with lactose, croscarmellose sodium, and/or magnesium stearate.

In one embodiment, provided herein are unit-dosage forms of a pharmaceutical formulation comprising from about 5 to about 500 mg of 4-((9-((3S)-tetrahydro-3-furanyl)-8-((2,4,6-trifluorophenyl)amino)-9H-purin-2-yl)amino)-trans-cyclohexanol, or pharmaceutically acceptable salts, solvates, isomers, isotopologues, tautomers or racemic mixtures thereof and from about 5 to about 500 mg of silicified microcrystalline cellulose.

The pharmaceutical formulations provided herein are useful for treating or preventing: (a) a cancer; (b) an inflammatory condition; (c) an immunological condition; (d) an autoimmune condition; (e) a metabolic condition; or (f) a fibrotic condition; comprising administering to a subject in need thereof an effective amount of one of the pharmaceutical formulations provided herein; wherein:

(a) the cancer is of the head, neck, eye, mouth, throat, esophagus, bronchus, larynx, pharynx, chest, bone, lung, colon, rectum, stomach, prostate, urinary bladder, uterine, cervix, breast, ovaries, testicles, skin, thyroid, blood, lymph nodes, kidney, liver, pancreas, brain or central nervous system;

(b) the inflammatory condition is asthma, allergic rhinitis, bronchitis, chronic obstructive pulmonary disease, cystic fibrosis, inflammatory bowel disease, irritable bowel syndrome, Crohn's disease, mucous colitis, ulcerative colitis, diabetes or obesity;

(c) the immunological condition is rheumatoid arthritis, rheumatoid spondylitis, osteoarthritis, multiple sclerosis, lupus (including cutaneous lupus erythematosus and discoid lupus erythematosus, such as recalcitrant discoid lupus erythematosus), inflammatory bowel disease, ulcerative colitis, Crohn's disease, myasthenia gravis, Grave's disease or diabetes;

(d) the autoimmune condition is rheumatoid arthritis, rheumatoid spondylitis, osteoarthritis, multiple sclerosis, lupus (including cutaneous lupus erythematosus and discoid lupus erythematosus, such as recalcitrant discoid lupus erythematosus), inflammatory bowel disease, ulcerative colitis, Crohn's disease, myasthenia gravis, Grave's disease, Type I diabetes or systemic sclerosis;

(e) the metabolic condition is obesity or diabetes; and (f) the fibrotic condition is idiopathic pulmonary fibrosis, myelofibrosis, hepatic fibrosis, renal fibrosis, chronic allograft nephropathy, (including chronic allograft dysfunction) glomerulonephritis, glomerular nephropathy, glomerulopathies, steatofibrosis, steatohepatitis (including non-alcoholic steatohepatitis), or scleroderma.

The pharmaceutical formulations provided herein are useful for treating or preventing scleroderma, keloids, UV injury, or sunburn, and for improving or preventing scar formation.

In one embodiment, the pharmaceutical formulations provided herein are useful for treating or preventing a disease treatable or preventable by inhibition of a kinase pathway, in one embodiment, the JNK pathway.

In one embodiment, the pharmaceutical formulations provided herein reduce or alleviate risks associated with contacting a teratogenic agent, such as abnormal development in embryos, congenital malformations or birth defects.

Provided herein are methods for treating or preventing: (a) a cancer; (b) an inflammatory condition; (c) an immunological condition; (d) an autoimmune condition; (e) a metabolic condition; or (f) a fibrotic condition; comprising administering to a subject in need thereof an effective amount of one of the pharmaceutical formulations provided herein; wherein:

(a) the cancer is of the head, neck, eye, mouth, throat, esophagus, bronchus, larynx, pharynx, chest, bone, lung, colon, rectum, stomach, prostate, urinary bladder, uterine, cervix, breast, ovaries, testicles, skin, thyroid, blood, lymph nodes, kidney, liver, pancreas, brain or central nervous system;

(b) the inflammatory condition is asthma, allergic rhinitis, bronchitis, chronic obstructive pulmonary disease, cystic fibrosis, inflammatory bowel disease, irritable bowel syndrome, Crohn's disease, mucous colitis, ulcerative colitis, diabetes or obesity;

(c) the immunological condition is rheumatoid arthritis, rheumatoid spondylitis, osteoarthritis, multiple sclerosis, lupus (including cutaneous lupus erythematosus and discoid lupus erythematosus, such as recalcitrant discoid lupus erythematosus), inflammatory bowel disease, ulcerative colitis, Crohn's disease, myasthenia gravis, Grave's disease or diabetes;

(d) the autoimmune condition is rheumatoid arthritis, rheumatoid spondylitis, osteoarthritis, multiple sclerosis, lupus (including cutaneous lupus erythematosus and discoid lupus erythematosus, such as recalcitrant discoid lupus erythematosus), inflammatory bowel disease, ulcerative colitis, Crohn's disease, myasthenia gravis, Grave's disease, Type I diabetes or systemic sclerosis;

(e) the metabolic condition is obesity or diabetes; and (f) the fibrotic condition is idiopathic pulmonary fibrosis, myelofibrosis, hepatic fibrosis, renal fibrosis, chronic allograft nephropathy (including chronic allograft dysfunction), glomerulonephritis, glomerular nephropathy, glomerulopathies, steatofibrosis, steatohepatitis (including non-alcoholic steatohepatitis), or scleroderma.

Further provided herein are methods for treating or preventing scleroderma, keloids, UV injury, or sunburn, and for improving or preventing scar formation comprising administering to a subject in need thereof an effective amount of one of the pharmaceutical formulations provided herein.

In one embodiment, provided herein are methods for treating or preventing a disease treatable or preventable by inhibition of a kinase pathway, in one embodiment, the JNK pathway.

In certain embodiments, provided herein are methods for preparing a pharmaceutical formulation, comprising: (i)

weighing out the desired amount of 4-((9-((3S)-tetrahydro-3-furanyl)-8-((2,4,6-trifluorophenyl)amino)-9H-purin-2-yl)amino)-trans-cyclohexanol, or a pharmaceutically acceptable salt, solvate, isomer, isotopologue, tautomer or racemic mixture thereof; (ii) passing 4-((9-((3S)-tetrahydro-3-furanyl)-8-((2,4,6-trifluorophenyl)amino)-9H-purin-2-yl)amino)-trans-cyclohexanol, or a pharmaceutically acceptable salt, solvate, isomer, isotopologue, tautomer or racemic mixture thereof through a screen; (iii) weighing out the desired amount of the excipients; (iv) combining 4-((9-((3S)-tetrahydro-3-furanyl)-8-((2,4,6-trifluorophenyl)amino)-9H-purin-2-yl)amino)-trans-cyclohexanol, or a pharmaceutically acceptable salt, solvate, isomer, isotopologue, tautomer or racemic mixture thereof with one or more of the excipients and blending.

In certain embodiments, provided herein are formulations prepared using solid forms, including crystalline forms, of Compound I, having one or more of the characteristics set forth in Examples 6.11-6.12 or FIGS. 1-9.

5. BRIEF DESCRIPTION OF THE DRAWINGS

FIG. 1 provides optical micrographs of the crystal used for data collection.

Figure 2A:
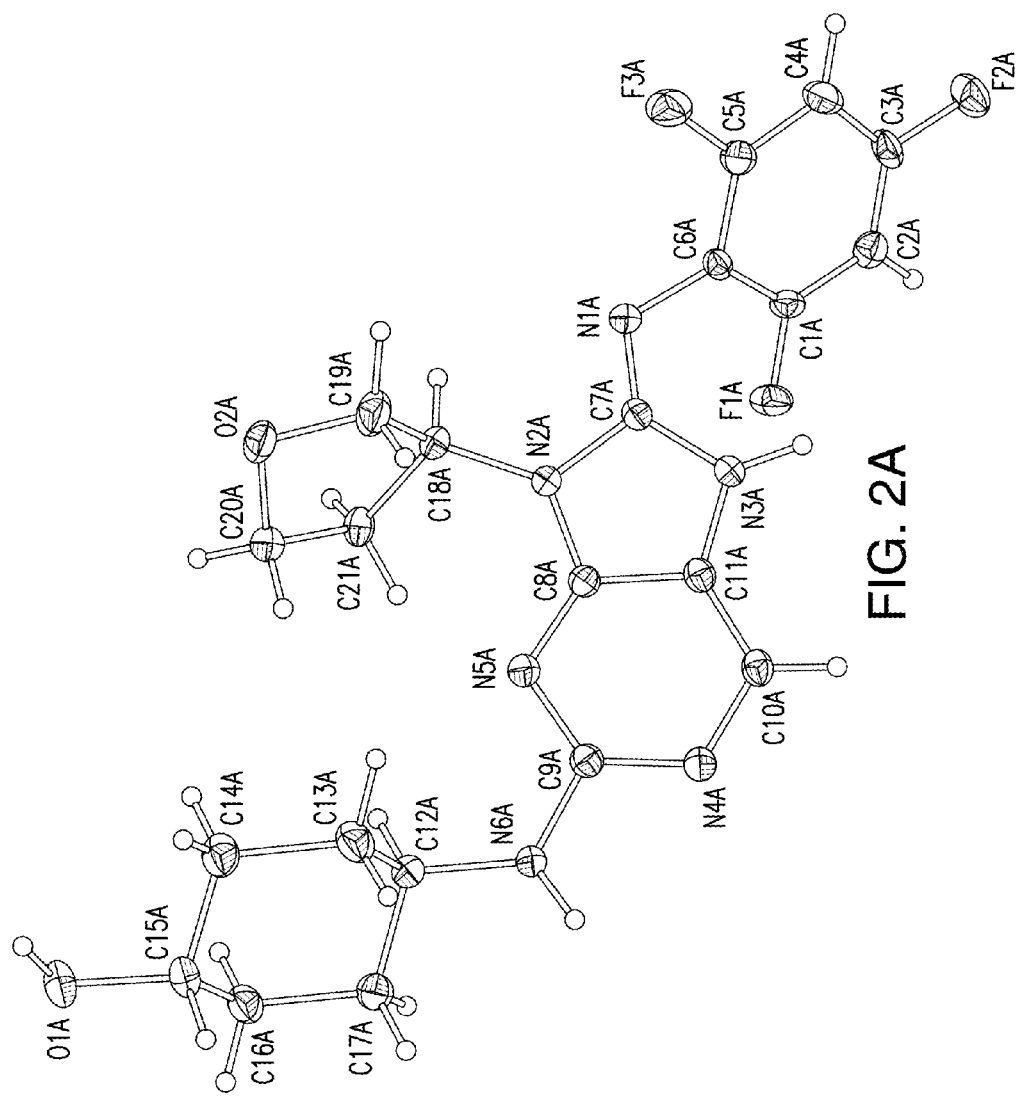

FIG. 2A provides a view of a molecule A from the crystal structure. Anisotropic atomic displacement ellipsoids for the non-hydrogen atoms are shown at the 50% probability level. Hydrogen atoms are displayed with an arbitrarily small radius.

Figure 2B:
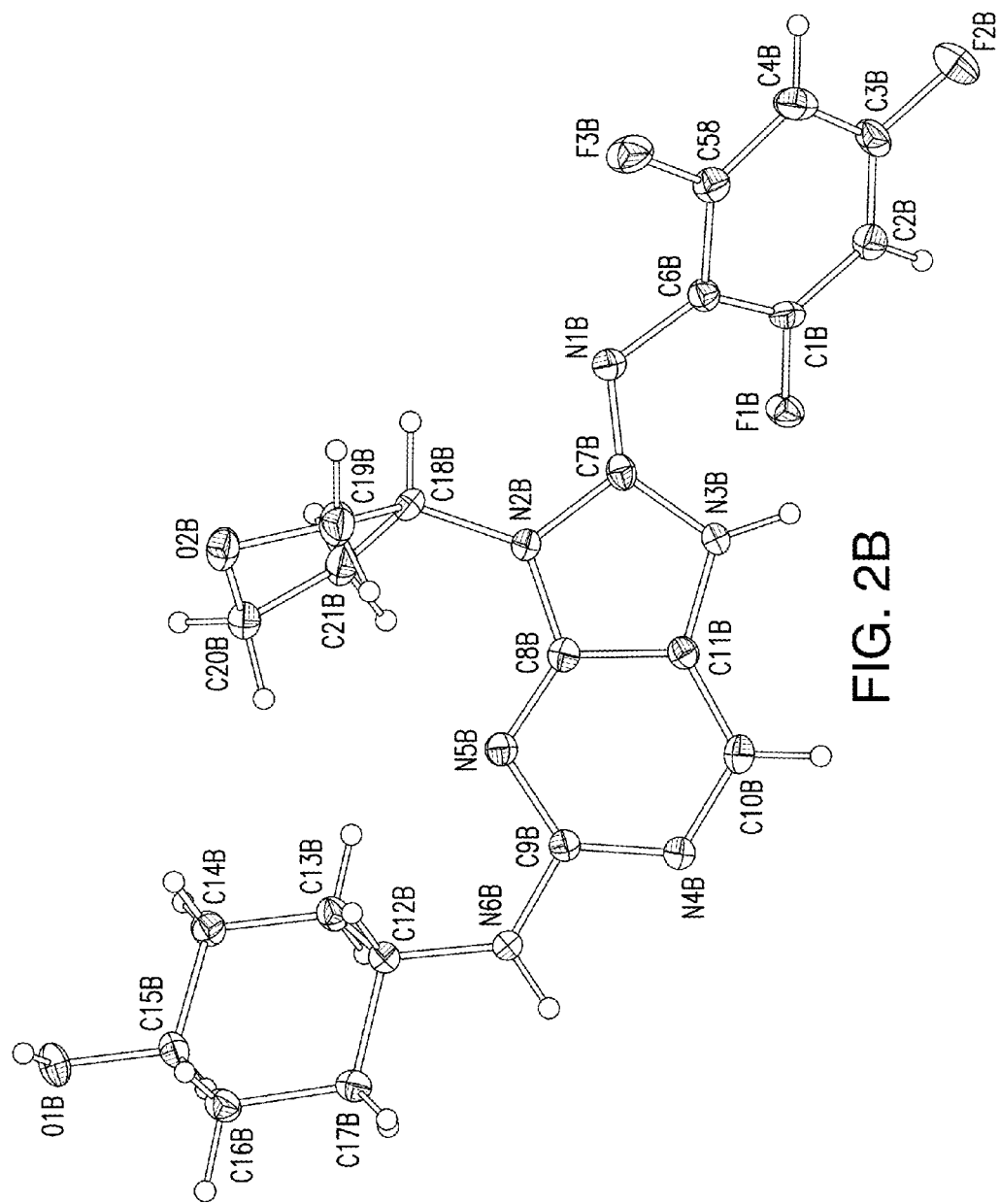

FIG. 2B provides a view of a molecule B from the crystal structure. Anisotropic atomic displacement ellipsoids for the non-hydrogen atoms are shown at the 50% probability level. Hydrogen atoms are displayed with an arbitrarily small radius.

Figure 2C:
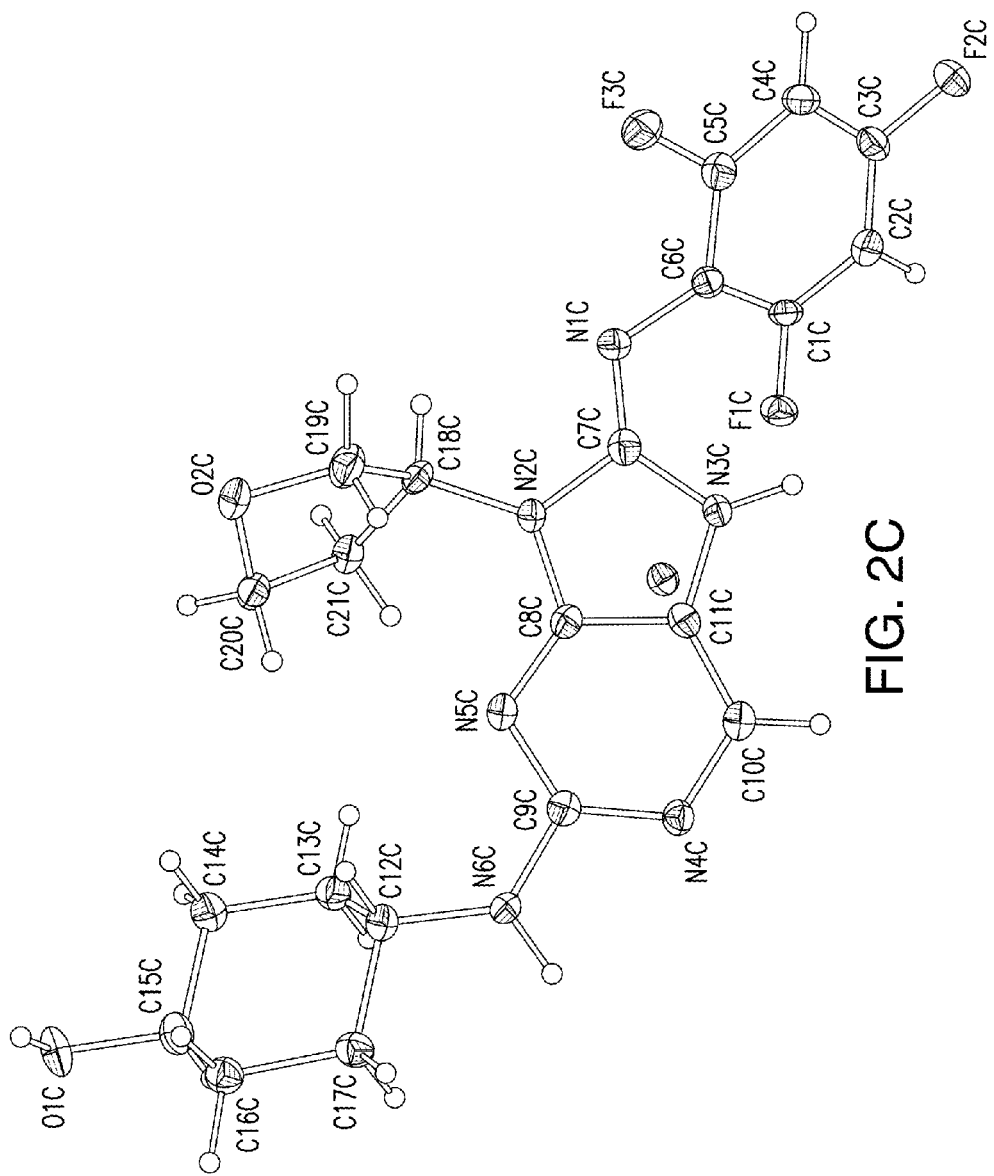

FIG. 2C provides a view of a molecule C from the crystal structure. Anisotropic atomic displacement ellipsoids for the non-hydrogen atoms are shown at the 50% probability level. Hydrogen atoms are displayed with an arbitrarily small radius.

Figure 3:
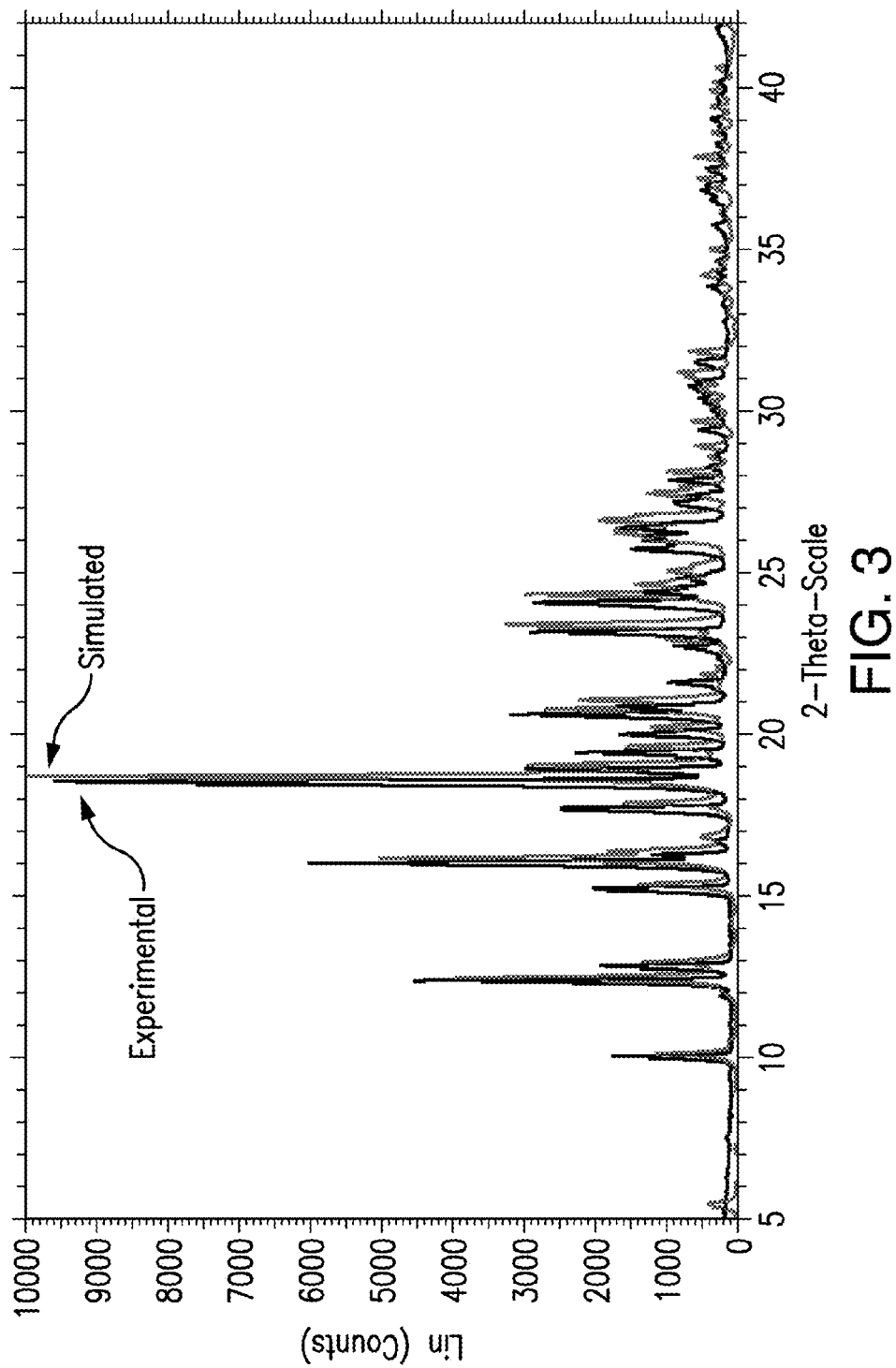

FIG. 3 provides an overlay of the experimental XRPD pattern (solid line) for Compound I with the simulated XRPD pattern (dotted line) derived from the single crystal structure.

Figure 4:
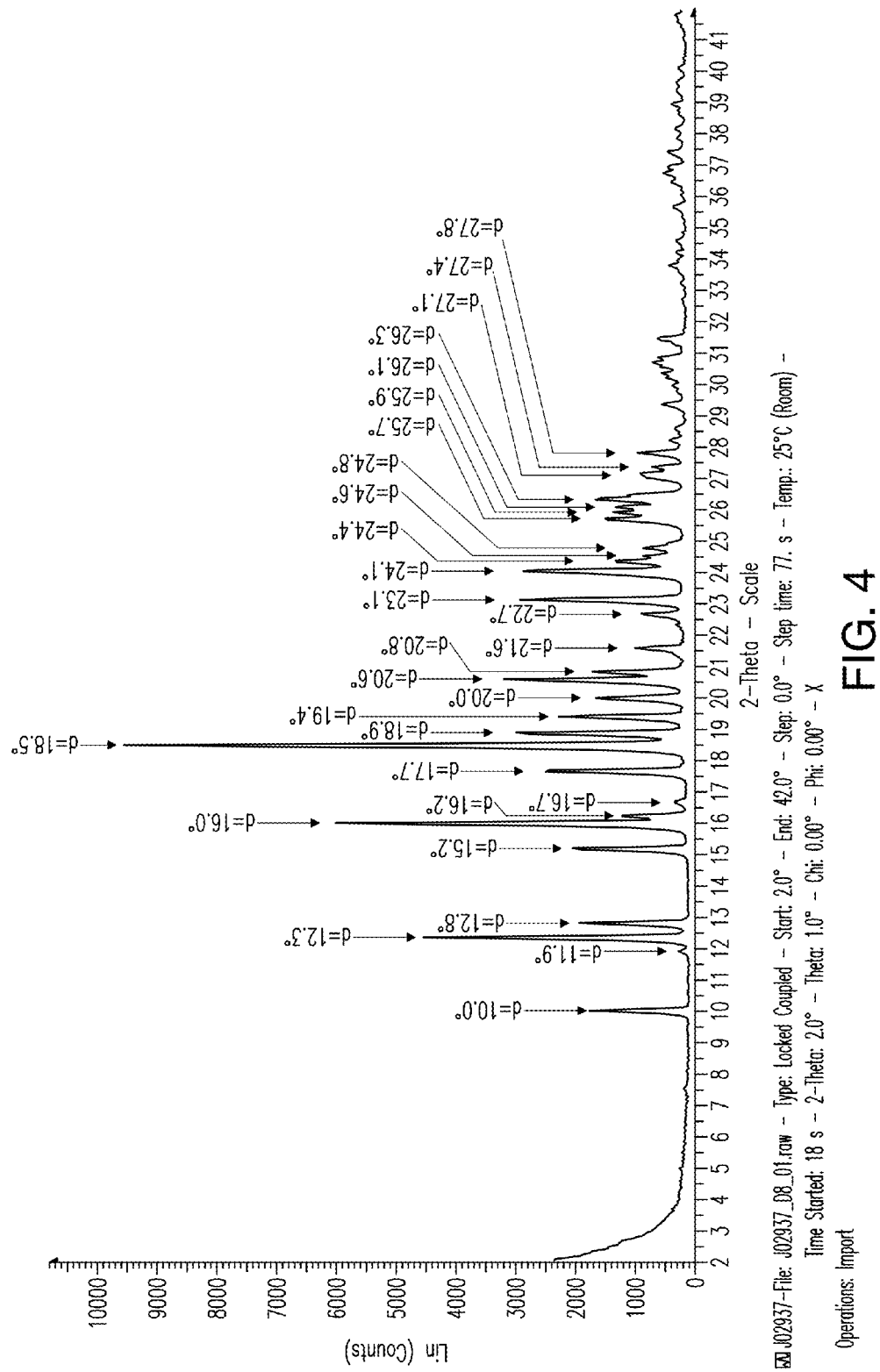

FIG. 4 provides the experimental XRPD pattern derived from the bulk powder of Compound I.

Figure 5:
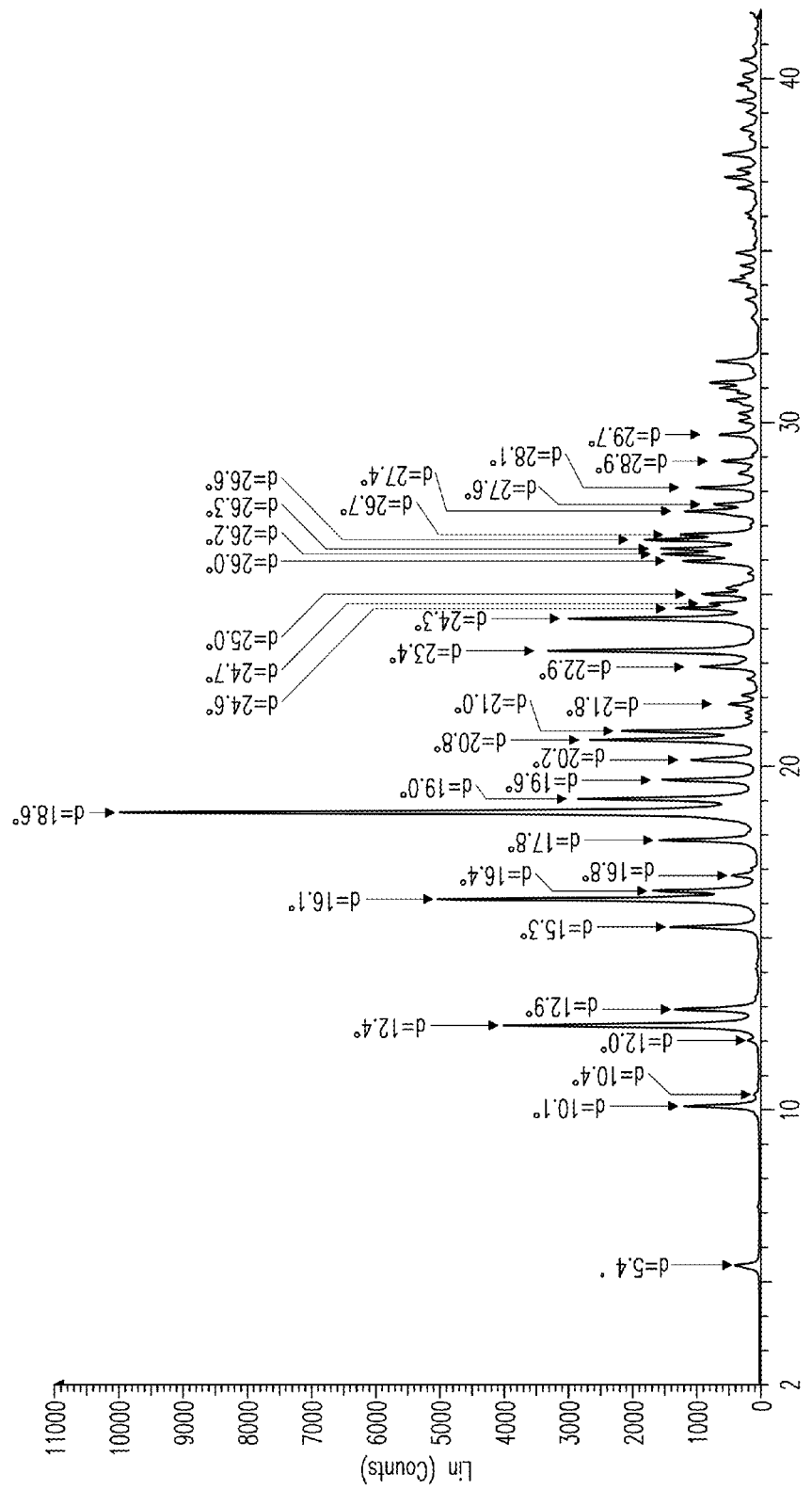

FIG. 5 provides the simulated XRPD pattern derived from the single crystal structure.

Figure 6:
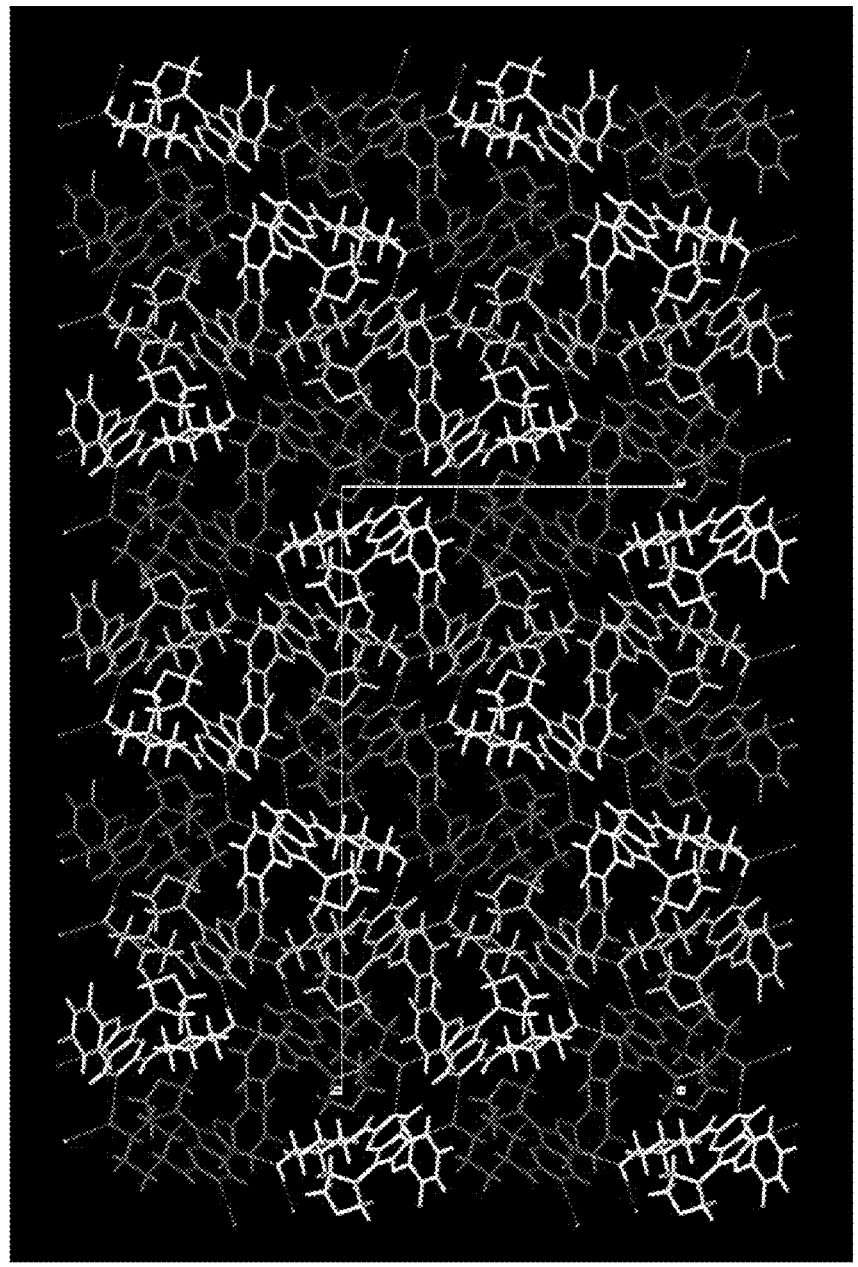

FIG. 6 provides a view of part of the crystal packing of Compound I. The figure shows the formation of the second infinite hydrogen bonded chain of molecules parallel to the b-axis of the unit cell with molecule A, molecule B and molecule C. The view is down the a-axis of the unit cell.

Figure 7:
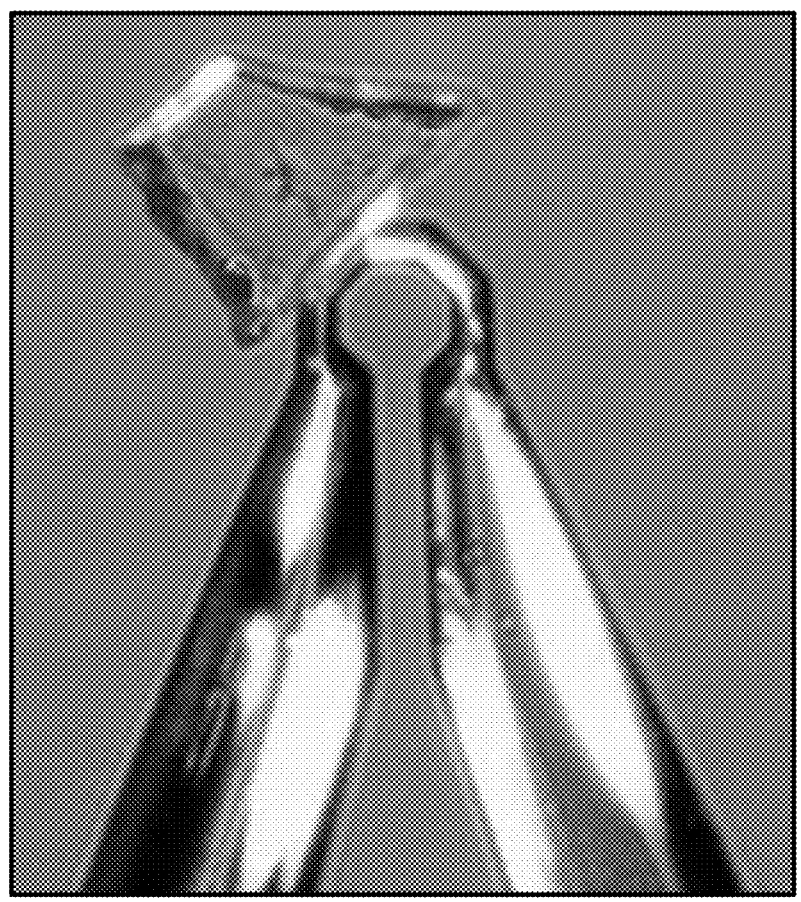

FIG. 7 provides optical micrographs of the crystal used for data collection in connection with the bis-hydrate of Compound I.

Figure 8A:
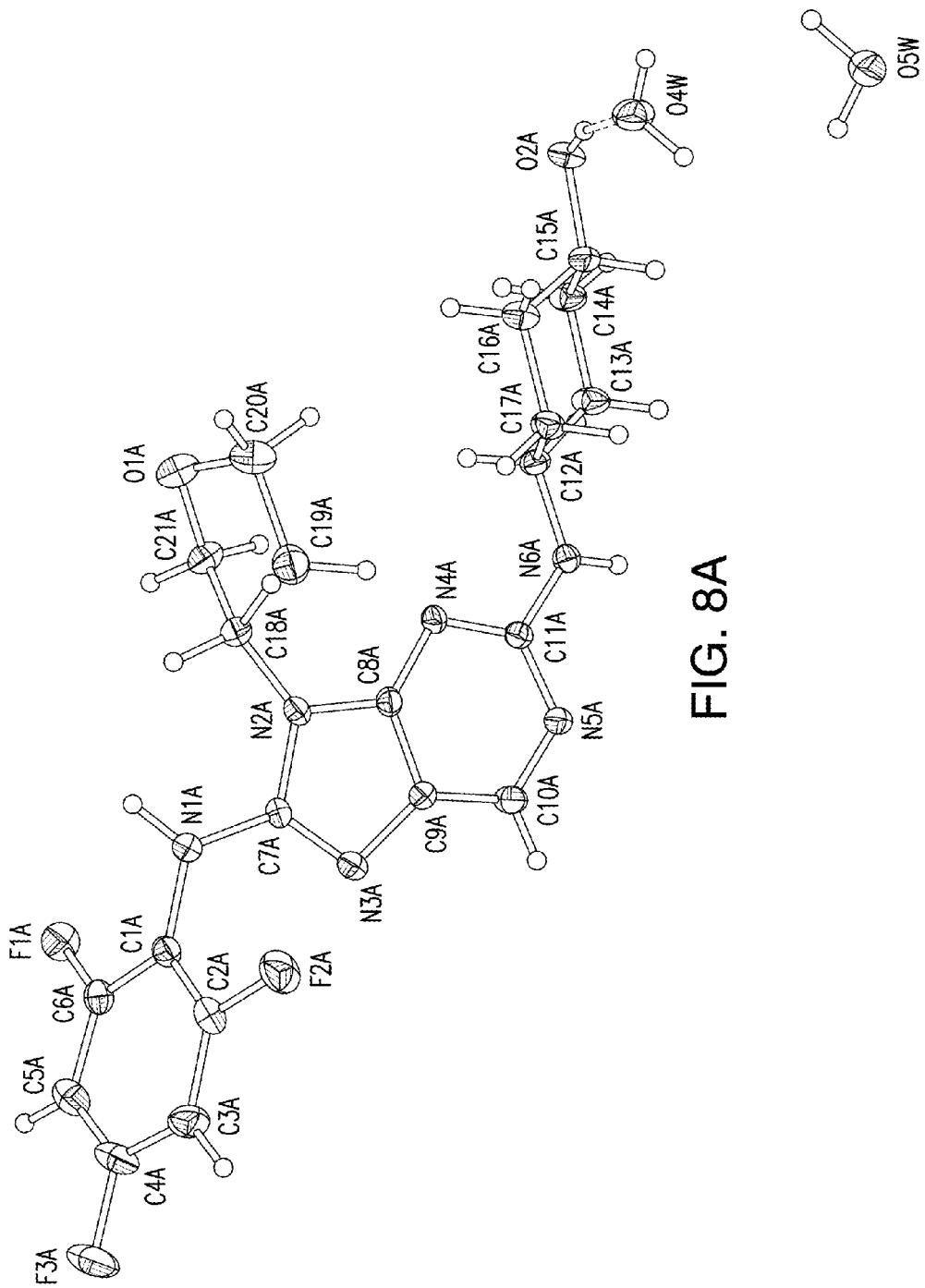

FIG. 8A provides a view of a molecule A, with two molecules of water from the crystal structure. Anisotropic atomic displacement ellipsoids for the non-hydrogen atoms are shown at the 50% probability level. Hydrogen atoms are displayed with an arbitrarily small radius.

Figure 8B:
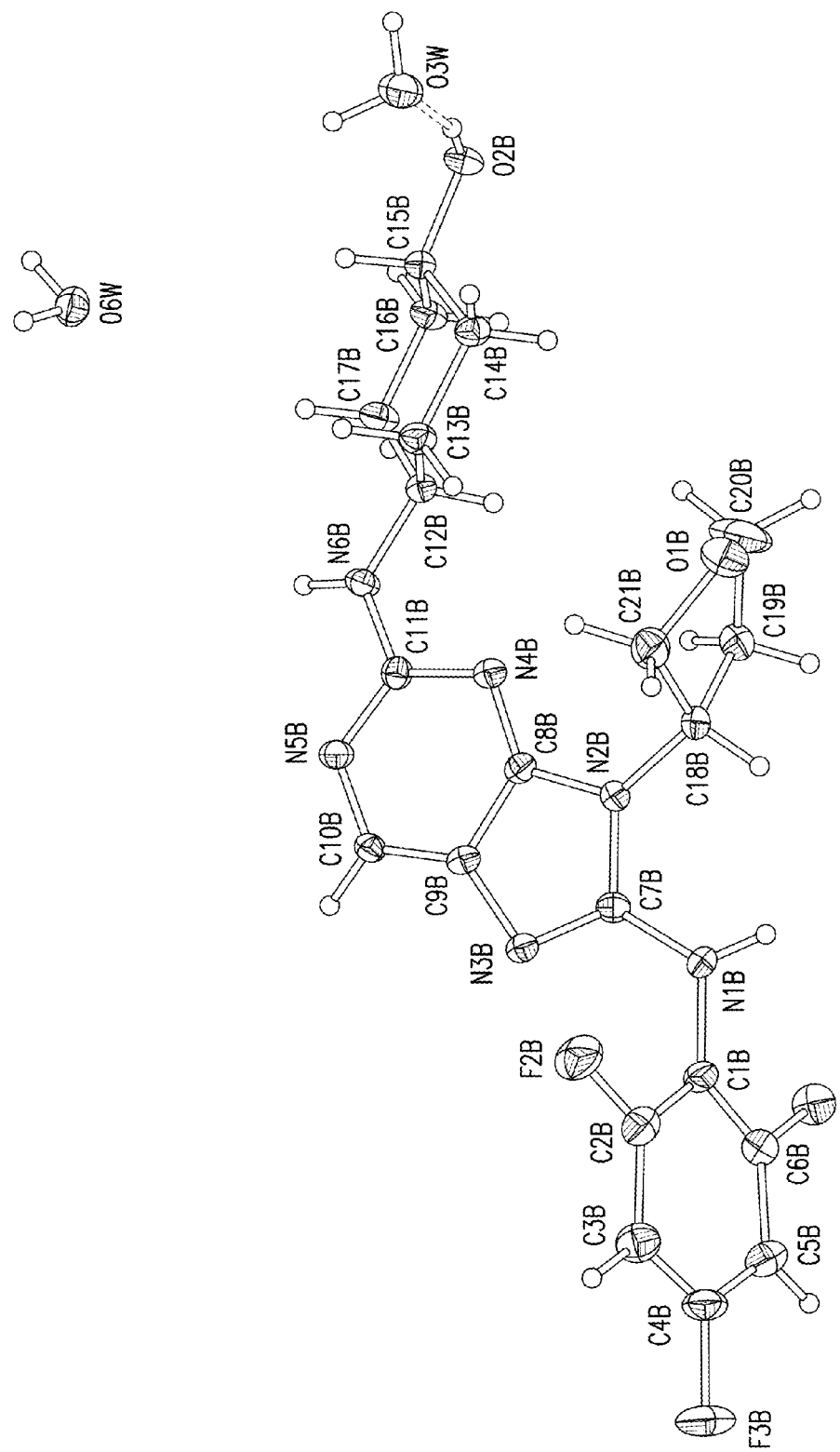

FIG. 8B provides a view of a molecule B, with two molecules of water from the crystal structure. Anisotropic atomic displacement ellipsoids for the non-hydrogen atoms are shown at the 50% probability level. Hydrogen atoms are displayed with an arbitrarily small radius.

Figure 9:
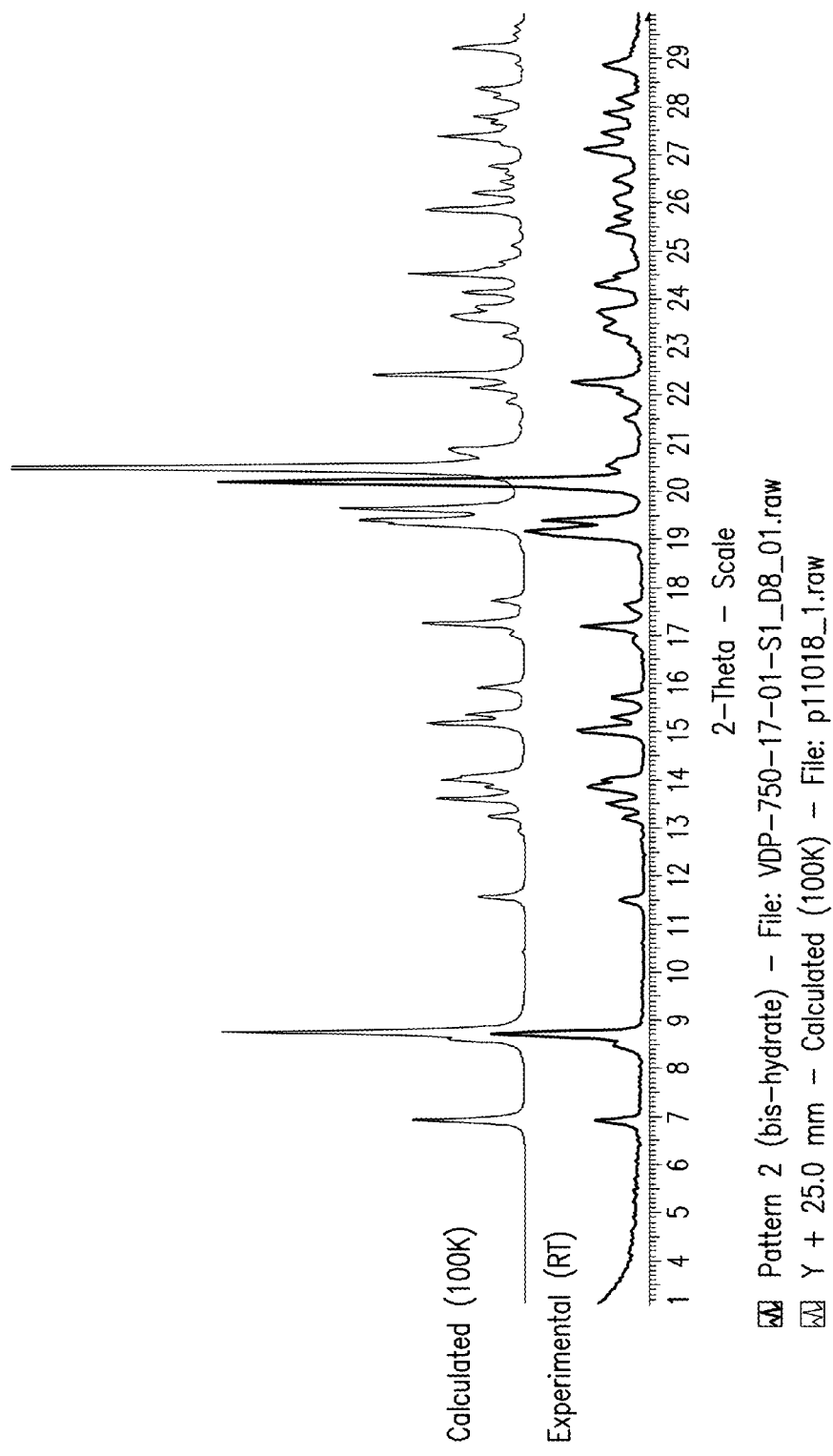

FIG. 9 provides an overlay of the experimental XRPD pattern from the bis-hydrate of Compound I with the simulated (calculated) XRPD pattern derived from the single crystal structure.

Figure 10:
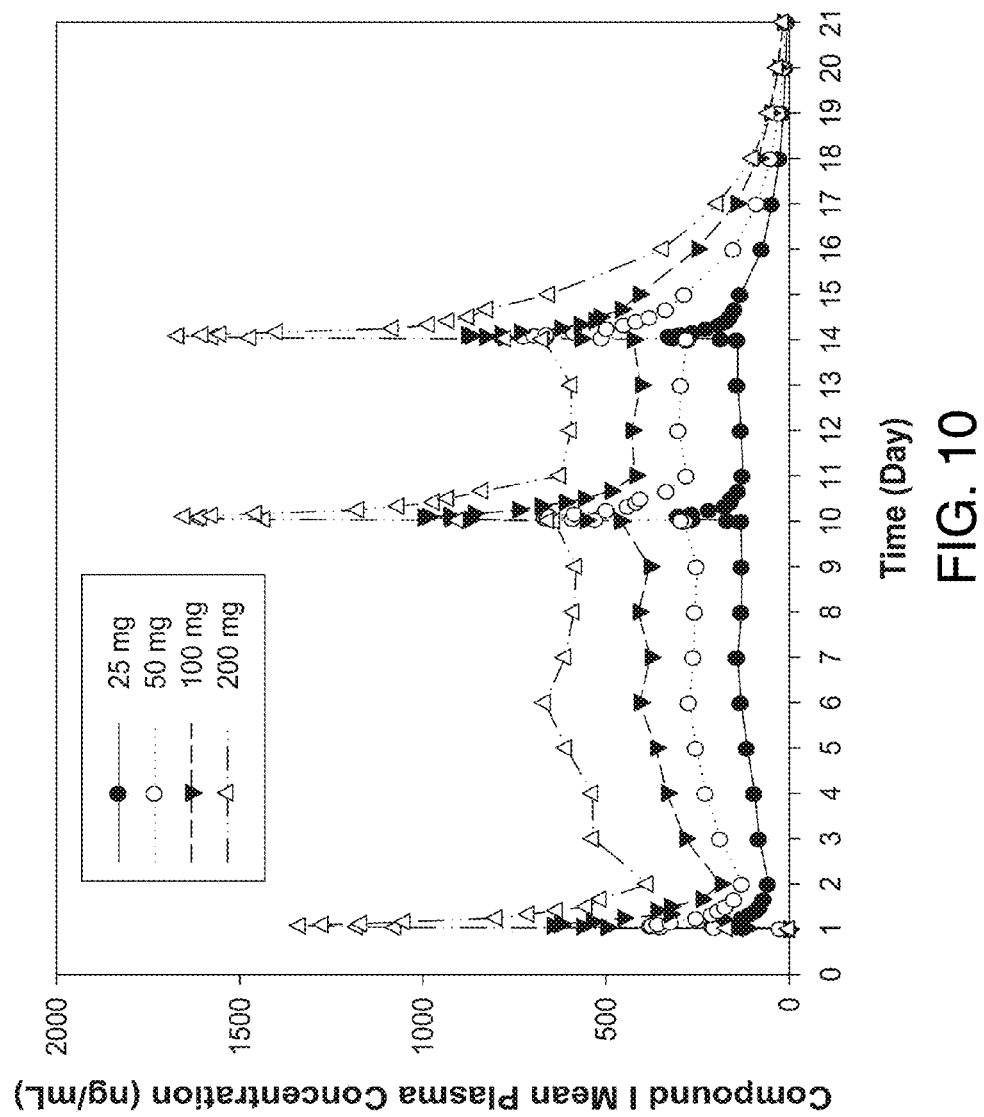

FIG. 10 provides whole profile of mean Compound I plasma concentration versus time across study days (linear scale).

Figure 11A:
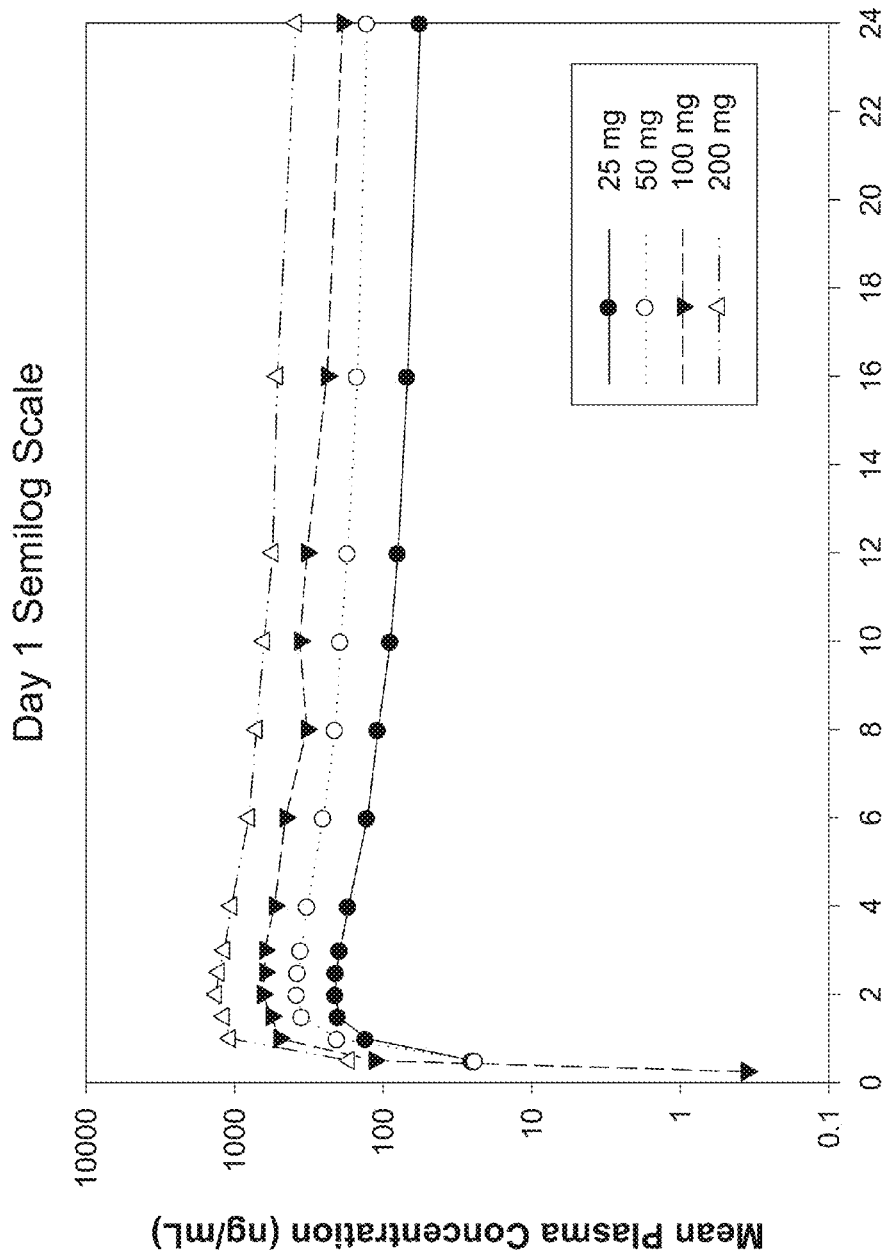

FIG. 11A provides mean Compound I plasma concentration versus time profiles on Day 1 (semi-logarithmic scale).

Figure 11B:
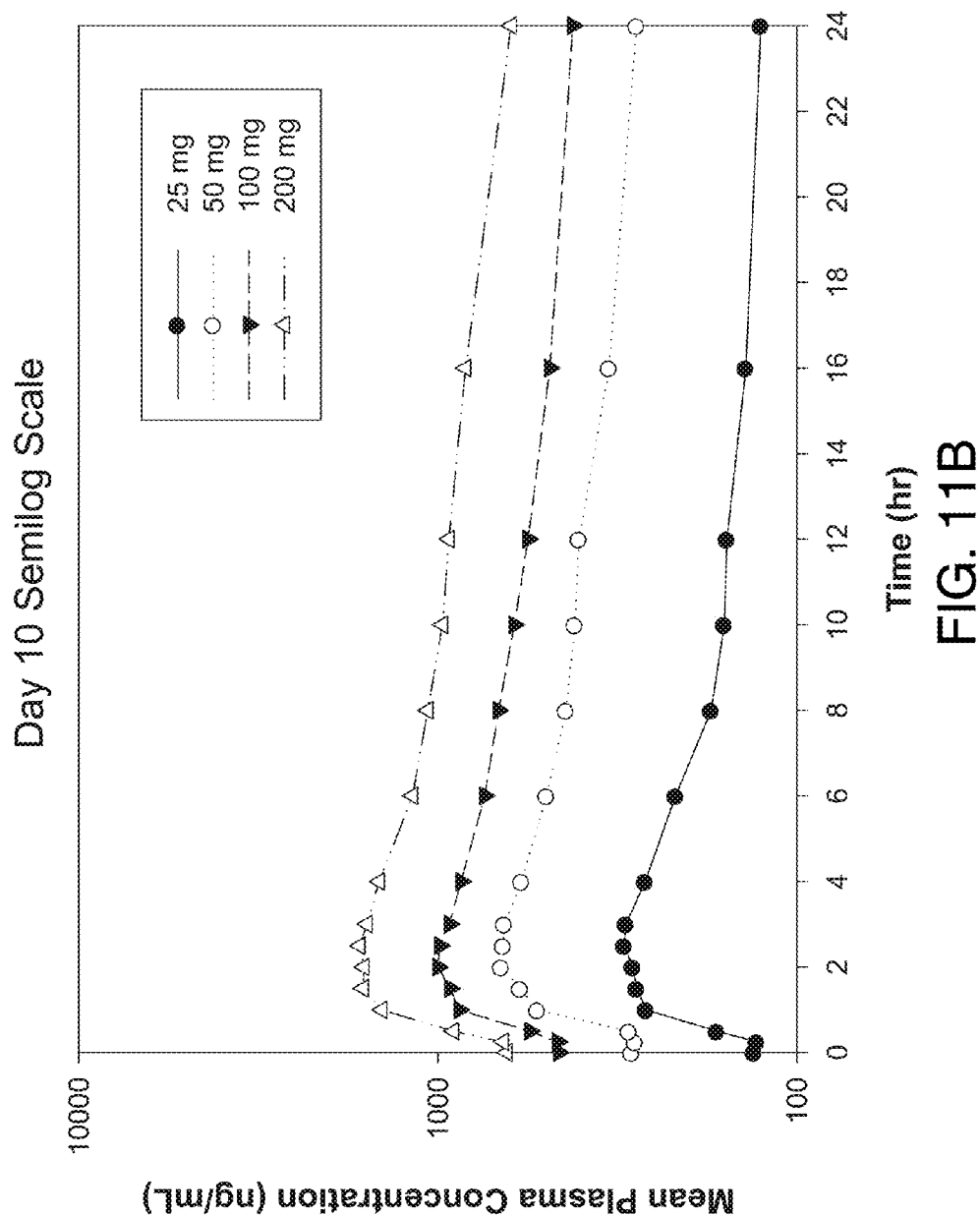

FIG. 11B provides mean Compound I plasma concentration versus time profiles on Day 10 (semi-logarithmic scale).

FIG. 11C provides mean Compound I plasma concentration versus time profiles on Day 14 (semi-logarithmic scale).

Figure 12A:
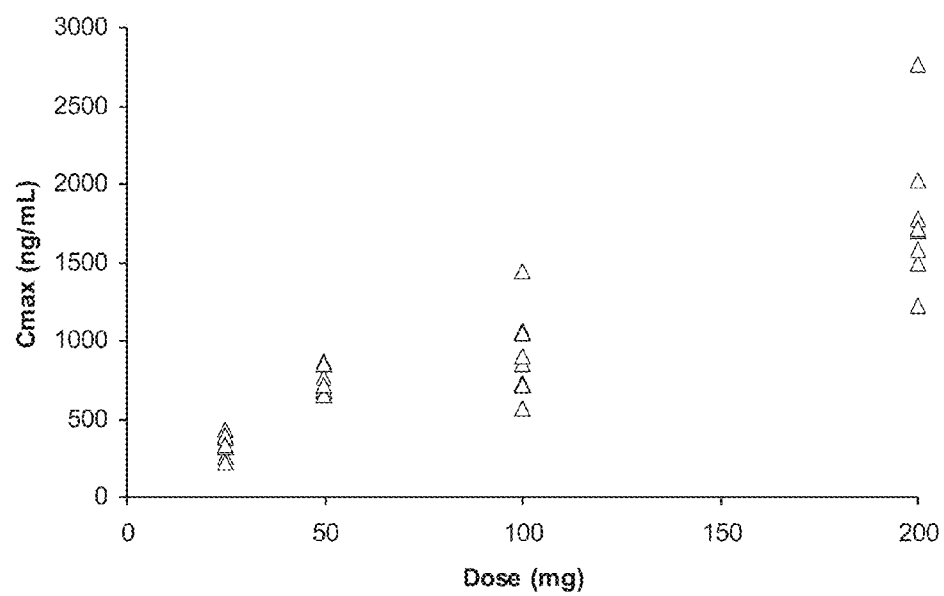

FIG. 12A provides a dose-proportionality assessment of Compound I at steady state ($C_{max}$ on Day 14 vs. Dose (N=8)).

Figure 12B:
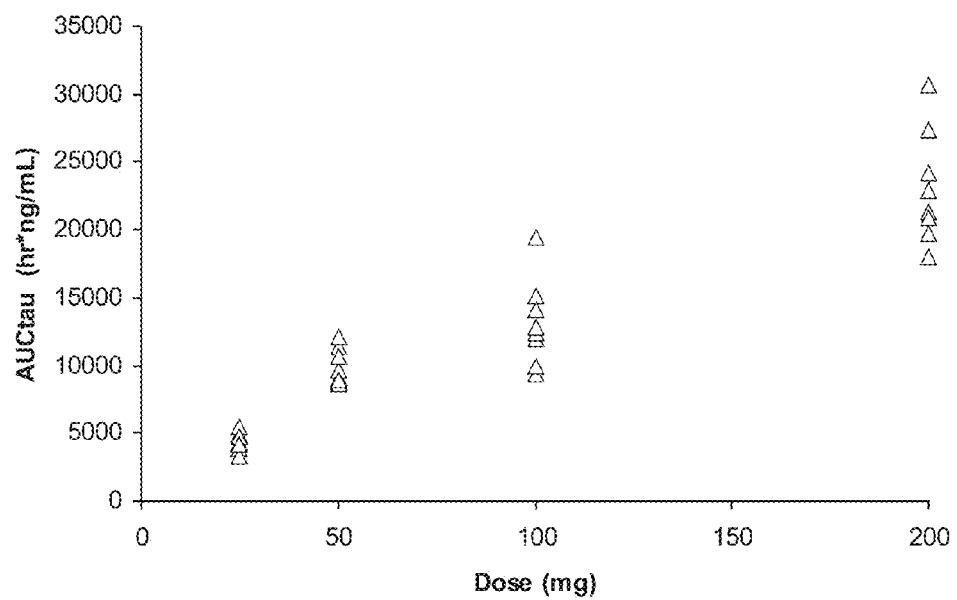

FIG. 12B provides a dose-proportionality assessment of Compound I at steady state ($AUC_{0-24h}$ on Day 14 vs. Dose (N=8)).

6. DETAILED DESCRIPTION

6.1 Definitions

To facilitate understanding of the disclosure set forth herein, a number of terms are defined below.

Generally, the nomenclature used herein and the laboratory procedures in organic chemistry, medicinal chemistry, pharmacology, and pharmaceutical sciences described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human. In one embodiment, a "subject" is a human in need of treatment of a disease provided herein.

The terms "treat" "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "improving" as used herein in connection with scar formation or keloid formation, means reducing the size, visibility or noticeability of the scar or keloid or generally improving the appearance of the scar or keloid.

The term "therapeutically effective amount" is meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable excipient" refers to a pharmaceutically-acceptable material, composition, or vehicle, such as a liquid or solid filler, diluent, solvent, or encapsulating material. In one embodiment, each excipient is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy*, 21st ed.; Lippincott Williams & Wilkins: Philadelphia, Pa., 2005; *Handbook of Pharmaceutical Excipients*, 6th ed.; Rowe et al., Eds.; The Pharmaceutical Press and the American Pharmaceutical Association: 2009; *Handbook of Pharmaceutical Additives*, 3rd ed.; Ash and Ash Eds.; Gower Publishing Company: 2007; *Pharmaceutical Preformulation and Formulation*, 2nd ed.; Gibson Ed.; CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

The term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, bishydrate, trihydrate, tetrahydrate, and pentahydrate.

The term "isomer" refers to any geometric form of a compound including, for example, conformers, rotamers, stereoisomers, and mixtures thereof. The term "stereoisomer" includes the presence of stereogenic centers, such as a carbon bearing four different substituents, axial asymmetry such as about a bond, planar asymmetry, and mixtures thereof. Stereoisomers encompasses enantiomers, diastereomers, epimers, racemates, and meso compounds having internal planes of symmetry. The term "isomer" also includes geometric isomers about unsaturated carbon-carbon, unsaturated carbon-heteroatom and unsaturated heteroatom-heteroatom bonds. Such geometric isomers include all cis, trans, syn, anti, entgegen (E), and zusammen (Z) isomers as well as mixtures thereof. The term "isomer" can also include rotamers, which are a form of conformational isomerism involving restricted rotation about a single bond. Rotamers can interconvert readily or can exist in a stable isolable form depending on the energy barrier to rotation.

The term "isomer" also encompasses tautomeric isomers. Tautomers can include prototropic tautomers, that is, tautomers related by hydrogen or proton migration with concomitant migration of an unsaturation, including, without limitation, amine-imine tautomers. A tautomer form can exist in a single, stable pure state or as a tautomeric mixture in any ratio. Tautomeric forms can be interconverted, for example, by general acid-base catalysis, in protic solvents, by application of heat, or any mixture of these methods. Providing conditions suitable for tautomeric interconversion can allow for the isolation of a predominant thermodynamically favored tautomeric form. Tautomeric forms can be influenced by the presence or absence of solvents.

The term "optically active" refers to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of one enantiomer and about 5% or less of the other enantiomer based on the total weight of the racemate in question.

In describing an optically active compound, the prefixes R and S are used to denote the absolute configuration of the molecule about its chiral center(s) according to Cahn-Ingold-Prelog priority rules known to one skilled in the art.

The term "isotopologue" refers to any form of a compound in which at least one atom of natural isotopic abundance is replaced with an isotopically enriched form that differs from natural abundance. An isotopologue can be based on replacement of hydrogen for deuterium and/or tritium. Similarly, naturally abundant $^{12}C$ can be replaced with $^{13}C$ or $^{14}C$, naturally abundant $^{14}N$ can be replaced with $^{15}N$, and naturally abundant $^{16}O$ with $^{17}O$ or $^{18}O$, and so on in any combination. Other isotopologues can be based on isotopic enrichment of fluorine, sulfur, phosphorus, boron, and the like. Isotopologues can include replacing any number atoms within the compound with isotopically enriched forms. The isotopic enrichment can be effected to any degree, including, 1, 5, 10, 15, 20, 25, 30, 35, 40, 45, 50, 60, 70, 80, 90, 95, and 99, and 100% enrichment, including any value in between and fractions thereof 6.2 Diaminopurine Compounds Compound I includes 4-((9-((3S)-tetrahydro-3-furanyl)-8-((2,4,6-trifluorophenyl)amino)-9H-purin-2-yl)amino)-trans-cyclohexanol, which has the structure

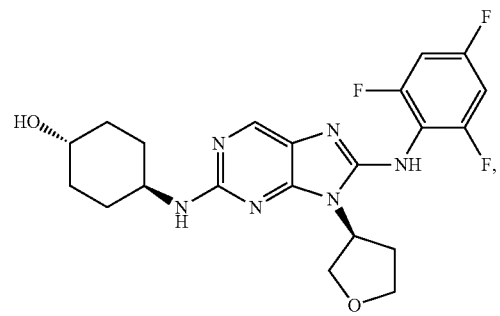 [SMILES: O[C@H]1CC[C@H](Nc2ncc3nc(Nc4c(F)cc(F)cc4F)n([C@H]4CCOC4)c3n2)CC1]

and pharmaceutically acceptable salts, solvates, isomers, isotopologues, tautomers and racemic mixtures thereof, which are to be used in the formulations and methods provided herein. As used herein, the term "Compound I" is intended to include 4-((9-((3S)-tetrahydro-3-furanyl)-8-((2,4,6-trifluorophenyl)amino)-9H-purin-2-yl)amino)-trans-cyclohexanol and pharmaceutically acceptable salts, solvates, isomers, isotopologues, tautomers and racemic mixtures thereof. In one embodiment, the isomer is an enantiomer.

In certain embodiments, Compound I is useful in the formulations and methods provided herein.

In some embodiments, Compound I can exist in two tautomeric forms shown below as tautomer T1 and tautomer T2.

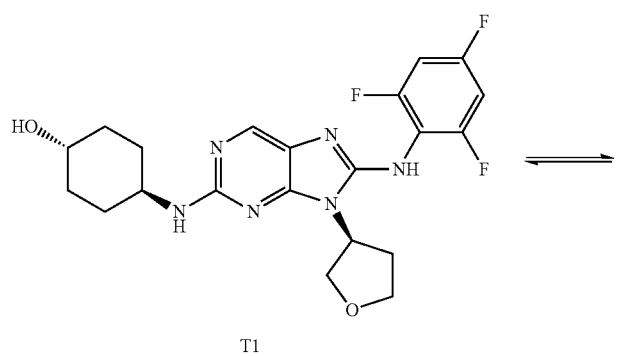

T1

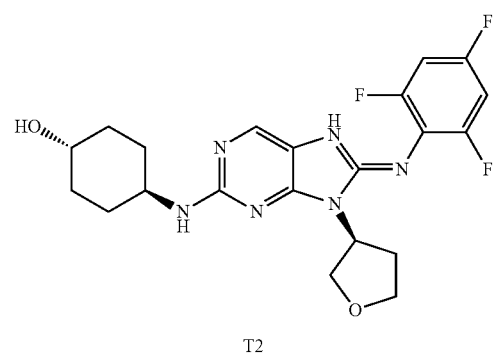

T2

Accordingly, in one embodiment, provided herein is a compound having formula T2 and pharmaceutically acceptable salts, solvates, isomers, isotopologues, tautomers and racemic mixtures thereof.

In some embodiments tautomer T2 is the predominant tautomer. In some such embodiments, tautomer T2 can be provided in substantially pure form as a solid. Without being bound by theory it has been indicated that tautomer T2 is a thermodynamically favored tautomer. In some embodiments, tautomer T1 is the predominant tautomer in a solid. In some such embodiments, tautomer T1 can be prepared as a kinetically stable tautomer, in the absence of conditions suitable for tautomerization. In still further embodiments, a solid form of Compound I can be provided as a mixture of tautomers T1 and T2 in any ratio in accordance with conditions suitable to control the rate of tautomerization, including the presence of polar protic solvents, general acid-base catalysis, by heating (especially in polar aprotic solvents), or mixtures of these conditions. Any of the aforementioned pure or mixed tautomeric forms can exists in crystalline or non-crystalline (amorphous) forms, as further described below. In some embodiments, tautomer T1 or T2 can be provided as the predominant form in solution as well, while in other embodiments, a solution can have both tautomers present in various ratios.

Where mixtures of tautomers are present in solid or solution form, the ratio of T2 to T1 can be in a range from between about 100:1 to about 1:100. In certain embodiments, the ratio of T2 to T1 is about 1:1.

In some embodiments, tautomer T2 can further exist in a Z or E configuration as shown below. In certain embodiments, the equilibrium is shifted to the E form.

Compound I can be prepared according to the methods described in U.S. Pat. Nos. 7,521,446, 7,723,340, and 7,759,342; U.S. Pat. App. Pub. Nos. 2009/275564, 2009/312320, and 2010/249066; and International Pub. Nos. WO 2006/076595 and WO 2007/127382, the disclosure of each of which is incorporated herein by reference in its entirety.

Free base Compound I in crystalline Forms A and B can be prepared according to the methods described in U.S. Pat. App. Pub. No. 2009/0048275, the disclosure of which is incorporated herein by reference in its entirety. Certain characteristics of Forms A and B are described in U.S. Pat. App. Pub. No. 2009/0048275 at page 5, paragraph [0071] to page 6, paragraph [0077], including the figures referenced therein, all of which is incorporated by reference herein in its entirety.

In one embodiment, Compound I is a free base. In certain embodiments, the free base is a solid. In certain embodiments, the free base is an amorphous solid. In yet another embodiment, the free base is crystalline. In certain embodiments, the free base is in crystalline Form A. In certain embodiments, the free base is in crystalline Form B.

In some embodiments, the amorphous solid can include tautomer E-T2. In some embodiments, the amorphous solid consists essentially of tautomer E-T2. In some such embodiments, small amounts of Z-T2 and T1 can be present. In some embodiments, the amorphous solid can include tautomer T1. In some embodiments, the amorphous solid can include mixtures of tautomers E-T2 and T1. In some embodiments, the amorphous solid can include tautomer Z-T2. In some embodiments, the amorphous solid can include mixtures of tautomers E-T2 and Z-T2. In some embodiments, the amorphous solid can include mixtures of E-T2, Z-T2 and T1.

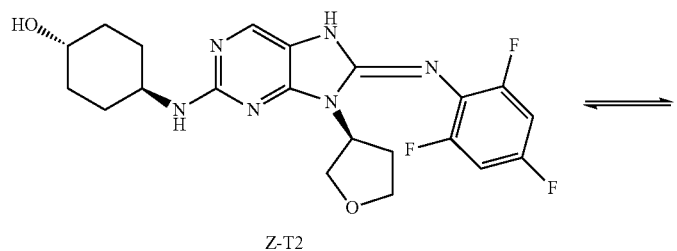

Z-T2

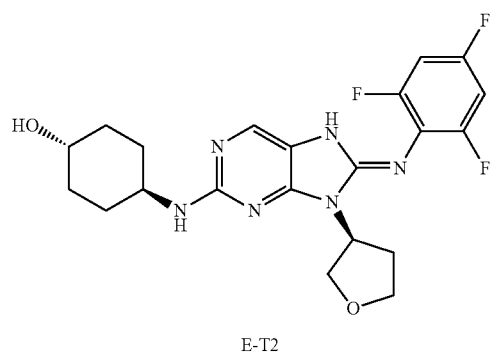

E-T2

Compound I can be prepared, isolated, or obtained by any method known to one skilled in the art. For an example, In some embodiments, the crystalline Form A can include tautomer E-T2. In some embodiments, the crystalline Form A consists essentially of tautomer E-T2. In some such embodiments, small amounts of Z-T2 and T1 can be present. In some embodiments, the crystalline Form A can include tautomer T1. In some embodiments, the crystalline Form A can include mixtures of tautomers E-T2 and T1. In some embodiments, the crystalline Form A can include tautomer Z-T2. In some embodiments, the crystalline Form A can include mixtures of tautomers E-T2 and Z-T2. In some embodiments, the crystalline Form A can include mixtures of E-T2, Z-T2 and T1.

In some embodiments, the crystalline Form B can include tautomer E-T2. In some embodiments, the crystalline Form B consists essentially of tautomer E-T2. In some such embodiments, small amounts of Z-T2 and T1 can be present. In some embodiments, the crystalline Form B can include tautomer T1. In some embodiments, the crystalline Form B can include mixtures of tautomers E-T2 and T1. In some embodiments, the crystalline Form B can include tautomer Z-T2. In some embodiments, the crystalline Form B can include mixtures of tautomers E-T2 and Z-T2. In some embodiments, the crystalline Form B can include mixtures of E-T2, Z-T2 and T1.

In certain embodiments, Form A of the free base of Compound I is characterized by XRPD peaks located at one or more of the following approximate positions: 10.0, 12.4, 12.8, 15.2, 16.0, 16.3, 17.7, 18.5, 18.9, 19.4, 20.0, 20.6, 20.9, 21.6, 22.7, 23.2, 26.1, 26.6, 26.8, 25.7, 26.0, 26.4, 26.6, 27.2, 27.9, 30.2, 30.8, 31.0, 31.5 degrees 2θ. In particular embodiments, Form A of the free base of Compound I is characterized by XRPD peaks located at one, two, three, four, five or six of the following approximate positions: 12.4, 16.0, 17.7, 18.5, 23.2, 24.1 degrees 2θ. In certain embodiments, Form A of the free base of Compound I has an XRPD pattern comprising peaks at approximately 12.4, 16.0 and 18.5 degrees 2θ. In certain embodiments, Form A of the free base of Compound I has an XRPD pattern further comprising peaks at approximately 17.7, 23.2 and 24.1 degrees 2θ.

In some embodiments, Form A of the free base of a compound having the chemical formula $C_{21}H_{23}F_3N_6O_2$ is characterized by XRPD peaks located at one or more of the following approximate positions: 10.0, 12.4, 12.8, 15.2, 16.0, 16.3, 17.7, 18.5, 18.9, 19.4, 20.0, 20.6, 20.9, 21.6, 22.7, 23.2, 26.1, 26.6, 26.8, 25.7, 26.0, 26.4, 26.6, 27.2, 27.9, 30.2, 30.8, 31.0, 31.5 degrees 2θ. In particular embodiments, Form A of the free base of a compound having the chemical formula $C_{21}H_{23}F_3N_6O_2$ is characterized by XRPD peaks located at one, two, three, four, five or six of the following approximate positions: 12.4, 16.0, 17.7, 18.5, 23.2, 24.1 degrees 2θ. In certain embodiments, Form A of the free base of a compound having the chemical formula $C_{21}H_{23}F_3N_6O_2$ has an XRPD pattern comprising peaks at approximately 12.4, 16.0 and 18.5 degrees 2θ. In certain embodiments, Form A of the free base of a compound having the chemical formula $C_{21}H_{23}F_3N_6O_2$ has an XRPD pattern further comprising peaks at approximately 17.7, 23.2 and 24.1 degrees 2θ.

In certain embodiments, Form A of the free base of tautomer T2 is characterized by XRPD peaks located at one or more of the following approximate positions: 10.0, 12.4, 12.8, 15.2, 16.0, 16.3, 17.7, 18.5, 18.9, 19.4, 20.0, 20.6, 20.9, 21.6, 22.7, 23.2, 26.1, 26.6, 26.8, 25.7, 26.0, 26.4, 26.6, 27.2, 27.9, 30.2, 30.8, 31.0, 31.5 degrees 2θ. In particular embodiments, Form A of the free base of tautomer T2 is characterized by XRPD peaks located at one, two, three, four, five or six of the following approximate positions: 12.4, 16.0, 17.7, 18.5, 23.2, 24.1 degrees 2θ. In certain embodiments, Form A of the free base of tautomer T2 has an XRPD pattern comprising peaks at approximately 12.4, 16.0 and 18.5 degrees 2θ. In certain embodiments, Form A of the free base of tautomer T2 has an XRPD pattern further comprising peaks at approximately 17.7, 23.2 and 24.1 degrees 2θ.

In some embodiments, a formulation provided herein can include crystal Form A having the aforementioned XRPD peaks and further other crystal forms, such as minor amounts of Form B, crystalline hydrates, other solvates, and mixtures thereof. In some embodiments, crystal Form A having the aforementioned XRPD peaks can include the amorphous solid form as well.

In another embodiment, Compound I is a pharmaceutically acceptable solvate of the free base. In one embodiment, the solvate is a hydrate, such as a bis-hydrate. In another embodiment, the hydrate is in a crystalline form. A hydrate of the free base Compound I in crystalline form can be prepared according to the methods described in U.S. Pat. App. Pub. No. 2009/0048275, the disclosure of which is incorporated herein by reference in its entirety. In certain embodiments, the hydrate of the free base Compound I in crystalline form includes the tautomer T2.

In yet another embodiment, Compound I is a pharmaceutically acceptable salt, which includes, but is not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

In certain embodiments, the pharmaceutically acceptable salt of Compound I is a hydrochloride salt. In certain embodiments, the pharmaceutically acceptable salt of Compound I is a mono-hydrochloride salt. In certain embodiments, the pharmaceutically acceptable salt of Compound I is a hydrochloride salt in a crystalline form. In certain embodiments, the pharmaceutically acceptable salt of Compound I is a hydrochloride salt in crystalline Form A. The hydrochloride salt of Compound I in crystalline form can be prepared according to the methods described in U.S. Pat. App. Pub. No. 2009/0048275, the disclosure of which is incorporated herein by reference in its entirety.

In certain embodiments, the pharmaceutically acceptable salt of Compound I is a hydrobromide salt. In certain embodiments, the pharmaceutically acceptable salt of Compound I is a mono-hydrobromide salt. In certain embodiments, the pharmaceutically acceptable salt of Compound I is a hydrobromide salt in a crystalline form. In certain embodiments, the pharmaceutically acceptable salt of Compound I is a hydrobromide salt in crystalline Form A. The hydrobromide salt of Compound I in crystalline form can be prepared according to the methods described in U.S. Pat. App. Pub. No. 2009/0048275, the disclosure of which is incorporated herein by reference in its entirety.

In certain embodiments, the pharmaceutically acceptable salt of Compound I is a sulfuric acid salt. In certain embodiments, the pharmaceutically acceptable salt of Compound I is a sulfuric acid salt in a crystalline form. In certain embodiments, the pharmaceutically acceptable salt of Compound I is a sulfuric acid salt in crystalline Form A. The sulfuric acid salt of Compound I in crystalline form can be prepared according to the methods described in U.S. Pat. App. Pub. No. 2009/0048275, the disclosure of which is incorporated herein by reference in its entirety.

In certain embodiments, Compound I is provided as an isotopologue. Isotopologues of Compound I can be prepared according to the methods described in International Pub. No. WO 2011/071491, the disclosure of which is incorporated herein by reference in its entirety. Specific isotopologues of Compound I include those at paragraphs [0038]-[0054] of International Pub. No. WO 2011/071491.

6.3 Pharmaceutical Formulations

It has been surprisingly and unexpectedly found that Compound I is teratogenic to rats and rabbits. Accordingly, in certain embodiments, the pharmaceutical formulations provided herein are formulated as capsules or a coated tablet to minimize the risk of unintended exposure of a person to Compound I. In certain embodiments, the formulations reduce or minimize the topical or mucosal exposure of a person to Compound I. Without being limited by theory, it is believed that the formulations provided herein are suitable for achieving an effective bioavailability, while also protecting the patient and health care provider by reducing unintended exposure to Compound I.

In addition, it has further been surprisingly and unexpectedly found that the type and amount of certain excipients can provide desirable physical and chemical properties of the formulations provided herein, such as hardness, blend flow or flowability, dissolution rate, sticking, filming and capping. Many of these properties can affect the overall manufacturing process.

In one embodiment, provided herein are pharmaceutical formulations, which comprise Compound I, and one or more excipients. In a specific embodiment, the pharmaceutical formulation is a capsule.

In certain embodiments, the excipient is a binder, diluent, disintegrant, lubricant, glidant, or mixture thereof.

Illustrative binders include, but are not limited to, microcrystalline cellulose (e.g., silicified microcrystalline cellulose) and modified cellulose (for example hydroxypropyl methylcellulose).

Illustrative diluents include, but are not limited to, ammonium alginate, calcium carbonate, calcium phosphate, calcium sulfate, cellulose, cellulose acetate, silicified cellulose, dextrate, dextrin, dextrose, erythritol, fructose, glyceryl palmitostearate, kaolin, lactitol, lactose, magnesium carbonate, magnesium oxide, malitol, maltodextrin, maltose, mannitol, simethicone, sorbitol, starch, sucrose, sugar, talc, trehalose, xylitol, or a combination of any two or more thereof.

Illustrative disintegrants include, but are not limited to, alginic acid, calcium alginate, carboxymethyl cellulose calcium, carboxymethyl cellulose sodium, cellulose, chitosan, croscarmellose sodium, crospovidone, guar gum, hydroxypropyl cellulose, hydroxypropyl starch, magnesium/aluminum silicate, methyl cellulose, polacrilin potassium, povidone, sodium starch glycolate, starch, or a combination of any two or more thereof.

Illustrative lubricants include, but are not limited to, magnesium stearate, stearic acid (stearin), hydrogenated oil and sodium stearyl fumarate.

Illustrative glidants include, but are not limited to, aluminum oxide, calcium phosphate, calcium silicate, calcium stearate, cellulose, glyceryl behenate, glyceryl monostearate, magnesium oxide, magnesium silicate, magnesium stearate, magnesium trisilicate, silicon dioxide (e.g., colloidal silicon dioxide), sodium benzoate, sodium stearyl fumarate, starch, stearic acid, talc, or a combination of any two or more thereof.

In certain embodiments, the excipient is a binder, including those as described herein. In certain embodiments, the binder is silicified microcrystalline cellulose.

In certain embodiments, the excipient is a diluent, including those as described herein. In certain embodiments, the diluent is lactose.

In certain embodiments, the excipient is a disintegrant, including those as described herein. In certain embodiments, the disintegrant is croscarmellose sodium.

In certain embodiments, the excipient is a lubricant, including those as described herein. In certain embodiments, the lubricant is magnesium stearate.

In certain embodiments, the excipient is a glidant, including those as described herein.

In certain embodiments, the excipient is silicified microcrystalline cellulose (e.g., PROSOLV SMCC 50®), microcrystalline cellulose (e.g., AVICEL® PH-102, AVICEL® PH-105, or AVICEL® PH-302), lactose (e.g., anhydrous lactose or SUPER TAB® 21AN), starch (e.g., pegelatinized maize starch or STARCH 1500®), mannitol (e.g., MANNOGEM™ EZ spray dried mannitol), croscarmellose sodium (e.g., AC-DI-SOL®), sodium starch glycolate (e.g., EXPLOTAB®), silicon dioxide (e.g., colloidal silicon dioxide, untreated fumed silica, or Cab-O-Sil® M-5P), magnesium stearate (e.g., HYQUAL® vegetable grade), sodium stearyl fumarate (e.g., PRUV®), or a mixture thereof.

In certain embodiments, the excipient is silicified microcrystalline cellulose, microcrystalline cellulose, lactose, croscarmellose sodium, magnesium stearate, or a mixture thereof. In certain embodiments, the excipient is silicified microcrystalline cellulose. In certain embodiments, the excipient is lactose. In certain embodiments, the excipient is croscarmellose sodium. In certain embodiments, the excipient is magnesium stearate.

In another embodiment, the pharmaceutical formulations further comprise one or more additional excipients. In certain embodiments, the additional excipients are each independently a binder, diluent, disintegrant, lubricant, glidant, or mixture thereof. In certain embodiments, the additional excipients are each independently silicified microcrystalline cellulose (e.g., PROSOLV SMCC 50®), microcrystalline cellulose (e.g., AVICEL® PH-102, AVICEL® PH-105, or AVICEL® PH-302), lactose (e.g., anhydrous lactose or SUPER TAB® 21AN), starch (e.g., pegelatinized maize starch or STARCH 1500®), mannitol (e.g., MANNOGEM™ EZ spray dried mannitol), croscarmellose sodium (e.g., AC-DI-SOL®), sodium starch glycolate (e.g., EXPLOTAB®), solicon dioxide (e.g., colloidal silicon dioxide, untreated fumed silica, or Cab-O-Sil® M-5P), magnesium stearate (e.g., HYQUAL® vegetable source), sodium stearyl fumarate (e.g., PRUV®), or a mixture thereof. In certain embodiments, the additional excipients are each independently silicified microcrystalline cellulose, lactose, croscarmellose sodium, magnesium stearate, or a mixture thereof.

In yet another embodiment, provided herein are pharmaceutical formulations comprising Compound I, and silicified microcrystalline cellulose. In one embodiment, the pharmaceutical formulations further comprise one or more additional excipients. In another embodiment, the pharmaceutical formulations further comprise a binder. In yet another embodiment, the pharmaceutical formulations further comprise a diluent. In yet another embodiment, the pharmaceutical formulations further comprise a disintegrant. In yet another embodiment, the pharmaceutical formulations further comprise a lubricant. In yet another embodiment, the pharmaceutical formulations further comprise glidant. In one embodiment, the pharmaceutical formulations further comprise lactose. In yet another embodiment, the pharmaceutical formulations further comprise croscarmellose sodium. In yet another embodiment, the pharmaceutical formulations further comprise magnesium stearate.

In yet another embodiment, provided herein are pharmaceutical formulations comprising Compound I, and a binder and a diluent.

In yet another embodiment, provided herein are pharmaceutical formulations comprising Compound I, and a binder and a disintegrant.

In yet another embodiment, provided herein are pharmaceutical formulations comprising Compound I, and a binder and a lubricant.

In yet another embodiment, provided herein are pharmaceutical formulations comprising Compound I, and a binder, a diluent, and a disintegrant.

In yet another embodiment, provided herein are pharmaceutical formulations comprising Compound I, and a binder, a diluent, and a lubricant.

In yet another embodiment, provided herein are pharmaceutical formulations comprising Compound I, and a binder, a disintegrant, and a lubricant.

In yet another embodiment, provided herein are pharmaceutical formulations comprising Compound I, and a binder, a diluent, a disintegrant, and a lubricant.

In yet another embodiment, provided herein are pharmaceutical formulations comprising Compound I, and silicified microcrystalline cellulose and a diluent.

In yet another embodiment, provided herein are pharmaceutical formulations comprising Compound I, and silicified microcrystalline cellulose and a disintegrant.

In yet another embodiment, provided herein are pharmaceutical formulations comprising Compound I, and silicified microcrystalline cellulose and a lubricant.

In yet another embodiment, provided herein are pharmaceutical formulations comprising Compound I, and silicified microcrystalline cellulose, a diluent, and a disintegrant.

In yet another embodiment, provided herein are pharmaceutical formulations comprising Compound I, and silicified microcrystalline cellulose, a diluent, and a lubricant.

In yet another embodiment, provided herein are pharmaceutical formulations comprising Compound I, and silicified microcrystalline cellulose, a disintegrant, and a lubricant.

In yet another embodiment, provided herein are pharmaceutical formulations comprising Compound I, and silicified microcrystalline cellulose, a diluent, a disintegrant, and a lubricant.

In yet another embodiment, provided herein are pharmaceutical formulations comprising Compound I, and silicified microcrystalline cellulose and lactose.

In yet another embodiment, provided herein are pharmaceutical formulations comprising Compound I, and silicified microcrystalline cellulose and croscarmellose sodium.

In yet another embodiment, provided herein are pharmaceutical formulations comprising Compound I, and silicified microcrystalline cellulose and magnesium stearate.

In yet another embodiment, provided herein are pharmaceutical formulations comprising Compound I, and silicified microcrystalline cellulose, lactose, and croscarmellose sodium.

In yet another embodiment, provided herein are pharmaceutical formulations comprising Compound I, and silicified microcrystalline cellulose, lactose, and magnesium stearate.

In yet another embodiment, provided herein are pharmaceutical formulations comprising Compound I, and silicified microcrystalline cellulose, croscarmellose sodium, and magnesium stearate.

In yet another embodiment, provided herein are pharmaceutical formulations comprising Compound I, and silicified microcrystalline cellulose, lactose, croscarmellose sodium, and magnesium stearate.

In yet another embodiment, provided herein are pharmaceutical formulations comprising Compound I, and about 30-35% w/w, about 35-45% w/w, about 45-60% w/w, about 50-60% w/w, about 50-55% w/w or about 34% w/w or about 53% w/w microcrystalline cellulose.

In yet another embodiment, provided herein are pharmaceutical formulations comprising Compound I, and about 0.1-0.5% w/w, about 0.5%-1.0% w/w, about 0.5% w/w, or about 1.0% w/w of a lubricant, such as magnesium stearate.

In yet another embodiment, provided herein are pharmaceutical formulations comprising Compound I, in combination with a microcrystalline cellulose, such as AVICEL® PH-102, AVICEL® PH-105 or AVICEL® PH-302) and a starch, such as Starch 1500® (a pregelatinzed maize starch).

In yet another embodiment, provided herein are pharmaceutical formulations comprising Compound I, and about 10-20% w/w, about 10-15% w/w, about 15-20% w/w, about 20-40% w/w, about 40-60% w/w, about 50-60% w/w, about 55-60% w/w, about 56% w/w lactose, about 18% w/w or about 11.5% w/w. In one embodiment, the lactose is anhydrous.

In yet another embodiment, provided herein are pharmaceutical formulations comprising Compound I, in combination with microcrystalline cellulose, lactose and Cab-O-Sil®.

In yet another embodiment, provided herein are pharmaceutical formulations comprising Compound I, in combination with AVICEL® PH 105 and/or AVICEL® PH 302.

In certain embodiments, the material comprising Compound I and one or more excipients is a dry blend formulation. In certain embodiments, the dry blend formulation is used to fill a capsule. In another embodiment, Compound I and excipients are used separately to fill a capsule. In other embodiments, the dry blend formulation is used to form a coated tablet.

In certain embodiments, tablets comprising Compound I provided herein have a hardness of about 8-12 kP (e.g., for 25 mg or 100 mg tablets) or a hardness of about 16-20 kP (e.g. for 400 mg tablets).

In certain embodiments, tablets or capsules comprising Compound I provided herein have a dissolution profile wherein about 100% of Compound I is released in about 5 minutes, about 10 minutes, about 15 minutes, about 20 minutes, about 30 minutes, about 45 minutes or about 60 minutes in water, diluted HCl aqueous solution or other aqueous buffer solutions of about pH 1 to about pH 8 (e.g., about pH 3), with or without surfactant, with a paddle speed of 50 rpm or 75 rpm, or with a basket speed of 100 rpm.

In a particular embodiment, the material comprising Compound I and one or more excipients is provided as a bulk product. In certain embodiments, the bulk product has a bulk density of about 0.40 to about 0.50 g/cc, such as 0.45 g/cc. In certain embodiments, the bulk product has a tap density of about 0.45 to about 0.55 g/cc, such as 0.49 g/cc.

In certain embodiments, the material comprising Compound I and one or more excipients has a Hauser's ratio (tapped density/bulk density) of about 1.0 to about 2.0, about 1.2 to about 1.8, about 1.4 to about 1.6 or about 1.5.

In certain embodiments, the material comprising Compound I and one or more excipients has a Carr's index ((tapped density−bulk density)*100/tapped density) of about 25 to about 35, about 26 to about 34, about 30 to about 33, about 31 or about 32.

In certain embodiments, the capsules provided herein have a fill weight of about 50 to about 150 mg, about 75 to about 125 mg, about 150 to about 250 mg, about 175 to about 225 mg, about 300 to about 500 mg, about 350 to about 450 mg, about 100 mg, about 200 mg, or about 400 mg.

In certain embodiments, the capsules provided herein have a capsule weight or gross fill weight of about 100 to about 200 mg, about 125 to about 175 mg, about 135 to about 145 mg, about 200 to about 300 mg, about 225 to about 275 mg, about 400 to about 600 mg, about 450 to about 550 mg, about 140 mg, about 260 mg, or about 500 mg.

In certain embodiments, the formulations provided herein contain Compound I and one or more of the materials provided herein and are characterized by one or more of the specific embodiments provided herein.

In one embodiment, the pharmaceutical formulations provided herein reduce or alleviate risks associated with contacting a teratogenic agent, such as abnormal development in embryos, congenital malformations or birth defects. In a particular embodiment, the capsule formulations provided herein reduce or alleviate risks associated with contacting a teratogenic agent relative to another formulation, such as a solid formulation (e.g., a tablet formulation).

The pharmaceutical formulations provided herein can be provided in a unit-dosage form or multiple-dosage form. A unit-dosage form, as used herein, refers to physically discrete unit suitable for administration to a human and animal subject, and packaged individually as is known in the art. Each unit-dose contains a predetermined quantity of (an) active ingredient(s) sufficient to produce the desired therapeutic effect, in association with the required pharmaceutical carriers or excipients. Examples of a unit-dosage form include an individually packaged capsule. A multiple-dosage form is a plurality of identical unit-dosage forms packaged in a single container to be administered in segregated unit-dosage form. Examples of a multiple-dosage form include a vial or bottle of capsules. In certain embodiments, the pharmaceutical formulations provided herein are formulated as a unit-dosage form.

In certain embodiments, the pharmaceutical formulations provided herein contain from about 1 to about 1,000 mg, from about 5 to about 800 mg, from about 5 to about 600 mg, from about 5 to about 500 mg, from about 10 to about 500 mg, from about 25 to about 500 mg, from about 5 to about 250 mg, from about 10 to about 250 mg, from about 25 to about 250 mg, from about 5 to about 200 mg, from about 10 to about 200 mg, or from about 25 to about 200 mg of Compound I. In certain embodiments, the pharmaceutical formulations provided herein contain about 5, about 10, about 20, about 25, about 30, about 40, about 50, about 60, about 70, about 80, about 90, about 100, about 110, about 120, about 130, about 140, about 150, about 160, about 170, about 180, about 190, about 200, about 250, about 300, about 350, or about 400 mg of Compound I. In certain embodiments, the unit-dosage form contains about 5, about 10, about 25, about 50, about 100, or about 200 mg of Compound I. In certain embodiments, the pharmaceutical formulations provided herein contain about 25, about 100, or about 200 mg of Compound I. In certain embodiments, the pharmaceutical formulations provided herein are formulated as a unit-dosage form.

In certain embodiments, the pharmaceutical formulations provided herein contain from about 1 to about 99%, from about 10 to about 90%, from about 20 to about 80%, from about 20 to about 70%, from about 10 to about 60%, from about 20 to about 60%, from about 10 to about 50%, or from about 25 to about 50% of Compound I by weight. In certain embodiments, the pharmaceutical formulations provided herein contain about 10, about 15, about 20, about 25, about 30, about 35, about 40, about 45, about 50, about 55, about 60, about 65, about 70, about 75, about 80, or about 90% of Compound I by weight. In certain embodiments, the pharmaceutical formulations provided herein contain about 25, about 30, about 35, about 40, about 45, about 50, about 55, or about 60% of Compound I by weight. In certain embodiments, the pharmaceutical formulations provided herein contain about 25% of Compound I by weight. In certain embodiments, the pharmaceutical formulations provided herein contain about 50% of Compound I by weight.

In certain embodiments, the pharmaceutical formulations provided herein contain from about 1 to about 500 mg, from about 5 to about 500 mg, from about 10 to about 400 mg, from about 10 to about 300 mg, from about 10 to about 250 mg, or from about 15 to about 250 mg of a binder. In certain embodiments, the pharmaceutical formulations provided herein contain about 10, about 15, about 20, about 25, about 30, about 40, about 50, about 60, about 70, about 80, about 90, about 100, about 110, about 120, about 130, about 140, about 150, about 160, about 170, about 180, about 190, about 200, about 210, about 225, about 250, about 300, about 350, or about 400 mg of a binder. In certain embodiments, the pharmaceutical formulations provided herein contain about 15, about 20, about 25, about 50, about 70, about 100, about 125, about 150, about 175, about 200, or about 210 mg of a binder. In certain embodiments, the pharmaceutical formulations provided herein contain about 15, about 20, about 50, about 70, about 160, or about 220 mg of a binder. In certain embodiments, the pharmaceutical formulations provided herein are formulated as a unit-dosage form.

In certain embodiments, the pharmaceutical formulations provided herein contain from about 10 to about 90%, from about 20 to about 80%, from about 20 to about 70%, from about 25 to about 70%, from about 25 to about 60%, or from about 30 to about 55% of a binder by weight. In certain embodiments, the pharmaceutical formulations provided herein contain about 10, about 15, about 20, about 25, about 30, about 35, about 40, about 45, about 50, about 55, about 60, about 65, about 70, about 75, about 80, about 85, or about 90% of a binder by weight. In certain embodiments, the pharmaceutical formulations provided herein contain about 30, about 31, about 32, about 33, about 34 or about 35% of a binder by weight. In certain embodiments, the pharmaceutical formulations provided herein contain about 50, about 51, about 52, about 53, about 54 or about 55% of a binder by weight.

In certain embodiments, the weight ratio of a binder over Compound I in the pharmaceutical formulations provided herein is ranging from about 0.1 to about 10, from about 0.25 to about 5, from about 0.5 to about 2.5, or from about 0.5 to about 2. In certain embodiments, the weight ratio of a binder over Compound I in the pharmaceutical formulations provided herein is about 0.5 about 0.6, about 0.7, about 0.8, about 0.9, about 1, about 1.1, about 1.2, about 1.3, about 1.4, about 1.5, about 1.6, about 1.7, about 1.8, about 1.9, about 2.0, about 2.1, about 2.2, about 2.3, about 2.4 or about 2.5.

In certain embodiments, the pharmaceutical formulations provided herein contain from about 1 to about 500 mg, from about 1 to about 250 mg, from about 1 to about 200 mg, from about 1 to about 100 mg, or from about 5 to about 100 mg of a diluent. In certain embodiments, the pharmaceutical formulations provided herein contain about 1, about 2, about 5, about 10, about 15, about 17, about 20, about 23, about 25, about 30, about 40, about 50, about 60, about 70, about 80, or about 100 mg of a diluent. In certain embodiments, the pharmaceutical formulations provided herein contain about 5, about 17, about 20, about 23, about 25, about 50, or about 75 mg of a diluent. In certain embodiments, the pharmaceutical formulations provided herein are formulated as a unit-dosage form.

In certain embodiments, the pharmaceutical formulations provided herein contain from about 1 to about 30%, from about 2 to about 25%, from about 5 to about 20%, or from about 10 to about 20% of a diluent by weight. In certain embodiments, the pharmaceutical formulations provided herein contain about 10, about 11, about 12, about 13, about 14, about 15, about 16, about 17, about 18, about 19, about 20, about 22, about 24, about 26, or about 30% of a diluent by weight. In certain embodiments, the pharmaceutical formulations provided herein contain about 10, about 11.5, about 15, about 17.5, or 20% of a diluent by weight.

In certain embodiments, the weight ratio of a diluent over Compound I in the pharmaceutical formulations provided herein is ranging from about 0.05 to about 5, from about 0.05 to about 0.15, from about 0.1 to about 2.5, from about 0.1 to about 1, or from about 0.2 to about 1%. In certain embodiments, the weight ratio of a diluent over Compound I in the pharmaceutical formulations provided herein is about 0.1, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, or about 1. In certain embodiments, the weight ratio of a diluent over Compound I in the pharmaceutical formulations provided herein is about 0.2, about 0.25, about 0.3, about 0.35, about 0.4, about 0.45, about 0.5, about 0.55, about 0.6, about 0.65, about 0.7, or about 0.75.

In certain embodiments, the pharmaceutical formulations provided herein contain from about 1 to about 100 mg, from about 1 to about 50 mg, from about 1 to about 25 mg, from about 1 to about 20 mg, or from about 1 to about 15 mg of a disintegrant. In certain embodiments, the pharmaceutical formulations provided herein contain about 1, about 1.5, about 2, about 3, about 4, about 5, about 6, about 7, about 8, about 9, about 10, about 11, about 12, about 13, about 14, about 15, about 17.5, or about 20 mg of a disintegrant. In certain embodiments, the pharmaceutical formulations provided herein contain about 1.5, about 3, about 6, or about 12 mg of a disintegrant. In certain embodiments, the pharmaceutical formulations provided herein are formulated as a unit-dosage form.

In certain embodiments, the pharmaceutical formulations provided herein contain from about 1 to about 10%, from about 1 to about 5%, or from about 2 to about 5% of a disintegrant by weight. In certain embodiments, the pharmaceutical formulations provided herein contain about 1, about 2, about 3, about 4, about 5, about 6, about 7, about 8, about 9, or about 10% of a disintegrant by weight. In certain embodiments, the pharmaceutical formulations provided herein contain about 1, about 2, about 3, about 4, or about 5% of a disintegrant by weight.

In certain embodiments, the weight ratio of a disintegrant over Compound I in the pharmaceutical formulations provided herein is ranging from about 0.01 to about 1, from about 0.01 to about 0.5, from about 0.02 to about 0.25, or from about 0.05 to about 0.15. In certain embodiments, the weight ratio of a disintegrant over Compound I in the pharmaceutical formulations provided herein is about 0.05, about 0.06, about 0.07, about 0.08, about 0.09, about 0.1, about 0.11, about 0.12, about 0.13, about 0.14, or about 0.15.

In certain embodiments, the pharmaceutical formulations provided herein contain from about 0.1 to about 10 mg, from about 0.2 to about 8 mg, or from about 0.5 to about 6 mg of a lubricant. In certain embodiments, the pharmaceutical formulations provided herein contain about 0.1, about 0.25, about 0.5, about 0.75, about 1, about 1.5, about 2, about 3, about 4, or about 5 mg of a lubricant. In certain embodiments, the pharmaceutical formulations provided herein contain about 0.75, about 1.5, about 2, about 3, about 4, or about 5 mg of a lubricant. In certain embodiments, the pharmaceutical formulations provided herein are formulated as a unit-dosage form.

In certain embodiments, the pharmaceutical formulations provided herein contain from about 0.1 to about 5%, from about 0.25 to about 2.5%, from about 0.5 to about 2%, or from about 0.5 to about 1.5% of a lubricant by weight. In certain embodiments, the pharmaceutical formulations provided herein contain about 0.5, about 0.75, about 1, about 1.25, about 1.3, about 1.5, or about 2% of a lubricant by weight.

In certain embodiments, the weight ratio of a lubricant over Compound I in the pharmaceutical formulations provided herein is ranging from about 0.005 to about 0.1, from about 0.01 to about 0.05, or from about 0.02 to about 0.05. In certain embodiments, the weight ratio of a lubricant over Compound I in the pharmaceutical formulations provided herein is about 0.01, about 0.015, about 0.02, about 0.025, about 0.03, about 0.04, or about 0.05.

In certain embodiments, the pharmaceutical formulations provided herein contain from about 1 to about 500 mg, from about 5 to about 500 mg, from about 10 to about 400 mg, from about 10 to about 300 mg, from about 10 to about 250 mg, or from about 15 to about 250 mg of silicified microcrystalline cellulose. In certain embodiments, the pharmaceutical formulations provided herein contain about 10, about 15, about 20, about 25, about 30, about 40, about 50, about 60, about 70, about 80, about 90, about 100, about 110, about 120, about 125, about 130, about 140, about 150, about 160, about 170, about 180, about 190, about 200, about 210, about 225, about 250, about 300, about 350, or about 400 mg of silicified microcrystalline cellulose. In certain embodiments, the pharmaceutical formulations provided herein contain about 15, about 20, about 25, about 50, about 70, about 100, about 125, about 150, about 175, about 200, or about 210 mg of silicified microcrystalline cellulose. In certain embodiments, the pharmaceutical formulations provided herein contain about 15, about 20, about 50, about 70, about 160, or about 220 mg of silicified microcrystalline cellulose. In certain embodiments, the pharmaceutical formulations provided herein are formulated as a unit-dosage form.

In certain embodiments, the pharmaceutical formulations provided herein contain from about 10 to about 90%, from about 20 to about 80%, from about 20 to about 70%, from about 25 to about 70%, from about 25 to about 60%, or from about 30 to about 55% of silicified microcrystalline cellulose by weight. In certain embodiments, the pharmaceutical formulations provided herein contain about 10, about 15, about 20, about 25, about 30, about 35, about 40, about 45, about 50, about 55, about 60, about 65, about 70, about 75, about 80, about 85, or about 90% of silicified microcrystalline cellulose by weight. In certain embodiments, the pharmaceutical formulations provided herein contain about 35 or about 55% of silicified microcrystalline cellulose by weight.

In certain embodiments, the weight ratio of silicified microcrystalline cellulose over Compound I in the pharmaceutical formulations provided herein is ranging from about 0.1 to about 10, from about 0.25 to about 5, from about 0.5 to about 2.5, or from about 0.5 to about 2. In certain embodiments, the weight ratio of silicified microcrystalline cellulose over Compound I in the pharmaceutical formulations provided herein is about 0.5 about 0.6, about 0.7, about 0.8, about 0.9, about 1, about 1.1, about 1.2, about 1.3, about 1.4, or about 1.5.

In certain embodiments, the pharmaceutical formulations provided herein contain from about 1 to about 500 mg, from about 1 to about 250 mg, from about 1 to about 200 mg, from about 1 to about 100 mg, or from about 5 to about 100 mg of lactose. In certain embodiments, the pharmaceutical formulations provided herein contain about 1, about 2, about 5, about 10, about 15, about 20, about 25, about 30, about 40, about 50, about 60, about 70, about 75 mg, about 80, or about 100 mg of lactose. In certain embodiments, the pharmaceutical formulations provided herein contain about 5, about 15, about 20, about 25, about 50, or about 75 mg of lactose. In certain embodiments, the pharmaceutical formulations provided herein are formulated as a unit-dosage form.

In certain embodiments, the pharmaceutical formulations provided herein contain from about 1 to about 30%, from about 2 to about 25%, from about 5 to about 20%, or from about 10 to about 20% of lactose by weight. In certain embodiments, the pharmaceutical formulations provided herein contain about 10, about 11, about 12, about 13, about 14, about 15, about 16, about 17, about 18, about 19, about 20, about 22, about 24, about 26, or about 30% of lactose by weight. In certain embodiments, the pharmaceutical formulations provided herein contain about 10, about 11.5, about 15, about 17.5, or 20% of lactose by weight.

In certain embodiments, the weight ratio of lactose over Compound I in the pharmaceutical formulations provided herein is ranging from about 0.05 to about 5, from about 0.1 to about 2.5, from about 0.1 to about 1, or from about 0.2 to about 1. In certain embodiments, the weight ratio of lactose over Compound I in the pharmaceutical formulations provided herein is about 0.1, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, or about 1. In certain embodiments, the weight ratio of lactose over Compound I in the pharmaceutical formulations provided herein is about 0.2, about 0.25, about 0.3, about 0.35, about 0.4, about 0.45, about 0.5, about 0.55, about 0.6, about 0.65, about 0.7, or about 0.75.

In certain embodiments, the pharmaceutical formulations provided herein contain from about 1 to about 100 mg, from about 1 to about 50 mg, from about 1 to about 25 mg, from about 1 to about 20 mg, or from about 1 to about 15 mg of croscarmellose sodium. In certain embodiments, the pharmaceutical formulations provided herein contain about 1, about 1.5, about 2, about 3, about 4, about 5, about 6, about 7, about 8, about 9, about 10, about 11, about 12, about 13, about 14, about 15, about 17.5, or about 20 mg of croscarmellose sodium. In certain embodiments, the pharmaceutical formulations provided herein contain contains about 1.5, about 3, about 6, or about 12 mg of croscarmellose sodium. In certain embodiments, the pharmaceutical formulations provided herein are formulated as a unit-dosage form.

In certain embodiments, the pharmaceutical formulations provided herein contain from about 1 to about 10%, from about 1 to about 5%, or from about 2 to about 5% of croscarmellose sodium by weight. In certain embodiments, the pharmaceutical formulations provided herein contain about 1, about 2, about 3, about 4, about 5, about 6, about 7, about 8, about 9, or about 10% of croscarmellose sodium by weight. In certain embodiments, the pharmaceutical formulations provided herein contain about 1, about 2, about 3, about 4, or about 5% of croscarmellose sodium by weight.

In certain embodiments, the weight ratio of croscarmellose sodium over Compound I in the pharmaceutical formulations provided herein is ranging from about 0.01 to about 1, from about 0.01 to about 0.5, from about 0.02 to about 0.25, or from about 0.05 to about 0.15%. In certain embodiments, the weight ratio of croscarmellose sodium over Compound I in the pharmaceutical formulations provided herein is about 0.05, about 0.06, about 0.07, about 0.08, about 0.09, about 0.1, about 0.11, about 0.12, about 0.13, about 0.14, or about 0.15.

In certain embodiments, the pharmaceutical formulations provided herein contain from about 0.1 to about 10 mg, from about 0.2 to about 8 mg, or from about 0.5 to about 6 mg of magnesium stearate. In certain embodiments, the pharmaceutical formulations provided herein contain about 0.1, about 0.25, about 0.5, about 0.75, about 1, about 1.5, about 2, about 3, about 4, or about 5 mg of magnesium stearate. In certain embodiments, the pharmaceutical formulations provided herein contain about 0.75, about 1.5, about 2, about 3, about 4, or about 5 mg of magnesium stearate. In certain embodiments, the pharmaceutical formulations provided herein are formulated as a unit-dosage form.

In certain embodiments, the pharmaceutical formulations provided herein contain from about 0.1 to about 5%, from about 0.25 to about 2.5%, from about 0.5 to about 2%, or from about 0.5 to about 1.5% of magnesium stearate by weight. In certain embodiments, the pharmaceutical formulations provided herein contain about 0.5, about 0.75, about 1, about 1.25, about 1.3, about 1.5, or about 2% of magnesium stearate by weight.

In certain embodiments, the weight ratio of magnesium stearate over Compound I in the pharmaceutical formulations provided herein is ranging from about 0.005 to about 0.1, from about 0.01 to about 0.05, or from about 0.02 to about 0.05. In certain embodiments, the weight ratio of magnesium stearate over Compound I in the pharmaceutical formulations provided herein is about 0.01, about 0.015, about 0.02, about 0.025, about 0.03, about 0.04, or about 0.05.

In one embodiment, provided herein is a unit-dosage form of the pharmaceutical formulations provided herein, comprising from about 5 to about 500 mg, about 10 to about 250 mg, about 10 to about 200 mg, about 25 to about 200 mg, about 25 to about 100 mg, about 50 to about 200 mg or about 50 to about 100 mg of Compound I, and from about 5 to about 500 mg, about 10 to about 250 mg, about 10 to about 150 mg, about 25 to about 100 mg, about 25 to about 75 mg or about 50 to about 100 mg of a binder. Such unit-dosage forms can further comprise from about 1 to about 100 mg, about 5 to about 200 mg, about 5 to about 50 mg, about 5 to about 25 mg or about 10 to about 50 mg, about 10 to about 40 mg or about 20 to about 40 mg of a diluent. Such unit-dosage forms can still further comprise from about 1 to about 100 mg, about 1 to about 50 mg, about 1 to abut 20 mg, about 1 to about 15 mg, about 1 to about 10 mg, about 5 to about 75 mg, about 5 to about 50 mg, about 5 to about 25 mg, about 5 to about 15 mg or about 5 to about 10 mg of a disintegrant. Such unit-dosage forms can still further comprise from about 0.1 to about 10 mg about 1 to about 10 mg, about 1 to about 5 mg or about 1 to about 3 mg of a lubricant.

In another embodiment, provided herein is a unit-dosage form of the pharmaceutical formulations provided herein, comprising from about 5 to about 500 mg, about 10 to about 250 mg, about 10 to about 200 mg, about 25 to about 200 mg, about 25 to about 100 mg, about 50 to about 200 mg or about 50 to about 100 mg of Compound I, and from about 5 to about 500 mg, about 10 to about 250 mg, about 10 to about 150 mg, about 25 to about 100 mg, about 25 to about 75 mg or about 50 to about 100 mg of silicified microcrystalline cellulose. Such unit-dosage forms can further comprise from about 1 to about 100 mg, about 5 to about 200 mg, about 5 to about 50 mg, about 5 to about 25 mg or about 10 to about 50 mg, about 10 to about 40 mg or about 20 to about 40 mg of a diluent. Such unit-dosage forms can still further comprise from about 1 to about 100 mg, about 1 to about 50 mg, about 1 to abut 20 mg, about 1 to about 15 mg, about 1 to about 10 mg, about 5 to about 75 mg, about 5 to about 50 mg, about 5 to about 25 mg, about 5 to about 15 mg or about 5 to about 10 mg of a disintegrant. Such unit-dosage forms can still further comprise from about 0.1 to about 10 mg about 1 to about 10 mg, about 1 to about 5 mg or about 1 to about 3 mg of a lubricant.

In yet another embodiment, provided herein is a unit-dosage form of the pharmaceutical formulations, comprising from about 5 to about 500 mg, about 10 to about 250 mg, about 10 to about 200 mg, about 25 to about 200 mg, about 25 to about 100 mg, about 50 to about 200 mg or about 50 to about 100 mg of Compound I, and from about 5 to about 500 mg, about 10 to about 250 mg, about 10 to about 150 mg, about 25 to about 100 mg, about 25 to about 75 mg or about 50 to about 100 mg of silicified microcrystalline cellulose. Such unit-dosage forms can further comprise from about 1 to about 100 mg, about 5 to about 200 mg, about 5 to about 50 mg, about 5 to about 25 mg or about 10 to about 50 mg, about 10 to about 40 mg or about 20 to about 40 mg of lactose. Such unit-dosage forms can still further comprise from about 1 to about 100 mg, about 1 to about 50 mg, about 1 to abut 20 mg, about 1 to about 15 mg, about 1 to about 10 mg, about 5 to about 75 mg, about 5 to about 50 mg, about 5 to about 25 mg, about 5 to about 15 mg or about 5 to about 10 mg of croscarmellose sodium. Such unit-dosage forms can still further comprise from about 0.1 to about 10 mg about 1 to about 10 mg, about 1 to about 5 mg or about 1 to about 3 mg of magnesium stearate.

In yet another embodiment, provided herein are pharmaceutical formulations, comprising from about 10 to about 60% by weight of Compound I, and from about 20 to about 70% by weight of silicified microcrystalline cellulose. Such pharmaceutical formulations can further comprise from about 1 to about 30% by weight of a diluent. Such pharmaceutical formulations can still further comprise from about 1 to about 10% by weight of a disintegrant. Such pharmaceutical formulations can still further comprise from about 0.1 to about 5% by weight of a lubricant.

In yet another embodiment, provided herein are pharmaceutical formulations, comprising from about 10 to about 60% by weight of Compound I, and from about 20 to about 70% by weight of silicified microcrystalline cellulose. Such pharmaceutical formulations can further comprise from about 1 to about 30% by weight of lactose. Such pharmaceutical formulations can still further comprise from about 1 to about 10% by weight of croscarmellose sodium. Such pharmaceutical formulations can still further comprise from about 0.1 to about 5% by weight of magnesium stearate.

In yet another embodiment, provided herein are pharmaceutical formulations, comprising from about 25 to about 50% by weight of Compound I, and from about 25 to about 60% by weight of a binder, from about 10 to about 20% by weight of a diluent, from about 1 to about 5% by weight of a disintegrant, and from about 0.5 to about 1.5% by weight of a lubricant.

In yet another embodiment, provided herein are pharmaceutical formulations, comprising from about 25 to about 50% by weight of Compound I, and from about 25 to about 60% by weight of silicified microcrystalline cellulose, from about 10 to about 20% by weight of a diluent, from about 1 to about 5% by weight of a disintegrant, and from about 0.5 to about 1.5% by weight of a lubricant.

In still another embodiment, provided herein are pharmaceutical formulations, comprising from about 25 to about 50% by weight of Compound I, and from about 25 to about 60% by weight of silicified microcrystalline cellulose, from about 10 to about 20% by weight of lactose, from about 1 to about 5% by weight of croscarmellose sodium, and from about 0.5 to about 1.5% by weight of magnesium stearate.

In certain embodiments, the pharmaceutical formulations provided herein are formulated as capsules. In certain embodiments, the pharmaceutical formulations provided herein are formulated as capsules of a capsule size of #000, #00, #0, #1, #2, #3, #4, or #5. In one embodiment, the capsule size is #000. In another embodiment, the capsule size is #00. In yet another embodiment, the capsule size is #0. In yet another embodiment, the capsule size is #1. In yet another embodiment, the capsule size is #2. In yet another embodiment, the capsule size is #3. In yet another embodiment, the capsule size is #4. In still another embodiment, the capsule size is #5. Without being limited by theory, it is thought that capsule size is important with respect to patient compliance. For example, the larger a capsule is, the more difficult it may be to swallow and the more likely it is for compliance to become an issue.

In certain embodiments, capsules contain from about 1 to about 1,000 mg, from about 5 to about 500 mg, from about 10 to about 400 mg, from about 20 to about 400 mg, from about 50 to about 400 mg, or from about 100 to about 400 mg of a pharmaceutical formulation provided herein. In certain embodiments, capsules contain about 5, about 10, about 20, about 50, about 100, about 200, about 400, or about 1,000 mg of a pharmaceutical formulation provided herein.

In certain embodiments, capsules each have a capsule size of #0 and contain about 400 mg of a pharmaceutical formulation provided herein. In certain embodiments, capsules each have a capsule size of #2 and contain about 200 mg of a pharmaceutical formulation provided herein. In certain embodiments, capsules each have a capsule size of #4 and contain from about 50 to about 100 mg of a pharmaceutical formulation provided herein. In certain embodiments, capsules each have a capsule size of #4 and contain about 50 or about 100 mg of a pharmaceutical formulation provided herein.

In certain embodiments, the pharmaceutical formulations provided herein are formulated as coated tablets. Illustrative coatings include, but are not limited to, Opadry II white, a non functional film coating system. Active core tablets can be coated in an appropriately sized coating pan to desired weight gain.

The dose of Compound I in a formulation provided herein to be administered to a patient is rather widely variable and can be subject to the judgment of a health-care practitioner. In general, Compound I can be administered one to four times a day in a dose of about 0.005 mg/kg of a patient's body weight to about 10 mg/kg of a patient's body weight in a patient, but the above dosage may be properly varied depending on the age, body weight and medical condition of the patient and the type of administration. In one embodiment, the dose is about 0.01 mg/kg of a patient's body weight to about 5 mg/kg of a patient's body weight, about 0.05 mg/kg of a patient's body weight to about 1 mg/kg of a patient's body weight, about 0.1 mg/kg of a patient's body weight to about 0.75 mg/kg of a patient's body weight or about 0.25 mg/kg of a patient's body weight to about 0.5 mg/kg of a patient's body weight. In one embodiment, one dose is given per day. In any given case, the amount of Compound I administered will depend on such factors as the solubility of the active component, the formulation used and the route of administration.

In another embodiment, provided herein are methods for the treatment or prevention of a disease or disorder comprising the administration of about 0.375 mg/day to about 750 mg/day, about 0.75 mg/day to about 375 mg/day, about 3.75 mg/day to about 75 mg/day, about 7.5 mg/day to about 55 mg/day or about 18 mg/day to about 37 mg/day of Compound I to a patient in need thereof.

In another embodiment, provided herein are methods for the treatment or prevention of a disease or disorder comprising the administration of about 1 mg/day to about 1200 mg/day, about 10 mg/day to about 1200 mg/day, about 100 mg/day to about 1200 mg/day, about 400 mg/day to about 1200 mg/day, about 600 mg/day to about 1200 mg/day, about 400 mg/day to about 800 mg/day or about 600 mg/day to about 800 mg/day of Compound I to a patient in need thereof. In a particular embodiment, the methods disclosed herein comprise the administration of 400 mg/day, 600 mg/day or 800 mg/day of Compound I to a patient in need thereof.

In another embodiment, provided herein are unit dosage formulations that comprise between about 1 mg and 200 mg, about 35 mg and about 1400 mg, about 125 mg and about 1000 mg, about 250 mg and about 1000 mg, or about 500 mg and about 1000 mg of Compound I. In one embodiment, the unit dosage formulation is about 50 mg or about 100 mg of Compound I.

In a particular embodiment, provided herein are unit dosage formulation comprising about 100 mg or 400 mg of Compound I.

In another embodiment, provided herein are unit dosage formulations that comprise 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of Compound I.

Pharmaceutical compositions provided herein can be administered once, twice, three, four or more times daily. In a particular embodiment, doses of 600 mg or less are administered as a once daily dose and doses of more than 600 mg are administered twice daily in an amount equal to one half of the total daily dose. In some embodiments, Compound I is administered in a dose of 25 mg once daily (ie. QD), in a dose of 25 mg twice daily (i.e. BID), 50 mg once daily (ie. QD), in a dose of 50 mg twice daily (i.e. BID), in a dose of 100 mg daily (i.e. QD), in a dose of 100 mg twice daily (i.e. BID), in a dose of 150 mg daily (i.e. QD), in a dose of 150 mg twice daily (i.e. BID), in a dose of 200 mg daily (i.e. QD), or in a dose of 200 mg twice daily (i.e. BID).

Pharmaceutical compositions provided herein can be administered orally for reasons of convenience. In one embodiment, when administered orally, a pharmaceutical composition provided herein is administered with a meal and water. In another embodiment, the pharmaceutical composition is dispersed in water or juice (e.g., apple juice or orange juice) and administered orally as a suspension.

In certain embodiments, the pharmaceutical compositions provided herein can be cyclically administered to a patient. Cycling therapy involves the administration of the pharmaceutical composition for a period of time, followed by a rest for a period of time and repeating this sequential administration. Cycling therapy can reduce the development of resistance to one or more of the therapies, avoid or reduce the side effects of one of the therapies and/or improves the efficacy of the treatment.

Consequently, in one specific embodiment, a pharmaceutical composition provided herein is administered daily in a single or divided doses in a four to six week cycle with a rest period of about a week or two weeks. The methods provided herein further allow the frequency, number and length of dosing cycles to be increased. Thus, in another specific embodiment, the methods provided herein encompasses the administration of a pharmaceutical composition provided herein for more cycles than are typical when it is administered alone.

In one embodiment, a pharmaceutical composition provided herein is administered daily and continuously for three or four weeks at a dose of from about 10 to about 200 mg per day followed by a break of one or two weeks. In another embodiment, a pharmaceutical composition provided herein is administered daily and continuously for three or four weeks at a dose of from about 0.1 to 5 mg per day followed by a break of one or two weeks. In a particular embodiment, a pharmaceutical composition provided herein is administered in an amount of about 5, 10, 25 or 50 mg/day, preferably in an amount of about 25 mg/day for three to four weeks, followed by one or two weeks of rest in a four or six week cycle.

6.4 Methods of Use

In certain embodiments, formulations provided herein are useful to treat, prevent, and/or manage a disease in a subject. In certain embodiments, formulations provided herein are useful to treat, prevent, and/or manage a disease associated with a protein kinase, including those involved in cancer, inflammatory conditions, immunological conditions, neurodegenerative diseases, cardiovascular diseases, metabolic conditions, insulin resistance, diabetes, fibrotic diseases, and disorders caused, induced or exacerbated by ozone, cold or exercise.

Provided herein are many uses of formulations provided herein, including the treatment or prevention of those diseases set forth herein, as well as those described in U.S. Pat. Nos. 7,521,446, 7,723,340 and 7,759,342; U.S. Pat. App. Pub. Nos. 2009/275564, 2009/312320, 2010/249066, and 2009/0048275; and International Pub. Nos. WO 2006/076595, WO 2007/127382 and WO 2008/057252; the disclosure of each of which is incorporated herein by reference in its entirety.

In certain embodiments, autoimmune conditions that formulations provided herein are useful for treating or preventing include, but are not limited to, rheumatoid arthritis, rheumatoid spondylitis, osteoarthritis, multiple sclerosis, lupus (including cutaneous lupus erythematosus and discoid lupus erythematosus, such as recalcitrant discoid lupus erythematosus), inflammatory bowel disease, ulcerative colitis, Crohn's disease, myasthenia gravis, Grave's disease, diabetes (e.g., Type I diabetes) and systemic sclerosis.

In certain embodiments, inflammatory conditions that formulations provided herein are useful for treating or preventing include, but are not limited to, asthma and allergic rhinitis, bronchitis, chronic obstructive pulmonary disease, cystic fibrosis, inflammatory bowel disease, irritable bowel syndrome, Crohn's disease, mucous colitis, ulcerative colitis, diabetes (e.g., Type I diabetes and Type II diabetes) and obesity.

In certain embodiments, metabolic conditions that formulations provided herein are useful for treating or preventing include, but are not limited to, obesity, and diabetes (e.g., Type II diabetes).

In certain embodiments, cardiovascular diseases that formulations provided herein are useful for treating or preventing include, but are not limited to, stroke, myocardial infarction or ischemic damage to the heart, lung, gut, kidney, liver, pancreas, spleen or brain.

In certain embodiments, cardiovascular and renal diseases that formulations provided herein are useful for treating or preventing include, but are not limited to, atherosclerosis and the treatment or prevention of restenosis after vascular intervention such as angioplasty.

In certain embodiments, neurodegenerative diseases that formulations provided herein are useful for treating or preventing include, but are not limited to, Huntington's disease, Alzheimer's disease and HIV-associated encephalitis.

In certain embodiments, disorders caused, induced or exacerbated by ozone, cold or exercise that formulations provided herein are useful for treating or preventing include, but are not limited to, asthma, bronchitis, rhinitis, chronic obstructive pulmonary disease, lung inflammation or airway hyperresponsiveness.

In certain embodiments, formulations provided herein are useful for treating or preventing syndrome X or metabolic syndrome.

In certain embodiments, formulations provided herein are useful for treating or preventing insulin resistance. In certain embodiments, formulations provided herein are useful for treating or preventing insulin resistance that leads to diabetes (e.g., Type II diabetes).

In certain embodiments, provide herein are methods for the treatment or prevention of diabetes. In certain embodiments, diabetes that formulations provided herein are useful for treating or preventing include, but are not limited to, Type II diabetes, Type I diabetes, slow-onset Type I diabetes, diabetes insipidus, diabetes mellitus, gestational diabetes mellitus, maturity-onset diabetes, juvenile diabetes, insulin-dependent diabetes, non-insulin dependent diabetes, malnutrition-related diabetes, ketosis-prone diabetes, pre-diabetes, cystic fibrosis related diabetes or ketosis-resistant diabetes.

In certain embodiments, provided herein are methods for the treatment or prevention of fibrotic diseases and disorders. In certain embodiments, fibrotic conditions that formulations provided herein are useful for treating or preventing include, but are not limited to, idiopathic pulmonary fibrosis, myelofibrosis, hepatic fibrosis, renal fibrosis, chronic allograft nephropathy (including chronic allograft dysfunction), glomerulonephritis, glomerular nephropathy, glomerulopathies, steatofibrosis, steatohepatitis (including non-alcoholic steatohepatitis), or scleroderma.

In certain embodiments, formulations provided herein are useful for treating or preventing ischemia/reperfusion injury in general. Accordingly, formulations provided herein are useful for treating or preventing acute or chronic organ transplant rejection and for the preservation of tissue and organs.

In certain embodiments, cancers that formulations provided herein are useful for treating or preventing include, but are not limited to, cancers of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, and brain or central nervous system.

Cancers within the scope of the methods provided herein include those associated with BCR-ABL, and mutants or isoforms thereof, as well as kinases from the src kinase family, kinases from the Rsk kinase family, kinases from the CDK family, kinases from the MAPK kinase family, and tyrosine kinases such as Fes, Lyn, and Syk kinases, and mutants or isoforms thereof.

Further provided herein are methods for treating or preventing scleroderma, keloids, UV injury, or sunburn, and for improving or preventing scar formation comprising administering to a subject in need thereof an effective amount of one of the pharmaceutical formulations provided herein.

In certain embodiments, the scleroderma is localized, systemic, limited or diffuse scleroderma.

In certain embodiments, the systemic scleroderma comprises CREST (Calcinosis, Raynaud's Esophagaeal dysfunction, Sclerodacryl), Telangiectasiae), limited and diffuse. Systemic scleroderma is also known as systemic sclerosis or progressive systemic sclerosis. In certain embodiments, provided herein are methods of treating or preventing Raynaud's disease. In certain embodiments, systemic sclerosis comprises scleroderma lung disease, scleroderma renal crisis, cardiac manifestations, muscular weakness (including fatigue or limited CREST), gastrointestinal dysmotility and spasm, and abnormalities in the central, peripheral and autonomic nervous system (including carpal tunnel syndrome followed by trigeminal neuralgia). It also includes general disability, including depression, and impact on quality of life.

In certain embodiments, limited scleroderma is limited to the hands, the face, neck, or combinations thereof.

In certain embodiments, diffuse scleroderma comprises skin tightening and also occurs above the wrists (or elbows). In certain embodiments, the diffuse systemic sclerosis is sine scleroderma, comprising internal organ fibrosis, but no skin tightening; or familial progressive systemic sclerosis.

In one embodiment, scleroderma is not associated with wasting, such as disease-related wasting.

In one embodiment, provided herein are methods for the reduction, inhibition, or prevention of one or more of the following symptoms of scleroderma: (i) gradual hardening, thickening, and tightening of the skin (e.g., in extremities, such as hands, face, and feet); (ii) skin discoloration; (iii) numbness of extremities; (iv) shiny skin; (v) small white lumps under the surface of the skin that erupt into a chalky white fluid; (vi) Raynaud's esophagaeal dysfunction (pain, numbness, and/or color changes in the hands caused by spasm of the blood vessels upon exposure to cold or emotional stress); (vii) telangiectasia (red spots on, e.g., the hands, palms, forearms, face, and lips); (viii) pain and/or stiffness of the joints; (ix) swelling of the hands and feet; (x) itching of the skin; (xi) stiffening and curling of the fingers; (xii) ulcers (sores) on the outside of certain joints, such as knuckles and elbows; (xiii) digestive problems, such as heartburn, difficulty in swallowing, diarrhea, irritable bowel, and constipation; (xiv) fatigue and weakness; (xv) shortness of breath; (xvi) arthritis; (xvii) hair loss; (xviii) internal organ problems, (xix) digital ulcers; or (xx) digital auto-amputation, comprising administering to a subject in need thereof an effective amount of one of the pharmaceutical formulations provided herein.

Further provided herein are methods for treating, preventing or improving keloids (also known as a "keloidal scars") comprising administering to a subject in need thereof an effective amount of one of the pharmaceutical formulations provided herein. Keloids include raised and ill defined growth of skin in the area of damaged skin.

Further provided herein are methods for treating or preventing UV injury or sunburn comprising administering to a subject in need thereof an effective amount of one of the pharmaceutical formulations provided herein. Formulations provided herein are useful for treating or preventing UV injury or sunburn due to exposure of the skin to ultraviolet (UV) radiation (e.g., sunlight), including, but not limited to UVA, UVB, or both UVA and UVB. In one embodiment, formulations provided herein are useful for preventing UV injury or sunburn due to exposure of the skin to ultraviolet (UV) radiation (e.g., sunlight), including, but not limited to UVA, UVB, or both UVA and UVB.

In one embodiment, provided herein are methods for the reduction, inhibition or prevention of one or more of the following symptoms of UV injury and/or sunburn: (i) apoptotic cell death in the skin; (ii) apoptotic cell death in the epidermis; (iii) skin inflammation, (iv) erythema or tissue damage to skin; (v) immediate pigment darkening reaction; (vi) delayed tanning reaction; (vii) skin redness and irritation; (viii) shock; (ix) skin blistering; (x) chills; (xi) fever; (xii) nausea or vomiting, or both, (xiii) flulike symptoms, such as fever, severe aches and pains in the joints and muscles and around the eyes, and generalized weakness; or (xiii) skin loss, comprising administering to a subject in need thereof an effective amount of one of the pharmaceutical formulations provided herein.

Also provided herein are methods for improving or preventing scar formation comprising administering to a subject in need thereof (e.g., a subject having a wound or expecting a wound, such as that from a surgical procedure) an effective amount of one of the pharmaceutical formulations provided herein. In one embodiment, provided herein are methods for the improvement of prevention of one or more of the following: (i) size reduction of a scar, as measured by the length, width, or thickness of the scar; (ii) reduction in or absence of pain associated with the scar; (iii) reduction in or absence of itching associated with the scar; (iv) reduction in or absence of pigmentation in the scar; (v) increase of pliability in the scar; or (vi) a decrease in vascularity within the scar (evidenced, e.g., by a color change from purple to red to pink to white within the scar) comprising administering to a subject in need thereof an effective amount of one of the pharmaceutical formulations provided herein.

In certain embodiments, cancers and related disorders that can be treated or prevented by formulations provided herein include, but are not limited to, leukemias, including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome (or a symptom thereof such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia and chronic myelomonocytic leukemia (CMML), chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., *Medicine*, (1985), 2d ed., J.B. Lippincott Co., Philadelphia; and Murphy et al., *Informed Decisions: The Complete Book of Cancer Diagnosis, Treatment, and Recovery*, (1997), Viking Penguin, Penguin Books U.S.A., Inc., United States of America).

In certain embodiments, formulations provided herein are useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal orignin, including fibrosarcoma and rhabdomyoscarcoma; other tumors, including melanoma, seminoma, tetratocarcinoma, neuroblastoma and glioma; tumors of the central and peripheral nervous system, including astrocytoma, glioblastoma multiforme, neuroblastoma, glioma, and schwannomas; solid and blood born tumors; tumors of mesenchymal origin, including fibrosafcoma, rhabdomyoscarama, and osteosarcoma; and other tumors, including melanoma, xenoderma pegmentosum, keratoactanthoma, seminoma, thyroid follicular cancer and teratocarcinoma. It is also contemplated that cancers caused by aberrations in apoptosis would also be treated by the methods and formulations disclosed herein. Such cancers may include but not be limited to follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented in the ovary, bladder, breast, colon, lung, skin, pancreas, or uterus. In other specific embodiments, sarcoma, melanoma, or leukemia is treated or prevented.

In certain embodiments, formulations provided herein are useful for administration to patients in need of a bone marrow transplant to treat a malignant disease (e.g., patients suffering from acute lymphocytic leukemia, acute myelogenous leukemia, chronic myelogenous leukemia, chronic lymphocytic leukemia, myelodysplastic syndrome ("preleukemia"), monosomy 7 syndrome, non-Hodgkin's lymphoma, neuroblastoma, brain tumors, multiple myeloma, testicular germ cell tumors, breast cancer, lung cancer, ovarian cancer, melanoma, glioma, sarcoma or other solid tumors), those in need of a bone marrow transplant to treat a non-malignant disease (e.g., patients suffering from hematologic disorders, congenital immunodeficiences, mucopolysaccharidoses, lipidoses, osteoporosis, Langerhan's cell histiocytosis, Lesch-Nyhan syndrome or glycogen storage diseases), those undergoing chemotherapy or radiation therapy, those preparing to undergo chemotherapy or radiation therapy and those who have previously undergone chemotherapy or radiation therapy.

In certain embodiments, formulations provided herein are useful for the treatment or prevention of myeloproliferative disorders or myelodysplastic syndromes. In certain embodiments, the myeloproliferative disorder is polycythemia rubra vera; primary thrombocythemia; chronic myelogenous leukemia; acute or chronic granulocytic leukemia; acute or chronic myelomonocytic leukemia; myelofibro-erythroleukemia; or agnogenic myeloid metaplasia.

In certain embodiments, formulations provided herein are useful for the treatment or prevention of cancer or tumors resistant to other kinase inhibitors such as imatinib mesylate (STI-571 or GLEEVEC®) treatment. In certain embodiments, formulations provided herein are useful for the treatment or prevention of leukemias, including, but not limited to, gastrointestinal stromal tumor (GIST), acute lymphocytic leukemia or chronic myelocytic leukemia resistant to imatinib mesylate (STI-571 or Gleevec™) treatment.

In one embodiment, formulations provided herein are useful for the treatment or prevention of a disease or disorder treatable or preventable by modulating a kinase pathway, in one embodiment, the JNK pathway. In certain embodiments, diseases which are treatable or preventable by modulating, for example, inhibiting, a kinase pathway, in one embodiment, the JNK pathway, include, but are not limited to, rheumatoid arthritis; rheumatoid spondylitis; osteoarthritis; gout; asthma, bronchitis; allergic rhinitis; chronic obstructive pulmonary disease; cystic fibrosis; inflammatory bowel disease; irritable bowel syndrome; mucous colitis; ulcerative colitis; Crohn's disease; Huntington's disease; gastritis; esophagitis; hepatitis; pancreatitis; nephritis; multiple sclerosis; lupus erythematosus; Type II diabetes; obesity; atherosclerosis; restenosis following angioplasty; left ventricular hypertrophy; myocardial infarction; stroke; ischemic damages of heart, lung, gut, kidney, liver, pancreas, spleen and brain; acute or chronic organ transplant rejection; preservation of the organ for transplantation; organ failure or loss of limb (e.g., including, but not limited to, that resulting from ischemia-reperfusion injury, trauma, gross bodily injury, car accident, crush injury or transplant failure); graft versus host disease; endotoxin shock; multiple organ failure; psoriasis; burn from exposure to fire, chemicals or radiation; eczema; dermatitis; skin graft; ischemia; ischemic conditions associated with surgery or traumatic injury (e.g., vehicle accident, gunshot wound or limb crush); epilepsy; Alzheimer's disease; Parkinson's disease; immunological response to bacterial or viral infection; cachexia; angiogenic and proliferative diseases; solid tumor; and cancers of a variety of tissues such as colon, rectum, prostate, liver, lung, bronchus, pancreas, brain, head, neck, stomach, skin, kidney, cervix, blood, larynx, esophagus, mouth, pharynx, urinary bladder, ovary or uterine.

In certain embodiments, the methods provided herein comprise administering a formulation provided herein with food or a meal (e.g., a high fat meal). In specific embodiments, the food or meal can be consumed before, after or during administration of a formulation provided herein.

Further provided herein are methods for achieving certain pharmacokinetic (PK) parameters with respect to Compound I in a patient, comprising administering a formulation provided herein to said patient. In certain embodiments, the methods for achieving a PK parameter described herein further comprise measuring the amount of Compound I in a biological sample (e.g., urine, blood, serum or plasma) of a subject after administration of Compound I.

In certain embodiments, provided herein are methods for achieving a $T_{max}$ of about 1 to about 6 hours of Compound I in a patient, comprising administering a formulation provided herein to said patient. In specific embodiments, provided herein are methods for achieving a $T_{max}$ of about 1 hour, about 2 hours, about 3 hours, about 4 hours or about 5 hours of Compound I in a patient, comprising administering a formulation provided herein to said patient.

In certain embodiments, provided herein are methods for achieving a $t_{1/2}$ of about 15 to about 50 hours of Compound I in a patient, comprising administering a formulation provided herein to said patient. In specific embodiments, provided herein are methods for achieving a $t_{1/2}$ of about 22 hours, about 23 hours, about 24 hours, about 25 hours, about 26 hours or about 27 hours of Compound I in a patient, comprising administering a formulation provided herein to said patient.

In certain embodiments, provided herein are methods for achieving a $C_{max}$ of about 400 to about 1000 ng/mL of Compound I in a patient, comprising administering a formulation provided herein to said patient. In specific embodiments, provided herein are methods for achieving a $C_{max}$ of about 500 ng/mL, about 600 ng/mL, about 700 ng/mL or about 800 ng/mL of Compound I in a patient, comprising administering a formulation provided herein to said patient.

In certain embodiments, provided herein are methods for achieving an $AUC_{0-t}$ of about 10,000 to about 20,000 ng*hr/mL of Compound I in a patient, comprising administering a formulation provided herein to said patient. In specific embodiments, provided herein are methods for achieving an $AUC_{t-0}$ of about 15,000 ng*hr/mL, about 16,000 ng*hr/mL, about 17.000 ng*hr/mL or about 18,000 ng*hr/mL of Compound I in a patient, comprising administering a formulation provided herein to said patient.

In certain embodiments, provided herein are methods for achieving an $AUG_\infty$ of about 12,000 to about 25,000 ng*hr/mL of Compound I in a patient, comprising administering a formulation provided herein to said patient. In specific embodiments, provided herein are methods for achieving an $AUG_\infty$ of about 15,000 ng*hr/mL, about 16,000 ng*hr/mL, about 17,000 ng*hr/mL, about 18,000 ng*hr/mL or about 19,000 ng*hr/mL of Compound I in a patient, comprising administering a formulation provided herein to said patient.

In certain embodiments, provided herein are methods for achieving a CL/F of about 0.005 to about 0.02 mL/hr of Compound I in a patient, comprising administering a formulation provided herein to said patient. In specific embodiments, provided herein are methods for achieving a CL/F of about 0.01 mL/hr of Compound I in a patient, comprising administering a formulation provided herein to said patient.

In certain embodiments, provided herein are methods for achieving a Vz/F of about 0.15 to about 0.45 mL of Compound I in a patient, comprising administering a formulation provided herein to said patient. In specific embodiments, provided herein are methods for achieving a Vz/F of about 0.19 mL, about 0.20 mL, about 0.21 mL, about 0.22 mL, about 0.23 mL, about 0.24 mL, about 0.25 mL or about 0.26 mL of Compound I in a patient, comprising administering a formulation provided herein to said patient.

Formulations provided herein can further comprise other pharmacologically active compounds ("second active agents"). It is believed that certain combinations may work synergistically in the treatment of particular types of diseases or disorders, and conditions and symptoms associated with such diseases or disorders. Compound I can also work to alleviate adverse effects associated with certain second active agents, and vice versa.

One or more second active ingredients or agents can be used in the methods and formulations described herein. Second active agents can be large molecules (e.g., proteins) or small molecules (e.g., synthetic inorganic, organometallic, or organic molecules).

Examples of large molecule second active agents include, but are not limited to, hematopoietic growth factors, cytokines, and monoclonal and polyclonal antibodies. Specific examples of the active agents are anti-CD40 monoclonal antibodies (such as, for example, SGN-40); histone deacetylase inhibitors (such as, for example, SAHA and LAQ 824); heat-shock protein-90 inhibitors (such as, for example, 17-AAG); insulin-like growth factor-1 receptor kinase inhibitors; vascular endothelial growth factor receptor kinase inhibitors (such as, for example, PTK787); insulin growth factor receptor inhibitors; lysophosphatidic acid acyltransferase inhibitors; IkB kinase inhibitors; p38MAPK inhibitors; EGFR inhibitors (such as, for example, gefitinib and erlotinib HCL); HER-2 antibodies (such as, for example, trastuzumab (HERCEPTIN®) and pertuzumab (OMNITARG™); VEGFR antibodies (such as, for example, bevacizumab (AVASTIN™); VEGFR inhibitors (such as, for example, flk-1 specific kinase inhibitors, SU5416 and ptk787/zk222584); P13K inhibitors (such as, for example, wortmannin); C-Met inhibitors (such as, for example, PHA-665752); monoclonal antibodies (such as, for example, rituximab (RITUXAN®), tositumomab (BEXXAR®), edrecolomab (PANOREX®) and G250); and anti-TNF-α antibodies. Examples of small molecule active agents include, but are not limited to, small molecule anti-cancer agents and antibiotics (e.g., clarithromycin).

Specific second active compounds that can be combined with Compound I vary depending on the specific indication to be treated, prevented or managed.

For instance, for the treatment, prevention or management of cancer, second active agents include, but are not limited to: semaxanib; cyclosporin; etanercept; doxycycline; bortezomib; acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other second agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clathromycin; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (GLEEVEC®); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (GENASENSE®); O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurprin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, 2-methoxyestradiol, telomestatin, inducers of apoptosis in multiple myeloma cells (such as, for example, TRAIL), bortezomib, statins, semaxanib, cyclosporin, etanercept, doxycycline, bortezomib, oblimersen (GENASENSE®), remicade, docetaxel, celecoxib, melphalan, dexamethasone (DECADRON®), steroids, gemcitabine, cisplatinum, temozolomide, etoposide, cyclophosphamide, temodar, carboplatin, procarbazine, gliadel, tamoxifen, topotecan, methotrexate, ARISA®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (DOXIL®), paclitaxel, ganciclovir, adriamycin, estramustine sodium phosphate (EMCYT®), sulindac, and etoposide.

Similarly, examples of specific second active agents according to the indications to be treated, prevented, or managed can be found in the following references, all of which are incorporated herein in their entireties: U.S. Pat. Nos. 6,281,230 and 5,635,517; U.S. application Ser. Nos. 10/411,649, 10/483,213, 10/411,656, 10/693,794, 10/699,154, and 10/981,189.

Examples of additional second active agents include, but are not limited to, conventional therapeutics used to treat or prevent pain such as antidepressants, anticonvulsants, antihypertensives, anxiolytics, calcium channel blockers, muscle relaxants, non-narcotic analgesics, opioid analgesics, anti-inflammatories, cox-2 inhibitors, immunomodulatory agents, alpha-adrenergic receptor agonists or antagonists, immunosuppressive agents, corticosteroids, hyperbaric oxygen, ketamine, other anesthetic agents, NMDA antagonists, and other therapeutics found, for example, in the *Physician's Desk Reference* 2003. Specific examples include, but are not limited to, salicylic acid acetate)(ASPIRIN®), celecoxib (CELEBREX®), ENBREL®, ketamine, gabapentin (NEURONTIN®), phenyloin)(DILANTIN®), carbamazepine (TEGRETOL®), oxcarbazepine (TRILEPTAL®), valproic acid (DEPAKENE®), morphine sulfate, hydromorphone, prednisone, griseofulvin, penthonium, alendronate, dyphenhydramide, guanethidine, ketorolac (ACULAR®), thyrocalcitonin, dimethylsulfoxide (DMSO), clonidine (CATAPRESS®), bretylium, ketanserin, reserpine, droperidol, atropine, phentolamine, bupivacaine, lidocaine, acetaminophen, nortriptyline (PAMELOR®), amitriptyline (ELAVIL®), imipramine (TOFRANIL®), doxepin)(SINEQUAN®), clomipramine (ANANFRANIL®), fluoxetine (PROZAC®), sertraline (ZOLOFT®), nefazodone (SERZONE®), venlafaxine (EFFECXOR®), trazodone (DESYREL®), bupropion (WELLBUTRIN®), mexiletine, nifedipine, propranolol, tramadol, lamotrigine, ziconotide, ketamine, dextromethorphan, benzodiazepines, baclofen, tizanidine and phenoxybenzamine.

Examples of additional second active agents include, but are not limited to, a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an anti-inflammatory compound or an antiangiogenesis compound, or a combination thereof. Specific examples include, but are not limited to, verteporfin, purlytin, an angiostatic steroid, rhuFab, interferon-2γ, pentoxifylline, tin etiopurpurin, motexafin lutetium, 9-fluoro-11, 21-dihydroxy-16,17-1-methylethylidine-bis(oxy)pregna-1, 4-diene-3,20-dione, latanoprost (U.S. Pat. No. 6,225,348), tetracycline and its derivatives, rifamycin and its derivatives, macrolides, metronidazole (U.S. Pat. Nos. 6,218,369 and 6,015,803), genistein, genistin, 6'-O-Mal genistin, 6'-O-Ac genistin, daidzein, daidzin, 6'-O-Mal daidzin, 6'-O-Ac daidzin, glycitein, glycitin, 6'-O-Mal glycitin, biochanin A, formononetin (U.S. Pat. No. 6,001,368), triamcinolone acetomide, dexamethasone (U.S. Pat. No. 5,770,589), thalidomide, glutathione (U.S. Pat. No. 5,632,984), basic fibroblast growth factor (bFGF), transforming growth factor β (TGF-β), brain-derived neurotrophic factor (BDNF), plasminogen activator factor type 2 (PAI-2), EYE101 (Eyetech Pharmaceuticals), LY333531 (Eli Lilly), Miravant, and RETISERT implant (Bausch & Lomb). All of the references cited above are incorporated herein in their entireties by reference.

Examples of additional second active agents include, but are not limited to, keratolytics, retinoids, α-hydroxy acids, antibiotics, collagen, botulinum toxin, interferon, and immunomodulatory agents. Specific examples include, but are not limited to, 5-fluorouracil, masoprocol, trichloroacetic acid, salicylic acid, lactic acid, ammonium lactate, urea, tretinoin, isotretinoin, antibiotics, collagen, botulinum toxin, interferon, corticosteroid, transretinoic acid and collagens such as human placental collagen, animal placental collagen, Dermalogen, AlloDerm, Fascia, Cymetra, Autologen, Zyderm, Zyplast, Resoplast, and Isolagen.

Examples of additional second active agents include, but are not limited to, anticoagulants, diuretics, cardiac glycosides, calcium channel blockers, vasodilators, prostacyclin analogues, endothelin antagonists, phosphodiesterase inhibitors (e.g., PDE V inhibitors), endopeptidase inhibitors, lipid lowering agents, thromboxane inhibitors, and other therapeutics known to reduce pulmonary artery pressure. Specific examples include, but are not limited to, warfarin (COUMADIN®), a diuretic, a cardiac glycoside, digoxin-oxygen, diltiazem, nifedipine, a vasodilator such as prostacyclin (e.g., prostaglandin 12 (PGI2), epoprostenol (EPO, FLORAN®), treprostinil (REMODULIN®), nitric oxide (NO), bosentan (TRACLEER®), amlodipine, epoprostenol (FLORAN®), treprostinil (REMODULIN®), prostacyclin, tadalafil (CIALIS®), simvastatin (ZOCOR®), omapatrilat (VANLEV®), irbesartan (AVAPRO®), pravastatin (PRAVACHOL®), digoxin, L-arginine, iloprost, betaprost, and sildenafil (VIAGRA®).

Examples of additional second active agents include, but are not limited to, anthracycline, platinum, alkylating agent, oblimersen (GENASENSE®), cisplatinum, cyclophosphamide, temodar, carboplatin, procarbazine, gliadel, tamoxifen, topotecan, methotrexate, taxotere, irinotecan, capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (DOXIL®), paclitaxel, ganciclovir, adriamycin, bleomycin, hyaluronidase, mitomycin C, mepacrine, thiotepa, tetracycline and gemcitabine.

Examples of additional second active agents include, but are not limited to, chloroquine, quinine, quinidine, pyrimethamine, sulfadiazine, doxycycline, clindamycin, mefloquine, halofantrine, primaquine, hydroxychloroquine, proguanil, atovaquone, azithromycin, suramin, pentamidine, melarsoprol, nifurtimox, benznidazole, amphotericin B, pentavalent antimony compounds (e.g., sodium stiboglucuronate), interfereon gamma, itraconazole, a combination of dead promastigotes and BCG, leucovorin, corticosteroids, sulfonamide, spiramycin, IgG (serology), trimethoprim, and sulfamethoxazole.

Examples of additional second active agents include, but are not limited to: antibiotics (therapeutic or prophylactic) such as, but not limited to, ampicillin, clarithromycin, tetracycline, penicillin, cephalosporins, streptomycin, kanamycin, and erythromycin; antivirals such as, but not limited to, amantadine, rimantadine, acyclovir, and ribavirin; immunoglobulin; plasma; immunologic enhancing drugs such as, but not limited to, levami sole and isoprinosine; biologics such as, but not limited to, gammaglobulin, transfer factor, interleukins, and interferons; hormones such as, but not limited to, thymic; and other immunologic agents such as, but not limited to, B cell stimulators (e.g., BAFF/BlyS), cytokines (e.g., IL-2, IL-4, and IL-5), growth factors (e.g., TGF-β), antibodies (e.g., anti-CD40 and IgM), oligonucleotides containing unmethylated CpG motifs, and vaccines (e.g., viral and tumor peptide vaccines).

Examples of additional second active agents include, but are not limited to: a dopamine agonist or antagonist, such as, but not limited to, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, and Symmetrel; a MAO inhibitor, such as, but not limited to, iproniazid, clorgyline, phenelzine and isocarboxazid; a COMT inhibitor, such as, but not limited to, tolcapone and entacapone; a cholinesterase inhibitor, such as, but not limited to, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, and demecarium; an anti-inflammatory agent, including, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, Rho-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone or betamethasone and other glucocorticoids; and an antiemetic agent, such as, but not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of additional second active agents include, but are not limited to, immunomodulatory agents, immunosuppressive agents, antihypertensives, anticonvulsants, fibrinolytic agents, antiplatelet agents, antipsychotics, antidepressants, benzodiazepines, buspirone, amantadine, and other known or conventional agents used in patients with CNS injury/damage and related syndromes. Specific examples include, but are not limited to: steroids (e.g., glucocorticoids, such as, but not limited to, methylprednisolone, dexamethasone and betamethasone); an anti-inflammatory agent, including, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone; a cAMP analog including, but not limited to, db-cAMP; an agent comprising a methylphenidate drug, which comprises 1-threo-methylphenidate, d-threo-methylphenidate, dl-threo-methylphenidate, l-erythro-methylphenidate, d-erythro-methylphenidate, dl-erythro-methylphenidate, and a mixture thereof; and a diuretic agent such as, but not limited to, mannitol, furosemide, glycerol, and urea.

Examples of additional second active agents include, but are not limited to, a tricyclic antidepressant agent, a selective serotonin reuptake inhibitor, an antiepileptic agent (gabapentin, pregabalin, carbamazepine, oxcarbazepine, levitiracetam, topiramate), an antiaryhthmic agent, a sodium channel blocking agent, a selective inflammatory mediator inhibitor, an opioid agent, a second immunomodulatory compound, a combination agent, and other known or conventional agents used in sleep therapy. Specific examples include, but are not limited to, Neurontin, oxycontin, morphine, topiramate, amitryptiline, nortryptiline, carbamazepine, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, Symmetrel, iproniazid, clorgyline, phenelzine, isocarboxazid, tolcapone, entacapone, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, demecarium, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone, benzbromarone, betamethasone and other glucocorticoids, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of additional second active agents include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; and G-CSF; hydroxyurea; butyrates or butyrate derivatives; nitrous oxide; HEMOXIN™ (NIPRISAN™; see U.S. Pat. No. 5,800,819); Gardos channel antagonists such as clotrimazole and triaryl methane derivatives; Deferoxamine; protein C; and transfusions of blood, or of a blood substitute such as HEMOSPAN™ or HEMOSPAN™ PS (Sangart).

Administration of formulations provided herein and a second active agent to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. In certain embodiments, formulations provided herein administered orally. Preferred routes of administration for the second active agents or ingredients provided herein are known to those of ordinary skill in the art. See, e.g., *Physicians' Desk Reference*, 1755-1760 (56th ed., 2002).

6.5 Methods of Manufacture

In one embodiment, provided herein are methods for preparing the pharmaceutical formulations provided herein, comprising: (i) weighing out the desired amount of 4-((9-((3S)-tetrahydro-3-furanyl)-8-((2,4,6-trifluorophenyl)amino)-9H-purin-2-yl)amino)-trans-cyclohexanol, or a pharmaceutically acceptable salt, solvate, isomer, isotopologue, tautomer or racemic mixture thereof; (ii) passing 4-((9-((3S)-tetrahydro-3-furanyl)-8-((2,4,6-trifluorophenyl)amino)-9H-purin-2-yl)amino)-trans-cyclohexanol, or a pharmaceutically acceptable salt, solvate, isomer, isotopologue, tautomer or racemic mixture thereof through a screen; (iii) weighing out the desired amount of the excipients (e.g., a binder, such as silicified microcrystalline cellulose; a diluent, such as anhydrous lactose; a disintegrant, such as croscarmellose sodium; a lubricant, such as magnesium stearate; and/or a glidant); and (iv) combining 4-((9-((3S)-tetrahydro-3-furanyl)-8-((2,4,6-trifluorophenyl)amino)-9H-purin-2-yl)amino)-trans-cyclohexanol, or a pharmaceutically acceptable salt, solvate, isomer, isotopologue, tautomer or racemic mixture thereof with one or more of the excipients and blending.

In one embodiment, the methods for preparing the pharmaceutical formulations provided herein further comprise: (v) filling an appropriately sized capsule (e.g., a size 4 capsule for a 25 mg dose, a size 2 or size 0 capsule for a 100 mg dose and a size 0 capsule for a 200 mg dose) with the blended mixture to the desired fill weight.

In one embodiment, the methods for preparing the pharmaceutical formulations provided herein further comprise: (vi) compressing the material into a tablet coating said tablet with an appropriate inert or enteric coating (e.g., an Opadry® coating).

In one embodiment, provided herein are methods for preparing the pharmaceutical formulations provided herein, comprising a combination of the following steps: (i) weighing out the desired amount of 4-((9-((3S)-tetrahydro-3-furanyl)-8-((2,4,6-trifluorophenyl)amino)-9H-purin-2-yl)amino)-trans-cyclohexanol, or a pharmaceutically acceptable salt, solvate, isomer, isotopologue, tautomer or racemic mixture thereof; (ii) passing 4-((9-((3S)-tetrahydro-3-furanyl)-8-((2,4,6-trifluorophenyl)amino)-9H-purin-2-yl)amino)-trans-cyclohexanol, or a pharmaceutically acceptable salt, solvate, isomer, isotopologue, tautomer or racemic mixture thereof through a screen; (iii) weighing out the desired amount of the excipients (e.g., a binder, such as silicified microcrystalline cellulose; a diluent, such as anhydrous lactose; a disintegrant, such as croscarmellose sodium; a lubricant, such as magnesium stearate; and/or a glidant); (iv) passing each excipient through a screen; (v) combining 4-((9-((3S)-tetrahydro-3-furanyl)-8-((2,4,6-trifluorophenyl)amino)-9H-purin-2-yl)amino)-trans-cyclohexanol, or a pharmaceutically acceptable salt, solvate, isomer, isotopologue, tautomer or racemic mixture thereof and a binder (e.g., silicified microcrystalline cellulose) and blending; (vi) combining a diluent (e.g., anhydrous lactose) and a disintegrant (e.g., croscarmellose sodium) with the 4-((9-((3S)-tetrahydro-3-furanyl)-8-((2,4,6-trifluorophenyl)amino)-9H-purin-2-yl)amino)-trans-cyclohexanol, or a pharmaceutically acceptable salt, solvate, isomer, isotopologue, tautomer or racemic mixture thereof and binder mixture and blending; and (vii) combining a lubricant (e.g., magnesium stearate) with the 4-((9-((3S)-tetrahydro-3-furanyl)-8-((2,4,6-trifluorophenyl)amino)-9H-purin-2-yl)amino)-trans-cyclohexanol, or a pharmaceutically acceptable salt, solvate, isomer, isotopologue, tautomer or racemic mixture thereof, binder diluent and disintegrant mixture and blending.

In one embodiment, the methods for preparing the pharmaceutical formulations provided herein further comprise: (viii) filling an appropriately sized capsule (e.g., a size 4 capsule for a 25 mg dose, a size 2 or size 0 capsule for a 100 mg dose and a size 0 capsule for a 200 mg dose) with the blended mixture to the desired fill weight; and (ix) polishing capsules with a de-duster.

In one embodiment, the methods for preparing the pharmaceutical formulations provided herein further comprise: (viii) compressing the material into a tablet coating said tablet with an appropriate inert or enteric coating (e.g., an Opadry® coating).

In one embodiment, the methods for preparing the pharmaceutical formulations provided herein comprise carrying out the mixing of the lubricant over a time period longer than three minutes, longer than four minutes or about five minutes or longer. Without being limited by theory, it is believed that a longer lubricant mix time allows for better dispersion of the lubricant, resulting in reduced sticking to punch surfaces.

6.6 Solid Forms

Certain embodiments herein provide a pharmaceutical formulation comprising a solid form, such as a crystal form, of Compound I. Representative solid forms of Compound I include those described in U.S. Pat. App. Pub. No. 2009/0048275, such as in Section 5.2 at pages 4-8.

In certain embodiments, the solid form of Compound I can be obtained by a procedure comprising evaporating a solution of Compound I in ethyl acetate. In certain embodiments, Compound I is suspended in ethyl acetate and heated to 50° C. until completely dissolved, followed by evaporation at about 25° C.

A representative XRPD pattern of a solid form of Compound I is provided in FIG. 4. In certain embodiments, the solid form of Compound I is characterized by XRPD peaks located at one or more of the following approximate positions: 10.0, 11.9, 12.3, 12.8, 15.2, 16.0, 16.2, 16.7, 17.7, 18.5, 18.9, 19.4, 20.0, 20.6, 20.8, 21.6, 22.7, 23.1, 24.1, 24.4, 24.6, 24.8, 25.7, 25.9, 26.1, 26.3, 27.1, 27.4, 27.8 degrees 2θ (±0.1). In particular embodiments, the solid form Compound I is characterized by XRPD peaks located at one, two, three, four, five or six of the following approximate positions: 12.3, 16.0, 18.5, 18.9, 20.6, 23.1, 24.1 degrees 2θ (±0.1). In certain embodiments, the solid form of Compound I has an XRPD pattern comprising peaks at approximately 12.3, 16.0 and 18.5 degrees 2θ (±0.1). In certain embodiments, the solid form of Compound I has an XRPD pattern further comprising peaks at approximately 18.9, 20.6, 23.2 and 24.1° 2θ (±0.1) or 20.6, 23.2 and 24.1 degrees 2θ (±0.1).

In other embodiments, the solid form of Compound I is a bis-hydrate and can be obtained by a procedure comprising dissolving Compound I in acetone/water (50/50% v/v) and slowly evaporating the solution at room temperature.

A representative XRPD pattern of a bis-hydrate solid form of Compound I is provided in FIG. 9. In certain embodiments, the bis-hydrate solid form of Compound I is characterized by XRPD peaks located at one or more of the following approximate positions: 6.5, 9.2, 10.3, 11.2, 13.0, 13.4, 15.9, 18.4, 19.5, 20.1, 20.5, 21.1, 21.5, 21.8, 23.0, 23.8, 24.7, 25.6, 26.0, 26.8 degrees 2θ (±0.1). In particular embodiments, the solid form Compound I is characterized by XRPD peaks located at one, two, three, four, five or six of the following approximate positions: 6.5, 13.0, 13.4, 19.5, 20.1, 23.0, 23.8 degrees 2θ (±0.1). In certain embodiments, the solid form of Compound I has an XRPD pattern comprising peaks at approximately 6.5, 13.0 and 23.0 degrees 2θ (±0.1). In certain embodiments, the solid form of Compound I has an XRPD pattern further comprising peaks at approximately 13.4, 20.1 and 23.8 degrees 2θ (±0.1).

7. EXAMPLES

The following Examples are presented by way of illustration, not limitation.

Example 6.1

Capsule Formulations

Compound I was formulated as capsules, the formulations of which are summarized in Tables 1 to 3.

TABLE 1

Pharmaceutical Formulation I

| Component | Weight (%) | Per Unit (mg) | Per Batch (g) |
|---|---|---|---|
| Compound I | 25.00 | 25.00 | 375.00 |
| Anhydrous Lactose USP, NF, EP, JP (SUPER TAB ® 21AN) | 17.87 | 17.87 | 268.05 |
| Silicified Microcrystalline Cellulose (PROSOLV SMCC 50 ®) | 53.38 | 53.38 | 800.70 |
| Croscarmellose Sodium NF, EP, JP (AC-DI-SOL ®) | 3.00 | 3.00 | 45.00 |

TABLE 1-continued

Pharmaceutical Formulation I

| Component | Weight (%) | Per Unit (mg) | Per Batch (g) |
|---|---|---|---|
| Magnesium Stearate NF, EP (Vegetable Source, Hyqual) | 0.75 | 0.75 | 11.25 |
| Total | 100 | 100.00 | 1,500.00 |
| Size "4" White Opaque Capsules | NA | 15,000 | |

TABLE 2

Pharmaceutical Formulation II

| Component | Weight (%) | Per Unit (mg) | Per Batch (g) |
|---|---|---|---|
| Compound I | 25.00 | 100.00 | 750.00 |
| Anhydrous Lactose USP, NF, EP, JP (SUPER TAB ® 21AN) | 17.87 | 71.48 | 536.10 |
| Silicified Microcrystalline Cellulose (PROSOLV SMCC 50 ®) | 53.38 | 213.52 | 1,601.40 |
| Croscarmellose Sodium NF, EP, JP (AC-DI-SOL ®) | 3.00 | 12.00 | 90.00 |
| Magnesium Stearate NF, EP (Vegetable Source, Hyqual) | 0.75 | 3.00 | 22.50 |
| Total | 100 | 400.00 | 3,000.00 |
| Size "0" White Opaque Capsules | NA | 7,500 | |

TABLE 3

Pharmaceutical Formulation III

| Component | Weight (%) | Per Unit (mg) | Per Batch (g) |
|---|---|---|---|
| Compound I | 50.00 | 200.00 | 1,500.00 |
| Anhydrous Lactose USP, NF, EP, JP (SUPER TAB ® 21AN) | 11.55 | 46.20 | 346.50 |
| Silicified Microcrystalline Cellulose (PROSOLV SMCC 50 ®) | 34.15 | 136.60 | 1,024.50 |
| Croscarmellose Sodium NF, EP, JP (AC-DI-SOL ®) | 3.00 | 12.00 | 90.00 |
| Magnesium Stearate NF, EP (Vegetable Source, Hyqual) | 1.30 | 5.20 | 39.00 |
| Total | 100 | 400.00 | 3,000.00 |
| Size "0" White Opaque Capsules | NA | 7,500 | |

An 8 qt. V-blender was used to blend the powders of the components for Formulae I to III. Fillers were passed through a 30 mesh screen to break apart any agglomerates. Compound I was passed through a 40 mesh screen. A glidant was screened using a 40 mesh screen. A lubricant was screened through a 60 mesh screen. For most of the batches, a pre-mix of Compound I, sandwiched between one of the fillers, was employed for 10 minutes. Next, the remaining filler excipients, disintegrant, and glidant (as applicable) were added to the mixing vessel and blended for 14 minutes. Lastly, the lubricant was added to the blend and mixed for 5 minutes. A V-blender with a four quart V-shell was employed for blending at a factory set speed of 25 rpm.

Final blend samples were taken from each batch in triplicate for blend uniformity. Each sample taken was 1 to 3 times of the capsule fill weight. Bulk density of the final blend was determined using an appropriate size measuring cylinder (Pyrex N 3025 25 cc) and an analytical balance. Tap density was determined using a tap density tester (Globe Pharma Tap Density Tester, TDENS-01). From the results of the bulk and tap densities, Carr's index, which is calculated by dividing the difference between the tapped density and bulk density with the tapped density, and Hausner's ratio, which is calculated by dividing the tapped density with the bulk density, were calculated. Values of these parameters were used to evaluate compressibility and flow properties of the powder. The results are summarized in Table 4.

TABLE 4

Final Blend Bulk and Tap Density

| Formulation | Comp. I Weight (%) | Bulk Density | Tap Density | Hausner's Ratio | Carr's Index |
|---|---|---|---|---|---|
| I or II | 25 | 0.45 g/cc | 0.66 g/cc | 1.47 | 32 |
| III | 50 | 0.49 g/cc | 0.71 g/cc | 1.45 | 31 |

A Bosch encapsulation machine was used to produce capsules of Formulations I, II, and III. The encapsulation machine was operated at a speed of approximately 10,000 capsules per hour.

The 25 mg final blend (Formulation I) was encapsulated in size #4 capsules using a 9.0 mm dosing disc. The fill weight of each capsule was 100 mg and the final weight of each capsule was about 139.3 mg. No sticking was observed during encapsulation of 25 mg strength capsules. Size #4 capsule for the 25 mg strength capsules appeared to be optimal for the target fill weight of this blend. The encapsulation process did not exhibit any flow-related issues and weight variation of filled capsules was well within the acceptable range. Formulation I was prepared as size #4 white opaque capsules.

The 100 mg final blend (Formulation II) was encapsulated in size #0 capsules using a 17.5 mm dosing disc. The fill weight of each capsule was 400 mg and the final weight of each capsule was about 495.4 mg. During encapsulation no signs of sticking were observed and the process did not exhibit any flow-related issues and weight variation of filled capsules was well within the acceptable range. It was observed that during the 100 mg strength (25% drug load) encapsulation run, the powder slug was protruding slightly above the capsule body. Formulation II was prepared as size #0 white opaque capsules.

The 200 mg final blend (Formulation III) was encapsulated in size #0 capsules using a 17.5 mm dosing disc. The fill weight of each capsule was 400 mg and the final weight of each capsule was about 495.4 mg. No signs of sticking were observed and the encapsulation process was smooth without any issues. The encapsulation process did not exhibit any flow-related issues and weight variation of filled capsules was well within the acceptable range. Formulation III was prepared as size #0 white opaque capsules.

Upon completion of encapsulation, 100% weight checks were performed on each capsule batch utilizing the Sade sorter. For 100 mg and 200 mg strength capsules (sorting range of 467 mg-524 mg), rejection rate was less than about 5%. For the 25 mg strength capsules (sorting range of 133 mg-144 mg), rejection rate was less than about 1%.

For all three dosage strengths, the formulations and processes appear to be acceptable for clinical trial manufacturing. Process parameters for all stages of processes have been proven to be acceptable in providing capsules with good physical properties, including slug formation and consistent capsule weight.

Example 6.2

Dosing Disc Size Determination and Manual Encapsulation of 25 and 100 mg Strength Capsules Using 50% Drug Blend A 14.0 mm dosing disc was used as a starting point to evaluate the optimum disc size for capsule size #2 at 200 mg fill weight containing 50% compound I. The encapsulation results are summarized in Table 5.

TABLE 5

| Capsule | High Tamping (mg) | Low Tamping |
|---|---|---|
| 1 | 208.1 | 198.6 |
| 2 | 216.9 | 199.5 |
| 3 | 220.0 | 199.4 |
| Total | 645.0 | 597.6 |
| Average | 215.0 | 199.2 |

The range for dosing disc size was determined by (i) calculating mg per mm by dividing average value of test slug by the disc size used, and thus mg per mm values for high and low tamping are 15.4 mm (214.0/14.0) and 14.2 mm (199.2/14.0), respectively; (ii) calculating first target disc size by dividing theoretical fill weight with mg per mm, and thus the target disc size values for high and low tamping are 13.0 mm (200.0/15.4) and 14.1 mm (200.0/14.2), respectively, and then the average of the target disc size for high and low tamping, which is 13.6 mm; and (iii) calculating the range of dosing disc size based upon the formula of averaged target disc size±10% in mm, thus, 15.0 mm upper limit and 12.2 mm lower limit.

The 100 mg final blend (Formulation IV) was encapsulated in size #2 capsules (Table 6). The capsules were filled using a Model 300 Cropharm manual capsule filler set up with size "2" change parts. Sixty grams of the final blend was weighed and filled into 300 capsules using the capsule machine. The target weight was 261±5%, i.e., 249-273 mg. An empty capsule shell weighted about 61 mg. Thus, the fill weight of each capsule was 200 mg and the final weight of each capsule was about 261 mg. Formulation IV was prepared as size #2 white opaque capsules. The weights of filled capsules were checked manually using an analytical balance. Weight variation was found to be less then 3 percent of target weight.

The 25 mg final blend (Formulation V) was encapsulated in size #4 capsules (Table 7). The filling was done manually using a spatula and an analytical balance to a target weight of 89±4.5 mg. The average empty capsule weight was about 39 mg. Individual filled capsule weights for eleven capsules prepared are shown in Table 8.

TABLE 6

Pharmaceutical Formulation IV

| | Amount | |
|---|---|---|
| Component | Weight (%) | Per Unit (mg) |
| Compound I | 50.00 | 100.00 |
| Anhydrous Lactose USP, NF, EP, JP (SUPER TAB ® 21AN) | 11.55 | 23.10 |

TABLE 6-continued

Pharmaceutical Formulation IV

| Component | Weight (%) | Amount Per Unit (mg) |
|---|---|---|
| Silicified Microcrystalline Cellulose (PROSOLV SMCC 50 ®) | 34.45 | 68.90 |
| Croscarmellose Sodium NF, EP, JP (AC-DI-SOL ®) | 3.00 | 6.00 |
| Magnesium Stearate NF, EP (Vegetable Source, Hyqual) | 1.00 | 2.0 |
| Total | 100 | 200.00 |
| Size "2" White Opaque Capsules | | Each |

TABLE 7

Pharmaceutical Formulation V

| Component | Weight (%) | Amount Per Unit (mg) |
|---|---|---|
| Compound I | 50.00 | 25.000 |
| Anhydrous Lactose USP, NF, EP, JP (SUPER TAB ® 21AN) | 11.55 | 5.775 |
| Silicified Microcrystalline Cellulose (PROSOLV SMCC 50 ®) | 34.45 | 17.225 |
| Croscarmellose Sodium NF, EP, JP (AC-DI-SOL ®) | 3.00 | 1.500 |
| Magnesium Stearate NF, EP (Vegetable Source, Hyqual) | 1.00 | 0.500 |
| Total | 100 | 50 |
| #4 Hard Gelatin Capsules, White (0999) Opaque | | Each |

TABLE 8

Capsule weights
Capsule Weight (mg)

| 91.0 |
| 89.6 |
| 90.2 |
| 89.2 |
| 88.7 |
| 91.2 |
| 90.8 |
| 91.6 |
| 92.2 |
| 90.9 |
| 91.8 |

Formulations VI to VIII are summarized in Tables 9 to 11, respectively.

TABLE 9

Pharmaceutical Formulation VI

| Component | Weight (%) | Amount Per Unit (mg) |
|---|---|---|
| Compound I | 50.00 | 200.00 |
| Anhydrous Lactose USP, NF, EP, JP (SUPER TAB ® 21AN) | 11.55 | 46.20 |

TABLE 9-continued

Pharmaceutical Formulation VI

| Component | Weight (%) | Amount Per Unit (mg) |
|---|---|---|
| Silicified Macrocrystalline Cellulose (PROSOLV SMCC 50 ®) | 34.45 | 137.80 |
| Croscarmellose Sodium NF, EP, JP (AC-DI-SOL ®) | 3.00 | 12.00 |
| Magnesium Stearate NF, EP (Vegetable Source, Hyqual) | 1.00 | 4.00 |
| Total | 100 | 400 |
| #0 Hard Gelatin Capsule, White (0999) Opaque (Capsugel part#: GOHCS001246) | | Each |

TABLE 10

Pharmaceutical Formulation VII

| Component | Weight (%) | Amount Per Unit (mg) |
|---|---|---|
| Compound I | 25.00 | 25.00 |
| Anhydrous Lactose USP, NF, EP, JP (SUPER TAB ® 21AN) | 17.87 | 17.87 |
| Silicified Microcrystalline Cellulose (PROSOLV SMCC 50 ®) | 53.38 | 53.38 |
| Croscarmellose Sodium NF, EP, JP (AC-DI-SOL ®) | 3.00 | 3.00 |
| Magnesium Stearate NF, EP (Vegetable Source, Hyqual) | 0.75 | 0.75 |
| Total | 100 | 100.00 |
| #4, Hard Gelatin Capsule, White (0999) Opaque (Capsugel part#: G4ICS000217 or G4ICS000420) | | Each |

TABLE 11

Pharmaceutical Formulation VIII

| Component | Weight (%) | Amount Per Unit (mg) |
|---|---|---|
| Compound I | 50.00 | 100.00 |
| Anhydrous Lactose USP, NF, EP, JP (SUPER TAB ® 21AN) | 11.55 | 23.10 |
| Silicified Microcrystalline Cellulose (PROSOLV SMCC 50 ®) | 34.45 | 68.90 |
| Croscarmellose Sodium NF, EP, JP (AC-DI-SOL ®) | 3.00 | 6.00 |
| Magnesium Stearate NF, EP (Vegetable Source, Hyqual) | 1.00 | 2.0 |
| Total | 100 | 200.00 |
| #2, Hard Gelatin Capsule, White (0999) Opaque (Capsugel part#: G2HCS000482) | | Each |

Example 6.3

Developmental Effects of Compound I

Developmental effects were observed in rats at doses of ≥25 mg/kg/day and in rabbits at doses of 40 mg/kg/day of Compound I. In rats, at doses of 25 and 50 mg/kg/day developmental effects were limited to lower fetal weights and increased frequency of skeletal variations, while increased post implantation loss and developmental malformations involving heart and aortic vessels, ribs, and/or vertebrae were observed at the high dosage of 100 mg/kg/day. In rabbits, developmental effects included increased post implantation loss and slight increased incidences of rib and vertebrae malformations in fetuses. While the development effects in the rabbits may be due to the severity of the maternal toxicity observed, in rats development effects were observed in the absence of maternal toxicity at the lowest dose of 25 mg/kg/day. Maternal exposure (AUC) at the lowest observed effect level (LOEL: 25 mg/kg/day) in rats was 19,700 ng·hr/mL (~0.8- and 0.4-fold the human AUC at the 100 mg and 200 mg BID doses, respectively) and at NOAEL (20 mg/kg/day) in rabbits was 85,040 ng·hr/mL (~3.4- to 1.6-fold the human AUC at the 100 mg and 200 mg BID doses, respectively).

Example 6.4

An Oral Developmental Toxicity Study of Compound I in the Rat

Compound I was administered orally to four groups of 25 time-mated female CD® [Crl:CD® (SD)] rats/group at dose levels of 0 (vehicle, 1.0% carboxymethylcellulose/0.25% TWEEN® 80), 25, 50, or 100 mg/kg/day from Gestation Days (GD) 6 to 17. In addition, four groups of five time-mated females/group served as toxicokinetic (TK) animals and received the vehicle or test article in the same manner as the main study groups.

All animals in the main study and TK subgroups survived to scheduled termination. Pregnancy rates were 100% in all groups, providing 25 litters in each main study group with fetuses for evaluation on GD 20 and five litters in each TK group for fetal TK blood collection.

No maternal toxicity was seen at 25 mg/kg/day but developmental effects were seen from lower fetal weights (about 6% lower than controls) and increased frequency of several fetal skeletal variations. Maternal toxicity seen at the higher dose levels was evident from lower weight gain during the treatment period at 50 and 100 mg/kg/day, and lower food consumption at 100 mg/kg/day. At 100 mg/kg/day, there was also an increase in mean number of resorptions and increased post implantation loss index. Fetal body weights were about 11% and 27% lower than controls in the 50 and 100 mg/kg/day groups, respectively, and in both groups there was an increased frequency in occurrence of several fetal skeletal variations consistent with the lower fetal weights in these groups and suggestive of a developmental delay. In the 100 mg/kg/day group, there was also a slight increase in incidence of fetal malformations involving the heart and aortic vessels, ribs, and/or vertebrae; these effects are believed to be treatment-related.

Compound I was readily absorbed in pregnant rats following daily oral administration of Compound I for 11 days (GD 6-16). Exposures for Compound I increased in an approximately dose-proportional manner from 25 to 100 mg/kg/day. The mean toxicokinetics for Compound I are provided in Table 12.

In conclusion, in this rat developmental toxicity study with Compound I, the No-Observed-Adverse-Effect Level (NOAEL) for maternal toxicity was 25 mg/kg/day, and this was also the No-Observed-Effect Level (NOEL) for developmental toxicity.

TABLE 12

Summary of Mean Toxicokinetic Parameters for Compound I and Its S-cis Isomer in Pregnant Female Rats

| | Cmpd I (mg/kg/d) | | |
|---|---|---|---|
| | 25 | 50 | 100 |
| | Gestation Day 6 | | |
| $C_{max}$ (ng/mL) | 2422 | 3918 | 6793 |
| $AUC_\tau$ (ng·hr/mL) | 19490 | 49520 | 102400 |
| | Gestation Day 16 | | |
| $C_{max}$ (ng/mL) | 1934 | 4211 | 8129 |
| $AUC_\tau$ (ng·hr/mL) | 19700 | 42260 | 96930 |
| | Gestation Day 17[a] | | |
| Dam (ng/mL) | 1519 | 3407 | 6650 |
| Fetus (ng/mL)[b] | 896.7 | 2115 | 4012 |
| Fetal:Maternal Plasma Ratio[c] | 0.59 | 0.61 | 0.61 |

[a]Samples collected at 2 hours after dosing on Gestation Day 17.
[b]Pooled fetal blood samples
[c]Calculated from individual ratios
Abbreviations: $AUC_\tau$ = Area under the curve from the time of dosing (time zero) to the last quantifiable concentration; $C_{max}$ = maximum plasma concentration; d = day Example 6.5

An Oral Developmental Toxicity Study of Compound I in the Rabbit

Compound I was administered orally to four groups of 20 time-mated female New Zealand White Hra:(NZW)SPF rabbits/group at dose levels of 0 (vehicle, 1.0% carboxymethylcellulose/0.25% Tween® 80), 10, 20, or 40 mg/kg/day from Gestation Days (GD) 7 to 19. Additionally, four groups of five animals/group served as toxicokinetic (TK) animals and received the vehicle or test article in the same manner and dose levels as the main study groups. All time-mated females arrived at the laboratory on GD 0, the day evidence of mating was observed.

Analysis of dosing formulations from the first and last weekly preparations confirmed that all Compound I formulations had the appropriate concentrations (% of target concentration ranged from 97.3-103.7) and the first preparation was homogeneous on the day of formulating and following 8 days of storage (re-suspension homogeneity). Additionally, Compound I was not found in the vehicle control group.

All main study and TK animals in the control, 10, and 20 mg/kg/day groups survived to scheduled termination. At 40 mg/kg/day, one main study animal was found dead (death was considered test article related), five main study females aborted, and three main study and one TK females at uterine examination had all resorption sites in utero. Main study pregnancy indices in the control, 10, 20, and 40 mg/kg/day groups were 100%, 95%, 100%, and 95%, respectively, and there were 20, 19, 20, and 10 litters, respectively, with viable fetuses for evaluation on GD 29.

No maternal or developmental toxicity was seen at 10 mg/kg/day. At 20 mg/kg/day, there was an increased incidence of animals with feces few/absent and sporadic thin appearance observations noted at clinical examination, but in the absence of an effect on food consumption and body weight, this was not considered toxicologically meaningful. No other maternal toxicity or developmental toxicity was seen at this dose level. Clinical findings seen with increased frequency at 40 mg/kg/day and considered to be treatment related included feces few/absent (consistent with lower food consumption during the treatment period), red material in the cage pan (associated with the failed pregnancies), decreased activity, and thin appearance. Additional maternal toxicity at 40 mg/kg/day included lower gestation weights and weight gain, and lower food consumption.

Developmental toxicity seen in this study was limited to the 40 mg/kg/day dose level and involved a decrease in number of fetuses per doe, smaller litter size at uterine examination, and an increase in number of resorption sites and post-implantation loss. There was also an increase in overall incidence of litters containing a fetus or fetuses with malformations. Seven of the 10 litters (70%) available at GD 29 for fetal evaluation contained one or more fetuses with a malformation. However, only during the skeletal evaluations was there some similarity in malformations within the group. These changes, however, were not statistically different from controls (25%). These fetal effects were most likely due to the severe maternal toxicity observed in this group, although a direct test article-related effect cannot be ruled out. The mean toxicokinetics for Compound I are provided in Table 13.

In conclusion, in this rabbit developmental toxicity study with Compound I, the No-Observed-Adverse-Effect Level (NOAEL) for maternal toxicity was 20 mg/kg/day, and this was also the No-Observed-Effect Level (NOEL) for developmental toxicity.

TABLE 13

Summary of Mean Toxicokinetic Parameters for Compound I in Pregnant Female Rabbits

|  | Cmpd I (mg/kg/d) | | |
| --- | --- | --- | --- |
|  | 10 | 20 | 40 |
|  | Gestation Day 7 | | |
| $C_{max}$ (ng/mL) | 6517 | 12480 | 21230 |
| $AUC_\tau$ (ng · hr/mL) | 35250 | 79130 | 151900 |

TABLE 13-continued

Summary of Mean Toxicokinetic Parameters for Compound I in Pregnant Female Rabbits

|  | Cmpd I (mg/kg/d) | | |
| --- | --- | --- | --- |
|  | 10 | 20 | 40 |
|  | Gestation Day 18 | | |
| $C_{max}$ (ng/mL) | 6728 | 13190 | 21470 |
| $AUC_\tau$ (ng · hr/mL) | 39270 | 85040 | 151500 |
|  | Gestation Day 19[a] | | |
| Doe (ng/mL) | 4916 | 9217 | 15594 |
| Fetus (ng/mL)[b] | 465.7 | 870.7 | 3426 |
| Fetal:Maternal Plasma Ratio[c] | 0.10 | 0.09 | 0.24 |

[a]Samples collected at 2 hours after dosing on Gestation Day 19.
[b]Pooled fetal blood samples
[c]Calculated from individual ratios
Abbreviations: $AUC_\tau$ = Area under the curve from the time of dosing (time zero) to the last quantifiable concentration; $C_{max}$ = maximum plasma concentration; d = day Example 6.6

Pharmaceutical Formulation Development

Certain formulations comprising 4-((9-((3S)-tetrahydro-3-furanyl)-8-((2,4,6-trifluorophenyl)amino)-9H-purin-2-yl)amino)-trans-cyclohexanol were prepared and tested for a number of physical and chemical properties. Modifications were then made and subsequent formulations were also tested, until formulations possessing desirable physical and chemical properties were found. The following example describes these formulations and their testing The initial formulations prepare are described below in Table 14, the corresponding physical testing results are described below in Table 15 and the corresponding dissolution profiles are described below in Table 16.

TABLE 14

Formulation Matrix: Batches B0001F1-B0005F5

| INGREDIENT | % w/w/PER BATCH | | | | |
| --- | --- | --- | --- | --- | --- |
|  | B0001F1 | B0002F2 | B0003F3 | B0004F4 | B0005F5 |
| Compound I | 25.00 | 25.00 | 25.00 | 25.00 | 25.00 |
| Microcrystalline cellulose (Avicel ® PH-102) | 35.75 | — | 35.75 | 53.63 | 53.63 |
| Lactose Anhydrous (Super Tab ® 21 AN) | 35.75 | — | — | 17.62 | — |
| Pregelatinized Starch (Starch 1500 ®) | — | 35.75 | — | — | — |
| Mannitol (Mannogerm ™ EZ Spray Dried Mannitol) | — | 35.75 | 35.75 | — | 17.37 |
| Croscarmellose Sodium (Ac-Di-Sol ®) | 3.0 | 3.0 | — | 3.0 | — |
| Sodium Starch Glycolate (Explotab ®) | — | — | 3.0 | — | 3.0 |
| Magnesium Stearate (HyQual ® Vegetable Source) | 0.5 | 0.5 | — | 0.75 | — |
| Sodium Stearyl Fumerate (PRUV ®) | — | — | 0.5 | — | 1.0 |
| TOTAL | 100 | 100 | 100 | 100 | 100 |

TABLE 15

Physical Testing Results: Batches B0001F1-B0005F5

| TEST/STATISTICS | | BATCH # | | | | |
|---|---|---|---|---|---|---|
| | | B0001F1A (25 MG) | B0001F1B (100 MG) | B0002F2A (25 MG) | B0003F3A (25 MG) | B0003F3B (100 MG) |
| WEIGHT VARIATION (MG) | AVG (N = 10) | 101.0 | 406.7 | NOT PERFORMED (NP) | 98.2 | 402.2 |
| | % RSD | 2.9 | 1.0 | NP | 2.4 | 0.6 |
| THICKNESS (IN) | AVG (N = 10) | 0.1185 | 0.1976 | NP | 0.1182 | 0.1945 |
| | % RSD | 1.8 | 0.8 | NP | 1.5 | 0.6 |
| HARDNESS (KP) | AVG (N = 10) | 5.3 (N = 6) | 14.8 (N = 6) | NP | 5.4 | 20.7 |
| | % RSD | 12.1 | 7.3 | NP | 8.7 | 7.2 |
| FRIABILITY (% WEIGHT LOSS) | | 0.0 | 0.03 | NP | 0.07 | 0.10 |
| DIS-INTEGRATION (MIN:SEC) | $1^{ST}$ TAB | 01:18 | 02:22 | NP | 00:23 | 00:45 |
| | $3^{RD}$ TAB | 01:39 | 02:45 | NP | 01:18 | 01:31 |
| APPEARANCE | VISUAL | WHITE, SOME TABLETS WERE SLIGHTLY GLOSSY SOME WERE DULL & MATTE | WHITE, SLIGHTLY GLOSSY | WHITE, DULL TABLETS | WHITE, GLOSSY TABLES | WHITE, SLIGHTLY GLOSSY TABLETS, SOME TABLETS WERE DULL & MATTE |
| DENSITY (G/ML) | BULK | 0.49 | | 0.52 | 0.45 | |

| TEST/STATISTICS | | BATCH # | | | |
|---|---|---|---|---|---|
| | | B0004F4A (25 MG) | B0004F4B (100 MG) | B0005F5a (25 MG) | B0005F5B (100 MG) |
| WEIGHT VARIATION (MG) | AVG (N = 10) | 102.7 | 408.8 | 98.2 | 404.7 |
| | % RSD | 0.9 | 2.0 | 1.3 | 1.4 |
| THICKNESS (IN) | AVG (N = 10) | 0.1200 | 0.1968 | 0.1174 | 0.1983 |
| | % RSD | 0.8 | 1.8 | 1.2 | 1.1 |
| HARDNESS (KP) | AVG (N = 10) | 6.6 | 17.5 | 6.3 | 16.1 |
| | % RSD | 4.0 | 5.5 | 5.9 | 5.6 |
| FRIABILITY (% WEIGHT LOSS) | | 0.02 | 0.0 | 0.0 | 0.0 |
| DIS-INTEGRATION (MIN:SEC) | $1^{ST}$ TAB | 02:00 | 0.3:02 | 00:40 | 00:59 |
| | $3^{RD}$ TAB | 02:10 | 03:44 | 00:54 | 01:07 |
| APPEARANCE | VISUAL | WHITE, SOME TABLETS WERE GLOSSY, SOME WERE LIGHTLY DULL | WHITE, GLOSSY TABLETS, SOME WERE SLIGHTLY DULL | WHITE, SOME TABLETS WERE MORE GLOSSY, SOME WERE DULL | WHITE, SOME TABLETS WERE GLOSSY, SOME WERE DULL |
| DENSITY (G/ML) | BULK | 0.45 | | 0.43 | |

TABLE 16

Dissolution Profile Results: Batches B0001F1-B0005F5

| BATCH | STATISTICS (n = 3 tested) | AVERAGE % Compound I RELEASED PER TIME POINT (MINUTES) | | | | | |
|---|---|---|---|---|---|---|---|
| | | 5 | 15 | 30 | 45 | 60 | 75 (INFINITY SPIN) |
| B0001F1A (25 MG) | AVG | 104 | 107 | 108 | 108 | 108 | 108 |
| | % RSD | 3.4 | 0.4 | 0.3 | 0.3 | 0.2 | 0.1 |
| B0001F1B (100 MG) | AVG | 94 | 103 | 104 | 104 | 105 | 105 |
| | % RSD | 3.9 | 1.1 | 1.3 | 1.3 | 1.2 | 0.9 |
| B0003F3A (25 MG) | AVG | 80 | 86 | 90 | 94 | 93 | 100 |
| | % RSD | 3.3 | 2.3 | 2.2 | 1.8 | 1.6 | 2.1 |
| B0003F3B (100 MG) | AVG | 76 | 81 | 84 | 85 | 86 | 99 |
| | % RSD | 1.2 | 1.0 | 1.3 | 1.0 | 0.8 | 0.7 |
| B0004F4A | AVG | 94 | 96 | 96 | 97 | 97 | 97 |

TABLE 16-continued

| | | AVERAGE % Compound I RELEASED PER TIME POINT (MINUTES) | | | | | |
|---|---|---|---|---|---|---|---|
| BATCH | STATISTICS (n = 3 tested) | 5 | 15 | 30 | 45 | 60 | 75 (INFINITY SPIN) |
| (25 MG) | % RSD | 1.5 | 1.5 | 1.4 | 1.4 | 1.6 | 1.7 |
| B0004F4B | AVG | 100 | 102 | 103 | 103 | 103 | 103 |
| (100 MG) | % RSD | 3.0 | 1.5 | 1.5 | 1.5 | 0.8 | 1.5 |

Batches were prepared at sizes of 200 or 250 g. Tablets were compressed at a press speed of approximately 29 rpm using two sets of tooling. The compression of batch B0001F1, containing equal parts of AVICEL® PH 102 and Super Tab® 21AN, resulted in low hardness values and filming on the punch faces at both the 25 mg and 100 mg strengths. Hardness values greater than 2 kP were not achieved during compression of batch B0002F2A, which was comprised of equal portions of Starch 1500 and Mannogem™ EZ Spray Dried Mannitol. Batch B0003F3 tablets, containing equal quantities of AVICEL® PH-102 and Mannogem™ EZ Spray Dried Mannitol, yielded low hardness values as well. Tablet breakage was observed for the 100 mg strength (B0003F3B). It was decided to modify formulations 1 and 3 to increase the quantity of AVICEL® PH 102. These changes were implemented and prepared as batches B0004F4 and B0005F5. Although the hardness values increased slightly, filming of the punch faces was observed during compression in both strengths.

For the next set of experiments, it was decided to make adjustments to the formulations as well as implementing new excipients of interest. The goal of the next batches was to improve blend flow, increase tablet hardness, and to prevent tablet sticking, filming and capping during compression. All batches in this set of experiments and for the remainder of the study included a 5 minute lubricant mix, which was increased from 3 minutes in the previous batches. Without being limited by theory, the increased mix time was intended to allow for adequate dispersion of the lubricant in an effort to eliminate the observed tablets sticking to the punch surfaces.

The following modifications were made to the prior batches: (i) modify batch F4 by reducing the concentration of magnesium stearate from 0.75% to 0.5% (batch B0006F6); (ii) repeat batch F5 with the increased lubricant mix time (batch B0007F7); (iii) use a combination of AVICEL® PH-102 and Starch 1500® in an effort to improve tablet hardness (batch B0008F8); (iv) base a new formula on F6 where the Super Tab® 21AN lactose concentration was increased to 56.5% from 17.62% in an effort to improve blend flow during compression due to increased particle size of lactose (batch B0009F9); (v) implement a combination of two grades of MCC (AVICEL® PH-102 and PH-105), SuperTab® 21AN, and the inclusion of Cab-O-Sil® M5P at a 0.2% level (the incorporation of a glidant (Cab-O-Sil® M5P) and AVICEL® PH-105 was to improve blend flow characteristics and compressibility properties, respectively) (batch B0010F10); and (vi) incorporate PROSOLV SMCC 50® at 53.63% as the main filler in an effort to improve tablet hardness (batch B0011F11).

These subsequent formulations prepared are described below in Table 17, the corresponding physical testing results are described below in Tables 18 and 19 and the corresponding dissolution profiles are described below in Table 20.

TABLE 17

Formulation Matrix: Batches B0006F6-B00011F11

| | % w/w/PER BATCH | | | | | |
|---|---|---|---|---|---|---|
| INGREDIENT | B0006F6 | B0007F7 | B0008F8 | B0009F9 | B0010F10 | B0011F11 |
| Compound I | 25.00 | 25.00 | 25.00 | 25.00 | 25.00 | 25.00 |
| Microcrystalline cellulose (Avicel ® PH-102) | 53.63 | 53.63 | 35.75 | 15.0 | 26.72 | — |
| Microcrystalline cellulose (Avicel ® PH-105) | — | — | — | — | 26.72 | — |
| Sillicified Microcrystalline Cellulose (PROSOLV SMCC 50 ®) | — | — | — | — | — | 56.63 |
| Anhydrous Lactose (Super Tab ® 21AN) | 17.87 | — | — | 56.5 | 17.87 | 17.87 |
| Pregelatinized Maize Starch, (Starch 1500 ®) | — | — | 35.75 | — | — | — |
| Mannitol (Mannogem ™ EZ Spray Dried Mannitol) | — | 17.37 | — | — | — | — |
| Croscarmellose Sodium (Ac-Di-Sol ®) | 3.0 | — | 3.0 | 3.0 | 3.0 | 3.0 |
| Colloidal Silicon Dioxide (Untreated Fumed Silica) (Cab-O-Sil ® M-5P) | — | — | — | — | 0.2 | — |
| Sodium Starch Glycolate (Explotab ®) | — | 3.0 | — | — | — | — |
| Magnesium Stearate (HyQual ® Vegetable Source) | 0.5 | — | 0.5 | 0.5 | 0.5 | 0.5 |
| Sodium Stearyl Fumerate (PRUV ®) | — | 1.0 | — | — | — | — |
| TOTAL | 100.0 | 100.0 | 100.0 | 100.0 | 100.0 | 100.0 |
| POTENTIAL PROTOTYPE FORMULATION | I | II | II | I | I | I |

TABLE 18

Physical Testing Results: Batches B0006F6-B0008F8

| TEST/STATISTICS | | B0006f6A (NOMINAL HARDNESS) | B0006f6A (LOW HARDNESS) | B0006f6A (HIGH HARDNESS) | B0006F6b | B0007F7a (NOMINAL HARDNESS) |
|---|---|---|---|---|---|---|
| WEIGHT VARIATION (MG) | AVG (N = 10) | 102.0 | 98.7 | 101.8 | 404.8 | 99.8 |
| | % RSD | 0.4 | 0.7 | 2.8 | 0.6 | 0.5 |
| THICKNESS (IN) | AVG (N = 10) | 0.1080 | 0.1069 | 0.1074 | 0.1827 | 0.1090 |
| | % RSD | 0.6 | 1.3 | 1.8 | 0.4 | 1.0 |
| HARDNESS (KP) | AVG (N = 10) | 6.5 | 5.7 | 6.9 | 17.0 | 6.1 |
| | % RSD | 5.1 | 14.6 | 5.2 | 3.9 | 4.2 |
| FRIABILITY (% WEIGHT LOSS) | | 0.11 | 0.25 | 0.18 | −0.02 | 0.06 |
| DIS-INTEGRATION (MIN:SEC) | $1^{ST}$ TAB | 01:21 | 00:55 | 01:22 | 03:05 | 00:26 |
| | $3^{RD}$ TAB | 01:30 | 01:11 | 01:34 | 03:36 | 00:32 |
| APPEARANCE | VISUAL | | WHITE, GLOSSY, UNIFORM | | | WHITE TO OFF WHITE, GLOSSY UNIFORM |
| DENSITY (G/ML) | BULK TAPPED CARR'S INDEX (%) | | REFER TO BATCH B0004F4 (REPEAT BATCH WITH 0.5% MG. STEARATE) | | | REFER TO BATCH B0005F5 (REPEAT BATCH WITH INCREASED MIXING) |

| TEST/STATISTICS | | B0007F7a (LOW HARDNESS) | B0007F7b | B0008F8a (n = 6) | B0008F8B |
|---|---|---|---|---|---|
| WEIGHT VARIATION (MG) | AVG (N = 10) | 101.6 | 395.7 | 102.4 | 404.1 |
| | % RSD | 0.7 | 1.2 | 1.2 | 0.9 |
| THICKNESS (IN) | AVG (N = 10) | 0.1146 | 0.1839 | 0.1160 | 0.1964 |
| | % RSD | 0.2 | 0.9 | 1.1 | 0.7 |
| HARDNESS (KP) | AVG (N = 10) | 4.0 | 16.1 | 2.2 | 5.9 |
| | % RSD | 3.4 | 5.3 | 7.7 | 8.2 |
| FRIABILITY (% WEIGHT LOSS) | | 0.18 | 0.00 | NOT PERFORMED (NP) | NP |
| DIS-INTEGRATION (MIN:SEC) | $1^{ST}$ TAB | 00:10 | 01:01 | NP | 01:58 |
| | $3^{RD}$ TAB | 00:15 | 01:07 | NP | 02:04 |
| APPEARANCE | VISUAL | NOT PERFORMED | WHITE, GLOSSY, UNIFORM; SOME TABLETS EXHIBITED STRESS MARKS ON SIDES AND FACES | WHITE, DULL UNIFORM | WHITE, SLIGHTLY DULL/SLIGHT GLOSS, UNIFORM |
| DENSITY (G/ML) | BULK TAPPED CARR'S INDEX (%) | REFER TO BATCH B0005F5 (REPEAT BATCH WITH INCREASED MIXING) | | | 0.49 0.78 0.37 |

TABLE 19

Physical Testing Results: Batches B0009F9-B00011F11

| TEST/STATISTICS | | BATCH # | | | | | |
|---|---|---|---|---|---|---|---|
| | | B0009F9A (25 MG) (N = 6) | B0009F9B (100 MG) | B0010F10A (25 MG) | B0010F10B (100 MG) | B0011F11A (25 MG) | B0011F11B (100 MG) |
| WEIGHT VARIATION (MG) | AVG (N = 10) | 100.8 | 400 | 101.7 | 397.7 | 102.9 | 401.2 |
| | % RSD | 1.3 | 0.8 | 1.7 | 1.3 | 1.1 | 0.9 |
| THICKNESS (IN) | AVG (N = 10) | 0.1083 | 0.1844 | 0.1154 | 0.1932 | 0.1158 | 0.1957 |
| | % RSD | 1.7 | 0.8 | 1.3 | 0.7 | 0.7 | 0.5 |
| HARDNESS (KP) | AVG (N = 10) | 1.9 | 11.3 | 10.7 | 20.5 | 12.0 | 22.5 |
| | % RSD | 6.8 | 7.3 | 3.9 | 6.3 | 2.2 | 4.8 |
| FRIABILITY (% WEIGHT LOSS) | | NOT PERFORMED (NP) | NP | 0.14 | 0.03 | 0.07 | −0.02 |
| DIS-INTEGRATION (MIN:SEC) | $1^{ST}$ TAB | NP | 01:16 | 02:55 | 02:47 | 03:19 | 01:58 |
| | $3^{RD}$ TAB | NP | 01:27 | 03:16 | 03:21 | 03:36 | 02:25 |
| APPEARANCE | VISUAL | WHITE, GLOSSY/HIGH SHEEN, UNIFORM | WHITE, GLOSSY, UNIFORM | SLIGHTLY OFF WHITE, GLOSSY, UNIFORM | SLIGHTLY OFF WHITE, GLOSSY, UNIFORM | OFF WHITE, GLOSSY, UNIFORM | WHITE TO OFF-WHITE GLOSSY, UNIFORM |
| DENSITY (G/ML) | BULK TAPPED CARR'S INDEX (%) | MODIFIED BATCH FROM B0004F4 | | 0.43 0.74 41 | | 0.42 0.64 34 | |

TABLE 20

Physical Testing Results: Batches B00010F1A, B0011F11A and B00011F11B

| | | AVERAGE % Compound I RELEASED PER TIME POINT (MINUTES) | | | | | |
|---|---|---|---|---|---|---|---|
| BATCH | VESSEL # | 5 | 15 | 30 | 45 | 60 | 75 (INFINITY SPIN) |
| B0010F10A (25 MG) | 1 | 94 | 101 | 100 | 100 | 100 | 101 |
| | 2 | 95 | 100 | 100 | 100 | 100 | 100 |
| | 3 | 94 | 101 | 102 | 102 | 102 | 102 |
| | AVG | 94 | 101 | 101 | 101 | 101 | 101 |
| | % RSD | 0.6 | 0.8 | 0.8 | 1.1 | 1.1 | 1.0 |
| B0011F11A (25 MG) | 1 | 99 | 101 | 101 | 101 | 101 | 101 |
| | 2 | 96 | 100 | 101 | 101 | 101 | 101 |
| | 3 | 97 | 100 | 101 | 101 | 101 | 101 |
| | AVG | 98 | 101 | 101 | 101 | 101 | 101 |
| | % RSD | 1.5 | 0.3 | 0.2 | 0.1 | 0.2 | 0.1 |
| B0011F11B (100 MG)) | 1 | 99 | 100 | 101 | 101 | 101 | 101 |
| | 2 | 96 | 98 | 98 | 98 | 98 | 98 |
| | 3 | 97 | 100 | 100 | 101 | 101 | 101 |
| | AVG | 97 | 100 | 100 | 100 | 100 | 100 |
| | % RSD | 1.6 | 1.3 | 1.4 | 1.5 | 1.4 | 1.3 |

Batches were prepared at sizes of 200 or 250 g. Tablets were compressed at approximately 29 rpm using two sets of tooling. During compression of batch B0006F6A, the hardness values varied and remained low despite the reduction in magnesium stearate in the blend. Although there appeared to be neither sticking during compression, nor filming on the punch surfaces, the hardness values were quite low at approximately 6 and 7 kP. The tablet press was adjusted through out the compression to increase the hardness values as data were collected at low, nominal and high hardness values. Low hardness values of 4-6 kP were obtained during the compression of batch B0007F7A as well. It was determined not to perform any chemical testing on these two batches. Poor flow from the hopper was observed during the compression of batches B0008F8A and B0008F8B as well as low tablet hardness values. Batches B0010F10 and B0011F11 were made in an effort to overcome the challenge of low tablet hardness. Batch B0010F10 blend exhibited poor flow from the hopper, however, the incorporation of AVICEL® PH-105 made a noticeable difference in tablet hardness with approximate average values of 11 kP and 21 kP for batches B0010F10A (25 mg) and B0010F10B (100 mg), respectively. The hardness values were a great improvement compared to all previous batches. Batch B0011F11 blend showed excellent flow properties primarily due to the incorporation of the silicified microcrystalline cellulose (PROSOLV SMCC 50®) as target hardness values were achieved at 12 kP and 23 kP for batches B0011F11A and B0011F11B, respectively. In addition there were no signs of tablet sticking nor filming of the tablet punches observed during the compression. Because of the compression success of batches B0010F10 and B0011F11, the two 25 mg tablet batches were submitted for dissolution profile testing.

Because of the promising dissolution data obtained for batch B0011F11A, as well as ideal blend and compression characteristics, additional chemical testing was performed on both strengths of tablets. Content uniformity and assay tests were performed on batches B0011F11A and B0011F11B, 25 mg and 100 mg strengths, respectively. The dissolution results for the 100 mg strength of tablets were highly notable with 100% release at the 15 minute time point.

Additional batches were prepared in a continuing effort to produce a second robust and unique prototype formulation. The incorporation of AVICEL® PH-105 in batch B0010F10 aided in higher tablet hardness values during compression, so it was decided to continue to use those excipients outlined in the formula as well as to evaluate new potential formulations. The goal was to explore other excipient combinations in an effort to improve blend flow and compression characteristics in a second prototype formulation.

The following modifications were made to the prior batches: (i) modify F10 by increasing the Cab-O-Sil® M5P concentration from 0.2% to 0.5% to improve blend flow (batch B0012F12); (ii) a new formulation using the combination of AVICEL® PH-105 and AVICEL® PH-302 was prepared (without being limited by theory, these two materials were utilized to (a) increase tablet hardness and to (b) improve blend flow due to the compressibility characteristics and increased density of the materials, respectively) (B0016F13); (iii) modify F13 using equal amounts of AVICEL® PH-105 and PH-302 and replacing SuperTab® 21AN, Ac-Di-Sol®, and magnesium stearate Hyqual® vegetable source with Mannogem™ EZ Spray Dried Mannitol with Explotab® and PRUV® in an effort to increase tablets hardness and blend flow (B0018F14); (iv) modify F14 by increasing the quantity of AVICEL® PH-105 in an effort to increase tablet hardness values (B0020F16); and (v) repeat F11 at the 25 mg strength at a larger scale for use in film coating and analytical methods development (B0021F11A).

TABLE 21

Formulation Matrix: Batches B00012F12-B00021F11A

% w/w/PER BATCH

| INGREDIENT | B0012F12 | B0013F10P | B0014F11P | B0015F12P | B0016F13 | B0017F12P | B0018F14 | B0019F15P | B0020F16 | B0021F11A |
|---|---|---|---|---|---|---|---|---|---|---|
| Compound I | 25.0 | — | — | — | 25.0 | — | 25.0 | — | 25.0 | 25.0 |
| Microcrystalline cellulose (Avicel® PH-102) | 26.7 | 26.72 | — | — | — | — | — | — | — | — |
| Microcrystalline cellulose (Avicel® PH-105) | 26.7 | 26.72 | — | — | 26.72 | — | 26.72 | — | 36.72 | — |
| Microcrystalline cellulose (Avicel® PH-302) | — | — | — | — | 26.72 | — | 26.72 | — | 16.72 | — |
| Sillicified Microcrystalline Cellulose (PROSOLV SMCC 50®) | — | — | 53.63 | 78.63 | — | 78.63 | — | 53.63 | — | 53.63 |
| Anhydrous Lactose (Super Tab® 21AN) | 17.6 | 17.87 | 17.87 | 17.87 | 17.57 | 17.87 | — | 17.87 | — | 17.87 |
| Mannitol (Mannogerm™ EZ Spray Dried Mannitol) | — | — | — | — | — | — | 17.07 | — | 17.07 | — |
| Croscarmellose Sodium (Ac-Di-Solo®) | 3.0 | 3.0 | 3.0 | 3.0 | 3.0 | 3.0 | — | 3.0 | — | 3.0 |
| Colloidal Silicon Dioxide (Untreated Fumed Silica) (Cab-O-Sil® M-5P) | 0.5 | 0.2 | — | — | 0.5 | — | 0.5 | 0.5 | 0.5 | — |
| Sodium Starch Glycolate (Explotab®) | — | — | — | — | — | — | 3.0 | — | 3.0 | — |

TABLE 21-continued

Formulation Matrix: Batches B00012F12-B00021F11A

| INGREDIENT | B0012F12 | B0013F10P | B0014F11P | B0015F12P | B0016F13 | B0017F12P | B0018F14 | B0019F15P | B0020F16 | B0021F11A |
|---|---|---|---|---|---|---|---|---|---|---|
| Magnesium Stearate (HyQuale ® Vegetable Source) | 0.5 | 0.5 | 0.5 | 0.5 | 0.5 | 0.5 | — | 0.5 | — | 0.5 |
| Sodium Stearyl Fumerate (PRUV ®) | — | — | — | — | — | — | — | 0.5 | 1.0 | — |
| Opadryl ® II White (PVA formula) | — | — | — | — | — | 4% | — | 4 mg | — | 4% |
| TOTAL | 100.0 | 100.0. | 100.0 | 100.0 | 100.0 | 100.0 | 100.0 | 79.0 mg | 100.0 | 100.0 |

TABLE 22

Physical Testing Results: Batches B00010F10-B00021F11A

| TEST/STATISTICS | | B0010F10A | B0010f10B | B0011F11A | B0011F11B | B0012F12A | B0012F12B |
|---|---|---|---|---|---|---|---|
| WEIGHT VARIATION (MG) | AVG (N = 10) | 101.7 | 397.7 | 102.9 | 401.2 | 106.8 | 398.5 |
| | % RSD | 1.7 | 1.3 | 1.1 | 0.9 | 1.6 | 1.1 |
| THICKNESS (IN) | AVG (N = 10) | 0.1154 | 0.1932 | 0.1158 | 0.1957 | 0.1244 | 0.1975 |
| | % RSD | 1.3 | 0.7 | 0.7 | 0.5 | 0.9 | 0.6 |
| HARDNESS (KP) | AVG (N = 10) | 10.7 | 20.5 | 12.0 | 22.5 | 11.9 | 20.7 |
| | % RSD | 3.9 | 6.3 | 2.2 | 4.8 | 6.2 | 7.6 |
| FRIABILITY (% WEIGHT LOSS) | | 0.14 | 0.03 | 0.07 | −0.02 | 0.1 | 0.1 |
| DIS-INTEGRATION (MIN:SEC) | $1^{ST}$ TAB | 02:55 | 02:47 | 03:19 | 01:58 | 03:28 | 02:28 |
| | $3^{RD}$ TAB | 03:16 | 03:21 | 03:36 | 02:25 | 03:52 | 04:03 |
| APPEARANCE | VISUAL | SLIGHTLY OFF WHITE, GLOSSY, UNIFORM | SLIGHTLY OFF WHITE, SLIGHTLY GLOSSY UNIFORM | OFF WHITE, GLOSSY, UNIFORM | WHITE TO OFF WHITE, GLOSSY, UNIFORM | WHITE, SLIGHTLY GLOSSY, UNIFORM | WHITE, VERY SLIGHTLY GLOSSY, UNIFORM |
| DENSITY (G/ML) | BULK | 0.43 | | 0.42 | | 0.44 | |

| TEST/STATISTICS | | B0015F12P | B0017F12PA COATED | B0018F14A | B0018F14B | B0021f11A |
|---|---|---|---|---|---|---|
| WEIGHT VARIATION (MG) | AVG (N = 10) | NP | 105.2 | 101.2 | 398.4 | NP |
| | % RSD | NP | 0.4 | 0.6 | 0.8 | NP |
| THICKNESS (IN) | AVG (N = 10) | NP | 0.1238 | 0.1224 | 0.2014 | NP |
| | % RSD | NP | 1.0 | 0.6 | 0.4 | NP |
| HARDNESS (KP) | AVG (N = 10) | NP | 24.1 | 8.1 | 17.8 | NP |
| | % RSD | NP | 3.9 | 9.1 | 2.8 | NP |
| FRIABILITY (% WEIGHT LOSS) | | 0.03 | −0.20 | 0.02 | 0.0 | 0.55 |
| DIS-INTEGRATION (MIN:SEC) | $1^{ST}$ TAB | 02:51 | 03:44 | 01:03 | 00:44 | 00:23 |
| | $3^{RD}$ TAB | 03:57 | 05:29 | 01:10 | 00:57 | 03:38 |
| APPEARANCE | VISUAL | WHITE, MOTTLED UNEVENLY COATED; R&D DEBOSSING WAS NOT | WHITE, ROUND CONCAVE, R&D DEBOSSED ON ONE SIDE | WHITE, GLOSSY, UNIFORM, R&D DEBOSSED ON ONE SIDE | WHITE, UNIFORM, GLOSSY | WHITE, R&D DE-BOSSED ON ONE SIDE; SOME TABLETS |

TABLE 22-continued

Physical Testing Results: Batches B00010F10-B00021F11A

|  |  | CLEAR ON MANY TABLETS |  | WERE MOTTLED DUE TO COATING |
|---|---|---|---|---|
| DENSITY (G/ML) | BULK | 0.39 | 0.44 | $NP_2$ |

These subsequent formulations prepared are described below in Table 21, the corresponding physical testing results are described below in Table 22 and the corresponding dissolution profiles are described below in Table 23.

TABLE 23

Dissolution Profile Results: Batches B00018F14A-B00018F14B

AVERAGE % Compound I RELEASED PER TIME POINT (MINUTES)

| BATCH | VESSEL # | 5 | 15 | 30 | 45 | 60 | 75 |
|---|---|---|---|---|---|---|---|
| B0018F14A | 1 | 104 | 105 | 105 | 105 | 106 | 105 |
| (25 MG) | 2 | 104 | 105 | 106 | 106 | 106 | 106 |
|  | 3 | 103 | 104 | 104 | 105 | 105 | 105 |
|  | AVG | 104 | 105 | 105 | 105 | 106 | 105 |
|  | % RSD | 0.6 | 0.6 | 0.6 | 0.5 | 0.5 | 0.5 |
| B0018F14B | 1 | 100 | 101 | 102 | 102 | 102 | 102 |
| (100 MG) | 2 | 98 | 101 | 101 | 101 | 101 | 101 |
|  | 3 | 97 | 101 | 101 | 101 | 102 | 102 |
|  | AVG | 98 | 101 | 101 | 102 | 102 | 102 |
|  | % RSD | 1.7 | 0.2 | 0.4 | 0.3 | 0.3 | 0.4 |

Improvements to blend flow were observed with batch B0018F14 using the combination of AVICEL® PH-105 and AVICEL® PH-302. Compression was conducted successfully at the two strengths: 25 mg and 100 mg. The tablet surfaces remained glossy and filming or sticking to the punch faces was not observed. Furthermore, the average tablet hardness values were promising at 8.1 kP and 17.8 kP, respectively, which were within the target hardness range desired. All in all, formulation F14 proved to be positive in regards to blend flow and tablet hardness values obtained. During the compression of batch B0020F16, the blend flow was observed to be quite poor, and there were no substantial improvements to the tablet hardness values compared to batch B0018F14. Chemical tests were not performed on batch B0020F16. Batch B0021F11A was prepared as a scale-up batch of batch B0011F11A at 1100 g, and was used for coating evaluation and analytical method development purposes. Tablets were compressed at a target of 10-12 kP using eight sets of ¼" SC tooling with R&D embossing on the upper punches. The compressed tablets exhibited picking on the R&D debossing due to sticking during compression. In addition, some tablets were broken, chipped and quite friable. These observations were supported by the friability value (% weight loss) of 0.55% compared to the first batch (same formula), B0011F11A, with a friability of 0.07% weight loss. With the chemical and physical testing data supporting the encouraging compression characteristics, formulation 14 was identified as the second prototype.

Although early stability data showed potential for the two prototype formulations, it was decided to implement modifications to the formulations in an effort to further improve blend flow and compression characteristics to eliminate sticking to punch surfaces. Batches B0029F18A and B0030F19A were prepared at the 25 mg strength tablets and were prepared at batch sizes of 1000 g.

The following modifications were made to the prior batches: (i) a modification of prototype I (F11), where the quantity of magnesium stearate Hyqual® Vegetable Source was increased from 0.5% to 0.65%. Without being limited by theory, this was done in an effort to reduce sticking of tablets to the punch surfaces (Batch B0029F18A); and (ii) the quantity of Cab-O-Sil® M5P was increased from 0.5% to 0.6% in prototype II (Batch B0030F19A). The Cab-O-Sil® M5P was incorporated in the 14 minute mix (after the Compound I premix) compared to prior batches where blending occurred in the last mixing steps. Without being limited by theory, the increased quantity and mix time was implemented in an effort to better distribute the glidant to improve the blend flow characteristics during the compression process.

These subsequent formulations prepared are described below in Table 24 and the corresponding physical testing results are described below in Table 25.

TABLE 24

Formulation Matrix: Batches B00029F18A-B00030F19A

| | % w/w/PER BATCH | |
|---|---|---|
| INGREDIENT | B0029F18A (25 mg) | B0030F19A (25 mg) |
| Compound I, Assay = 99.4% | 25.15* | 25.15* |
| Microcrystalline cellulose (Avicel ® PH-105) | — | 26.46 |
| Microcrystalline cellulose (Avicel ® PH-302) | — | 26.72 |
| Sillicified Microcrystalline Cellulose (PROSOLV SMCC 50 ®) | 53.33 | — |
| Anhydrous Lactose (Super Tab ® 21AN) | 17.87 | — |
| Mannitol (Mannogerm ™ EZ Spray Dried Mannitol) | — | 17.07 |
| Croscarmellose Sodium (Ac-Di-Sol ®) | 3.0 | — |

TABLE 24-continued

Formulation Matrix: Batches B00029F18A-B00030F19A

| | % w/w/PER BATCH | |
|---|---|---|
| INGREDIENT | B0029F18A (25 mg) | B0030F19A (25 mg) |
| Colloidal Silicon Dioxide (Untreated Fumed Silica) (Cab-O-Sil ® M-5P) | — | 0.6 |
| Sodium Starch Glycolate (Explotab ®) | — | 3.0 |
| Magnesium Stearate (HyQual ® Vegetable Source) | 0.65 | — |
| Sodium Stearyl Fumarate (PRUV ®) | — | 1.0** |
| Opadryl ® II White (PVA formula) | — | — |
| TOTAL | 100.0 | 100 |

*Adjusted based on the Assay value of 99.4%
**During the compression the amount of PRUV was increased to 1.9

TABLE 25

Physical Testing Results: Batches B00029F18A-B00030F19A

| | | BATCH # | |
|---|---|---|---|
| TEST/STATISTICS | | B0029F18A (25 MG) UNCOATED | B0030F19A (25 MG) UNCOATED |
| WEIGHT VARIATION (MG) | AVG (N = 10) | 99.7 | 101.2 |
| | % RSD | 1.4 | 2.6 |
| THICKNESS (IN) | AVG (N = 10) | 0.1180 | 0.1223 |
| | % RSD | 1.0 | 1.7 |
| HARDNESS (KP) | AVG (N = 10) | 12.5 | 8.3 |
| | % RSD | 4.6 | 10.7 |
| FRIABILITY (% WEIGHT LOSS) | | 0.14 | −0.01 |
| DIS-INTEGRATION (MIN:SEC) | $1^{ST}$ TAB | 03:44 | 01:01 |
| | $3^{RD}$ TAB | 04:36 | 01:29 |
| APPEARANCE | VISUAL | VERY SLIGHTLY OFF-WHITE, GLOSSY, PLAIN, UNIFORM | VERY SLIGHTLY OFF-WHITE, GLOSSY, PLAIN, UNIFORM |

Example 6.7

Dissolution Testing

The dissolution profile of a capsule or tablet can be obtained using standard methods known to one skilled in the art. An illustrative method for obtaining a dissolution profile is set forth below.

A 0.001N HCl (pH 3.0±0.1) dissolution medium is prepared by adding 1 mL of 1N HCl to 1000 mL of water and mixing well. The pH is adjusted to within 3.0±0.1 by adding more water or 1N HCl solution.

A reference standard of Compound I is prepared by adding a known amount of Compound I to a set volume of the dissolution medium.

Six samples are tested, with a single dosage form (e.g., capsule or tablet) per vessel. The dissolution apparatus is a USP Apparatus II (paddles). The dissolution medium volume is about 900 mL and the temperature is 37.0° C.±0.5° C. The paddle speed is 75 rpm, followed by a 250 rpm infinity spin after 60 minutes. Samples are taken at 10, 20, 30, 45, 60 and 75 minutes and the amount of dissolved Compound I is measured using HPLC. Observations are recorded for the first 20 minutes, such as: air bubbles on the capsules, spinning of the capsules, or any rubbery, swollen masses or thin film surrounding the capsule contents.

Example 6.8

Pharmacokinetics of a Single Oral Dose of Compound I

Methods: The study was a randomized, double-blind, placebo-controlled, single-ascending-dose trial. Forty-five healthy male subjects were enrolled into 1 of the 5 cohorts (active:placebo=7:2 per cohort). Subjects received single oral doses of 5 mg, 25 mg, 50 mg, 100 mg or 200 mg of unformulated Compound I in a capsule, or matching placebo.

Results: The major PK parameters are summarized in Table 26.

TABLE 26

Pharmacokinetic Parameters

| Parameter | 5 mg | 25 mg | 50 mg | 100 mg | 200 mg |
|---|---|---|---|---|---|
| $T_{max}$ (hr) | 1.5 (1.5-6.0) | 1.5 (1.1-4.0) | 2.0 (1.5-2.5) | 2.0 (1.5- 6.0) | 1.5 (1.0-2.5) |
| $C_{max}$ (ng/mL) | 34.69 (28.70) | 162.63 (66.97) | 367.41 (23.37) | 471.16 (67.06) | 1428.67 (41.75) |
| $AUC_{0-t}$ (ng · hr/mL) | 567.01 (16.50) | 3146.26 (41.94) | 6695.52 (22.37) | 10831.12 (31.20) | 23122.26 (23.09) |
| $AUC_{0-\infty}$ (ng · hr/mL) | 624.88 (20.29) | 3604.82 (44.31) | 7317.68 (23.44) | 13561.96 (24.76) | 26449.94 (26.51) |
| $t_{1/2}$ (hr) | 19.14 (41.99) | 24.05 (22.84) | 20.45 (11.52) | 27.51 (54.14) | 25.01 (26.43) |
| CLF (mL/min) | 133.36 (20.29) | 115.58 (44.31) | 113.88 (23.44) | 122.89 (24.76) | 126.02 (26.52) |
| Vz/F (L) | 220.88 (28.52) | 240.65 (32.36) | 201.59 (22.48) | 292.63 (57.94) | 272.84 (21.35) |

Value = geometric mean (CV %); $T_{max}$ = median (min-max)

The urinary excretion of unchanged Compound I ranged from 9-13% of the administered dose over 72 hrs post-dose.

Conclusions: Compound I was readily absorbed with a median $T_{max}$ of about 1.5-2 hours across the doses tested. $t_{1/2}$ was about 19-28 hours. $AUC_{0-t}$ was about 500-24000 ng·hr/mL. $AUC_{0-\infty}$ was about 600-27000 ng·hr/mL. $C_{max}$ was about 30-1500 ng/mL. CLF was about 100-140 mL/min. Vz/F was about 200-300 L. No dose-dependence was observed on $t_{1/2}$. Systemic exposure of Compound I ($C_{max}$ and $AUC_{0-\infty}$) appeared to increase in a dose-proportional manner across the doses tested.

Example 6.9

A Randomized, Double-Blind, Placebo-controlled Study to Evaluate the Pharmacokinetics (PK) of a Ascending Multiple Oral Doses of Compound I in Healthy Volunteers Subjects: Forty healthy male and female subjects between the ages of 20 and 50 were enrolled in the study. All subjects were in good health as determined by a medical history, physical examination, 12-lead ECG, serum biochemistry, hematology, urinalysis and virology. Subjects were not permitted to take any prescribed medication within 30 days or non-prescribed medication within 7 days of the first dose administration.

Study Design: This study was a randomized, double-blind, placebo-controlled, ascending-dose trial to evaluate the safety, tolerability and pharmacokinetics (PK) of multiple oral doses of Compound I. Subjects were enrolled into 1 of the 4 cohorts, 10 subjects per cohort (active:placebo=8:2). Subjects received a multiple oral dose of 25, 50, 100, or 200 mg unformulated Compound I in a capsule, or matching placebo, once daily (QD) for 14 days.

Assessments: Safety and tolerability were assessed by adverse event (AE) monitoring, clinical laboratory testing, vital sign measurement, 12-lead ECG measurement, concomitant medication assessment, and physical examination. Blood and urine samples were collected to assess the PK profile of Compound I and the S-cis isomer of Compound I. Blood samples (~5 mL) for plasma PK analysis were collected in $K_2$-EDTA vacutainer tubes to yield approximately 2 mL of plasma at each of the following time points: (i) Day 1: before dosing, and 0.25, 0.5, 1, 1.5, 2, 2.5, 3, 4, 6, 8, 10, 12, 16, and 24 hours after dosing; (ii) Day 3 to Day 9: before dosing; (iii) Day 10: before dosing, and 0.25, 0.5, 1, 1.5, 2, 2.5, 3, 4, 6, 8, 10, 12, and 16 hours after dosing; (iv) Day 11 to Day 13: before dosing; (v) Day 14: before dosing, and 0.25, 0.5, 1, 1.5, 2, 2.5, 3, 4, 6, 8, 10, 12, 16, 24, 48, 72, 96, 120, 144, and 168 hours after dosing. Urine samples for the PK analysis were collected as a single block at: (i) Day 1: before dosing (spot collection), 0 to 8, 8 to 16, and 16 to 24 hours after dosing; and (ii) Day 14: 0 to 8, 8 to 16, and 16 to 24 hours after dosing. Both plasma and urine concentrations of Compound I and its S-cis isomer were measured using validated liquid chromatography-tandem mass spectrometry (LC/MS/MS).

Data Analysis: Safety data were summarized using descriptive statistics by treatment. PK parameters for Compound I and its S-cis isomer were calculated using non-compartmental analysis using WinNonlin (Version 5.0.1 or greater; Pharsight Corporation, Mountain View, Calif.). Dose proportionality and dose independence were evaluated by visual inspection. Intra-subject variability was assessed using an ANOVA model using data from Days 10 and 14.

Results. Demographics: Forty subjects were enrolled and randomized to treatment. Of these, 35 (87.5%) subjects were white, 4 (10%) were African American, and 1 (2.5%) was mixed race. The majority of subjects were male (35/40, 87.5%). Demographics of the enrolled subjects are shown in Table 27. The treatment groups were well-matched for age, weight, height, and body mass index (BMI). Forty (100%) subjects completed the study.

TABLE 27

Subject Demographics: Mean (Standard Deviation)

| Demographics | Placebo (N = 8) | 25 mg Compound I (N = 8) | 50 mg Compound I (N = 8) | 100 mg Compound I (N = 8) | 200 mg Compound I (N = 8) |
|---|---|---|---|---|---|
| Age (years) | 31.5 (7.43) | 34.3 (9.63) | 38.0 (12.39) | 32.0 (6.07) | 32.5 (6.00) |
| Height (cm) | 174.06 (7.538) | 169.25 (8.565) | 169.88 (7.591) | 176.13 (5.969) | 175.50 (5.028) |
| Weight (kg) | 82.01 (6.654) | 72.85 (9.990) | 72.06 (4.309) | 78.48 (14.312) | 84.48 (7.387) |
| BMI (kg/m$^2$) | 27.08 (1.306) | 25.46 (3.239) | 25.15 (3.010) | 25.11 (3.229) | 27.43 (2.128) |

BMI = body mass index

Safety and Tolerability: Eighteen (45%) subjects (2/8 placebo, 16/32 active) reported a total of 55 treatment-emergent adverse events (TEAEs) (Table 28). There was no apparent dose-related trend with regard to number of subjects with TEAEs. This trend of lacking dose-relationship is further confirmed with the number of subjects reporting suspected TEAEs. The majority of TEAEs were reported by one subject each. TEAEs reported by 2 or more subjects are shown in Table 28. All TEAEs were mild in severity and resolved by the end of study, with the exception of one moderate TEAE not related to the investigational product (loss of dental cap). Three TEAEs (arthralgia, pharyngolaryngeal pain, and contact dermatitis) required the treatment with concurrent medication, while none of these TEAEs was considered to be related to the investigational product. One subject reported a supraventricular tachycardia (HR=147 bpm based on ECG) at 24 hrs post the last dose of 200 mg Compound I. The repeat ECG conducted 5 minutes later was normal. The subject was asymptomatic at time of the recording of abnormal ECG. There were no other clinically significant findings in the vital signs, 12-lead ECGs, or clinical laboratory values.

TABLE 28

Total and Commonly Reported Treatment-Emergent Adverse Events (Reported by ≥5% of All Subjects Receiving Compound I)

| Term | Placebo (N = 8) n (%) E | 25 mg (N = 8) n (%) E | 50 mg (N = 8) n (%) E | 100 mg (N = 8) n (%) E | 200 mg (N = 8) n (%) E |
|---|---|---|---|---|---|
| Total TEAEs | 2 (25.0) 4 | 3 (37.5) 6 | 6 (75.0) 20 | 4 (50.0) 10 | 3 (37.5) 15 |
| Headache | 1 (12.5) 2 | 1 (12.5) 1 | 2 (25.0) 2 | 3 (37.5) 3 | 0 |
| Dizziness | 0 | 0 | 0 | 2 (25.0) 2 | 1 (12.5) 1 |
| Flatulence | 0 | 0 | 2 (25.0) 4 | 0 | 0 |

TABLE 28-continued

Total and Commonly Reported Treatment-Emergent Adverse Events
(Reported by ≥5% of All Subjects Receiving Compound I)

| Term | Placebo (N = 8) n (%) E | 25 mg (N = 8) n (%) E | 50 mg (N = 8) n (%) E | 100 mg (N = 8) n (%) E | 200 mg (N = 8) n (%) E |
|---|---|---|---|---|---|
| Nausea | 0 | 1 (12.5) 1 | 0 | 0 | 1 (12.5) 3 |
| Dermatitis contact | 0 | 0 | 1 (12.5) 1 | 0 | 1 (12.5) 1 |
| Nasal congestion | 0 | 1 (12.5) 1 | 0 | 0 | 1 (12.5) 1 |
| Pharyngolaryngeal pain | 0 | 0 | 0 | 1 (12.5) 1 | 1 (12.5) 1 |
| Rhinitis | 0 | 0 | 1 (12.5) 1 | 1 (12.5) 1 | 0 | n = number of subjects reporting TEAE; % = n/N * 100; E = number of TEAE.

Pharmacokinetics: PK parameters are set forth in FIGS. 10, 11A-C and 12A-B and Tables 29-32.

TABLE 29

Compound I Plasma Pharmacokinetic Parameters (Geometric Mean (Geometric CV %)) in Healthy Subjects Following Once Daily Dosing (N = 8).

Day 1

| Compound I | $C_{max}$ (ng/mL) | $C_{trough}$ (ng/mL) | $t_{max}^a$ (hr) | $AUC_{(0-\tau)}^b$ (ng·hr/mL) | $AUC_{(0-\infty)}$ (ng·hr/mL) |
|---|---|---|---|---|---|
| 25 mg | 212 (21) | 55 (26) | 2.3 (1.5-3.0) | 2272 (20) | 4258 (54) |
| 50 mg | 406 (39) | 125 (27) | 2.3 (1.5-4.0) | 4559 (22) | 7751 (35) |
| 100 mg | 637 (69) | 183 (27) | 2.0 (1.0-3.0) | 7300 (51) | 12234 (30) |
| 200 mg | 1436 (44) | 375 (30) | 1.8 (1.0-4.0) | 15103 (27) | 26961 (47) |

Day 14

| Comp. I | $C_{max}$ (ng/mL) | $C_{trough}$ (ng/mL) | $t_{max}^a$ (hr) | $AUC_{(0-\tau)}^b$ (ng·hr/mL) | $AUC_{(0-\infty)}$ (ng·hr/mL) | CL/F (mL/min) | Vz/F (L) | $t_{1/2}$ (hr) | RA |
|---|---|---|---|---|---|---|---|---|---|
| 25 mg | 328 (24) | 130 (27) | 2.0 (1.0-2.5) | 4397 (17) | 10244 (26.93) | 95 (17) | 256 (22) | 31 (25) | 1.9 (17.1) |
| 50 mg | 740 (10) | 282 (17) | 2.0 (1.0-2.5) | 9812 (14) | 21287 (28) | 85 (14) | 193 (27) | 26 (34) | 2.2 (28.1) |
| 100 mg | 880 (33) | 400 (27) | 1.8 (1.0-2.5) | 12830 (26) | 31596 (29.10) | 130 (26) | 338 (32) | 30 (25) | 1.8 (32.7) |
| 200 mg | 1739 (27) | 643 (22) | 1.8 (1.0-3.0) | 22814 (19) | 48386 (22) | 146 (19) | 328 (35) | 26 (24) | 1.5 (41.1) |

$AUC_{(0-\tau)}$ = area under the plasma concentration versus time curve over one dosing interval; $AUC_{(0-\infty)}$ = from time 0 extrapolated to infinity; $C_{max}$ = observed maximal plasma concentration; $C_{trough}$ = observed plasma concentration at the end of the dosing interval; CL/F = apparent total plasma clearance; N = total number of subjects; RA = ratio of accumulation; $t_{max}$ = time to maximum concentration; $t_{1/2}$ = terminal elimination half-life; Vz/F = apparent total volume of distribution.
[a]Median (minimum – maximum);
[b]τ = 24 hours for once daily dosing.

TABLE 30

Intra-Subject Variability for $AUC_{(0-\tau)}$ and $C_{max}$

| Cohort | Intra-subject CV % of $AUC_{(0-\tau)}$ | Intra-subject CV % of $C_{max}$ |
|---|---|---|
| 25 mg QD | 7.0 | 10.2 |
| 50 mg QD | 8.4 | 5.7 |
| 100 mg QD | 15.7 | 23.7 |
| 200 mg QD | 14.0 | 18.3 |

TABLE 31

Geometric Mean (Geometric CV %) of Compound I Urine Pharmacokinetic Parameters

| Dose of Compound I | Day | Ae (mg) Geometric Mean (CV %) | fe (%) Geometric Mean (CV %) | $CL_R$ (mL/min) Geometric Mean (CV %) |
|---|---|---|---|---|
| 25 mg | Day 1 (n = 8) | 1.3 (40.9) | 5.2 (40.86) | 9.5 (32.4) |
|  | Day 14 (n = 8) | 3.5 (35.6) | 14.0 (35.6) | 13.3 (37.5) |
| 50 mg | Day 1 (n = 8) | 3.0 (34.8) | 5.9 (34.8) | 10.9 (36.8) |
|  | Day 14 (n = 8) | 6.9 (49.4) | 13.9 (49.4) | 11.8 (43.4) |

TABLE 31-continued

Geometric Mean (Geometric CV %) of Compound
I Urine Pharmacokinetic Parameters

| Dose of Compound I | Day | Geometric Mean (CV %) | | |
|---|---|---|---|---|
| | | Ae (mg) | fe (%) | $CL_R$ (mL/min) |
| 100 mg | Day 1 (n = 8) | 5.3 (45.9) | 5.3 (46.0) | 12.0 (40.6) |
| | Day 14 (n = 8) | 11.9 (38.7) | 11.9 (38.7) | 15.4 (27.1) |
| 200 mg | Day 1 (n = 8) | 5.0 (54.4) | 2.5 (54.5) | 5.5 (43.3) |
| | Day 14 (n = 8) | 11.7 (53.1) | 5.8 (53.1) | 8.5 (46.9) |

Ae = amount of drug excreted in urine; fe = percentage of dose excreted in urine. $CL_R$ = renal clearance of drug.

TABLE 32

S-cis isomer of Compound I Plasma Pharmacokinetic Parameters (Geometric Mean (Geometric CV %)) on Day 14 Following Once Daily Dosing (N = 8)

| Treatment | $C_{max}$ (ng/mL) | $C_{trough}$ (ng/mL) | $t_{max}$[a] (hr) | $AUC_{(0-\tau)}$[b] (ng·hr/mL) | $AUC_{(0-\infty)}$ (ng·hr/mL) | $t_{1/2}$ hr | RA |
|---|---|---|---|---|---|---|---|
| 25 mg | 5.43 (41.99) | 2.33 (37.73) | 2.5 (2.0-10.0) | 78.40 (25.94) | 180.14 (69.22) | 28.82 (66.55) | 2.02 (24.64) |
| 50 mg | 11.61 (34.66) | 4.93 (34.92) | 3.0 (2.0-4.0) | 177.01 (32.62) | 365.88 (42.47) | 25.39 (37.12) | 2.28 (30.23) |
| 100 mg | 14.87 (45.81) | 7.14 (34.80) | 2.5 (2.0-3.0) | 237.26 (35.91) | 541.06 (37.46) | 28.17 (25.94) | 1.88 (26.70) |
| 200 mg | 27.69 (38.45) | 10.90 (37.77) | 2.5 (2.0-4.0) | 404.33 (31.87) | 804.07 (35.33) | 23.93 (18.46) | 1.50 (41.45) |

$AUC_{(0-\tau)}$ = area under the plasma concentration versus time curve over one dosing interval; $AUC_{(0-\infty)}$ = area under the plasma concentration-time curve from time 0 extrapolated to infinity; $C_{max}$ = observed maximal plasma concentration; $C_{trough}$ = observed plasma concentration at the end of the dosing interval (i.e. 24 hours for once daily dosing); N = total number of subjects; NA = Not Applicable; $t_{1/2}$ = terminal elimination half-life; $t_{max}$ = time to maximum concentration; RA = ratio of accumulation.
[a]Median (minimum – maximum);
[b]τ = 24 hours for once daily dosing.

Discussion: The aim of this trial was to investigate the safety, tolerability, and PK of Compound I when administered as multiple doses for 14 days in healthy volunteers.

Throughout the study, no serious or severe TEAE was reported. In addition, no TEAE-leading to early termination was reported. There was no apparent dose-related trend in the number of subjects reporting TEAE. All AEs reported were mild in severity and resolved by the end of study, except for one unrelated moderate TEAE (loss of dental cap). The data indicated that multiple-dosing of Compound I was well tolerated in healthy volunteers at doses up to 200 mg daily dose for 14 days.

Compound I plasma PK was characterized by rapid absorption, with the maximum plasma concentration occurring at a median $t_{max}$ of 1 to 2 hours (FIG. 10). Following attainment of $C_{max}$, plasma concentrations of Compound I appeared to decline in a biphasic manner (FIG. 11C). The mean terminal half-life ($t_{1/2}$) ranged from 25 to 31 hours (Table 29). There was no apparent dose-related trend in $t_{1/2}$. Steady state appeared to be reached on Day 6 based on the trough Compound I plasma concentrations, with the approximately 2 fold of accumulation on both Day 10 and Day 14 with QD dosing (FIG. 10, Table 29). At steady state, systemic exposure ($AUC_\infty$) and $C_{max}$ increased with increasing daily dose from 25 mg to 200 mg (FIG. 12, Table 29). The inter-subject variability of $AUC_{ss,(0-\tau)}$ for Compound I ranged from 10% to 26% on Day 14. The intra-subject variability of $AUC_{ss,(0-\tau)}$ was less than 20% (Table 30).

Compound I excreted unchanged in the urine was low, mean fraction excreted at steady state ranged from 6% to 14% across dose levels (Table 31), suggesting that non-renal mechanisms are major elimination route.

The systemic exposure of S-cis isomer of Compound I was low, representing only about 2% that of Compound I (Table 32). The mean values of $t_{max}$, $t_{1/2}$, and accumulation ratio for S-cis isomer of Compound I were comparable to those for Compound I.

Pharmacokinetic characteristics of multiple doses Compound I are in accord with the data obtained from the single dose study.

Conclusion: Multiple doses of Compound I were well tolerated in healthy volunteers at doses up to 200 mg QD for 14 days. Systemic exposure ($C_{max}$ and AUC) of Compound I increased with increasing doses at steady state. There was approximately 2 fold accumulation of Compound I plasma concentration at steady state with once daily dosing.

Example 6.10

An Open-Label, Randomized, Single-Dose, Four-Period Crossover Study in Healthy Male Subjects to Evaluate the Relative Bioavailability and Food Effect on Compound I Formulated Capsules Methods: This was an open-label, randomized, 4-treatment, 4-period, 4-sequence crossover study in healthy subjects to evaluate relative bioavailability and food effect on Compound I capsule formulations. The study consisted of a screening phase (Day −21 to Day −2) for subject eligibility, a baseline/admission phase (Day −1) for each period, treatment and assessment phase (Days 1 to Day 8) for each period, and a follow-up visit (Day 15±2 days from the last dose). During each period, subjects were domiciled at the study site from Day −1 through Day 2 (discharged on Day 3 after PK sampling and safety evaluations). Subjects then visited the study center on Days 4, 6, and 8 of each period for PK sampling and safety evaluations. Between periods, there was a minimum of 10 days of washout from the prior dose to the next dose (no more than 14 days).

Sixteeen (16) male subjects were be randomized to one of the following 4 treatment sequences (4 subjects per sequence) on Day 1 of Period 1:

| | Period 1 | Period 2 | Period 3 | Period 4 |
|---|---|---|---|---|
| Sequence I | A | D | B | C |
| Sequence II | B | A | C | D |
| Sequence III | C | B | D | A |
| Sequence IV | D | C | A | B |

Treatment A: a single dose of 100 mg (1 × 100-mg) Compound I-in-capsule, fasting.
Treatment B: a single dose of 100 mg (1 × 100-mg) Compound I formulated capsule (Pharmaceutical Formulation VIII, Table 11), fasting.
Treatment C: a single dose of 100 mg (4 × 25-mg) Compound I formulated capsules (Pharmaceutical Formulation VII, Table 10), fasting.
Treatment D: a single dose of 100 mg (1 × 100-mg) Compound I formulated capsule (Pharmaceutical Formulation VIII, Table 11), fed.

Subjects started fasting from the night of Day −1 for a minimum of 10 hours prior to dosing. On Day 1 of each period, subjects received their randomized treatment of Compound I at approximately 8 AM. Subjects who received Treatment D first consumed a standard high-fat breakfast prior to dosing. Subjects who received Treatment A, B and C were dosed under fasting conditions. Approximately 5 mL of blood sample was collected on days 1-8 for PK analysis. Subjects received standardized meals scheduled at approximately the same time during confinement in each period of the study.

Results: The major PK parameters are summarized in Tables 33-34.

TABLE 33

Pharmacokinetic Parameters (mean)

| Parameter | Treatment A N = 14 | Treatment B N = 13 | Treatment C N = 15 | Treatment D N = 13 |
|---|---|---|---|---|
| $T_{max}$ (hr) | 2.64 | 1.62 | 1.73 | 4.12 |
| $C_{max}$ (ng/mL) | 595.38 | 773.12 | 718.57 | 693.42 |
| $AUC_{0-t}$ (ng·hr/mL) | 15710.13 | 17555.19 | 16680.89 | 17937.89 |
| $AUC_{0-\infty}$ (ng·hr/mL) | 16188.86 | 17980.76 | 17195.09 | 18460.77 |

TABLE 33-continued

Pharmacokinetic Parameters (mean)

| Parameter | Treatment A N = 14 | Treatment B N = 13 | Treatment C N = 15 | Treatment D N = 13 |
|---|---|---|---|---|
| $t_{1/2}$ (hr) | 26.30 | 23.76 | 25.14 | 24.10 |
| CL/F (mL/hr) | 0.01 | 0.01 | 0.01 | 0.01 |
| Vz/F (mL) | 0.25 | 0.21 | 0.22 | 0.19 |

TABLE 34

Statistical Analysis and Comparison of Compound I Exposure Parameters After Oral Administration of Compound I-in-capsule and Formulated Capsules Under Fasted and Fed Conditions

| Parameter | Treatment[a] | N | Geometric Mean | Comparison (Test vs. Reference) | Ratio (%) of Geometric Mean (Test/Reference) | 90% CI of Ratio (%) of Geometric Means | Intra-Subject CV % |
|---|---|---|---|---|---|---|---|
| $C_{max}$ | A | 14 | 489.1 | B vs. A | 135.3 | (106.9, 171.2) | 36.8 |
| | B | 13 | 661.9 | C vs. A | 138.9 | (110.2, 175.0) | |
| | C | 15 | 679.4 | C vs. B | 102.6 | (81.3, 129.6) | |
| | D | 13 | 656.2 | D vs. B | 99.1 | (78.0, 126.0) | |
| $AUC_t$ | A | 14 | 13973.5 | B vs. A | 109.4 | (98.3, 121.7) | 16.1 |
| | B | 13 | 15282.9 | C vs. A | 111.5 | (100.4, 123.9) | |
| | C | 15 | 15581.1 | C vs. B | 102.0 | (91.7, 113.3) | |
| | D | 13 | 16691.0 | D vs. B | 109.2 | (98.0, 121.7) | |
| $AUC_\infty$ | A | 14 | 14562.7 | B vs. A | 108.4 | (98.0, 119.9) | 15.3 |
| | B | 13 | 15782.5 | C vs. A | 110.5 | (100.0, 122.1) | |
| | C | 15 | 16090.8 | C vs. B | 102.0 | (92.2, 112.7) | |
| | D | 13 | 17328.5 | D vs. B | 109.8 | (99.1, 121.6) | |

Abbreviations: $AUC_\infty$ = area under the plasma concentration versus time curve from time zero to infinity; $AUC_t$ = area under the plasma concentration versus time curve from time 0 to the last quantifiable concentration; CI = confidence interval; $C_{max}$ = maximum plasma concentration.
[a]Treatment A: 1 × 100-mg Compound I-in-capsule, fasted; Treatment B: 1 × 100-mg Compound I formulated capsule, fasted; Treatment C: 4 × 25-mg Compound I formulated capsules, fasted; Treatment D: 1 × 100-mg Compound I formulated capsule, fed.
Conclusions: • The overall exposure, based on AUC, was similar following the treatment of the 4 × 25-mg formulated capsule, 100-mg formulated capsule, or the 100-mg Compound I-in-capsule. The formulations produced about 35% higher $C_{max}$ than the Compound I-in-capsule. • Median $t_{max}$ was 1.5 hours for the formulations as compared with 2.5 hours for the Compound I-in-capsule, which suggests that absorption rate is slightly faster with formulation. No apparent food effect on the extent of absorption following oral administration of 100-mg capsule formulation was seen. However, median $t_{max}$ was delayed by about 2.5 hours in the presence of food.

Example 6.11

Single Crystal X-Ray Structure of Compound I

Compound I (~5 mg) was suspended in ethyl acetate (500 μl) and heated to 50° C. until completely dissolved. The solvent was then allowed to slowly evaporate at room temperature to produce crystals suitable for single crystal diffraction. A crystal of sufficient size and quality for analysis by single crystal X-ray diffraction was selected directly from the sample, which exhibited a prism morphology of approximate dimensions 0.12×0.08×0.06 mm. Optical micrographs of the crystal used for data collection are shown in FIG. 1.

The compound of the crystal has been identified as the imino tautomer of Compound I, where the double bond of the imidazole moiety is exo-cyclic.

The asymmetric unit contains three independent molecules of Compound I, henceforth referred to as molecule A, (FIG. 2A), molecule B, (FIG. 2B) and molecule C, (FIG. 2C). Final $R_1[I>2\sigma(I)]=3.05\%$.

The absolute stereochemistry of Compound I has been determined. For the structure as presented with the chiral centre C18, (A, B and C), in the S configuration, the Flack parameter=0.00(7). For the inverted structure with C18, (A, B and C), in the R configuration the Flack parameter=1.00(7). On the basis of the former result, the absolute stereochemistry of Compound I has been assigned as having S configuration at the C18, (A, B and C) chiral center.

A calculated least-squares plane through the 6 atoms of the 2,4,6-trifluorophenyl ring of molecules A, B, C, (C1 to C6), gave an RMSD's from planarity of 0.0090, 0.0052 and 0.0041 respectively with atoms C6A, C1B and C2C showing the greatest deviations from planarity, −0.013(1) Å, −0.007(1) Å, and −0.006(1) Å, respectively.

A calculated least-squares plane through the 9 atoms of the purine ring of molecules A, B, C, (C7 to C11, N2 to N5), gave an RMSD's from planarity of 0.0206, 0.0275 and 0.0303 respectively with atoms C9A, C7B and C11C showing the greatest deviations from planarity, −0.032(1) Å, −0.049(1) Å, and −0.046(2) Å, respectively.

The calculated dihedral angle made between the least-squares plane of the purine and trifluorophenyl rings is 57.94 (6)°, 47.05(6)° and 48.95(6)° for molecules A, B and C, respectively.

Conformational analysis on the substituted tetrahydrofuran ring reveals that the closest ring puckering descriptor for this moiety is an envelope on O2 for molecules A and B and twisted on bond C20-O2 for molecule C.

Conformational analysis on the substituted cyclohexanol ring reveals that the closest ring puckering descriptor for this moiety is a chair form for molecules A B and C with both the amino and hydroxyl substituent occupying an equatorial position.

There are no other unusual structural features, and the final Fourier difference map is featureless, showing maximal and minimal electron densities of 0.162 and −0.229 eÅ$^{-3}$, respectively.

The experimental and simulated XRPD patterns for Compound I are presented in FIG. 3 (overlay), FIG. 4 (experimental) and FIG. 5 (simulated). 2θ peak listings against intensity for the experimental and simulated XRPD patterns for Compound I are shown in Tables 35 and 36, respectively. The two patterns match well, though it should be noted that there are small temperature shifts in some of the peaks owing to the fact that the experimental pattern was collected at room temperature and the calculated pattern is derived from data collected at 100K. The experimental pattern also shows some preferred orientation effects at low angle. Peak positions can vary from sample to sample by approximately ±0.1 degrees N. Variation in peak position may depend upon multiple factors, including particle size, sample preparation, data collection temperature and parameters. Variation in peak intensity may occur, e.g., as a result of preferred orientation and/or variation in crystal habit.

TABLE 35

XRPD Peak Listings Compound I - Experimental

| Angle °2θ | Intensity % |
|---|---|
| 10.0 | 18.6 |
| 11.9 | 4.8 |
| 12.3 | 48.2 |
| 12.8 | 21.7 |
| 15.2 | 22.9 |
| 16.0 | 64.8 |
| 16.2 | 14.0 |
| 16.7 | 5.9 |
| 17.7 | 29.5 |
| 18.5 | 100.0 |
| 18.9 | 34.9 |
| 19.4 | 25.3 |
| 20.0 | 19.7 |
| 20.6 | 36.7 |

TABLE 35-continued

XRPD Peak Listings Compound I - Experimental

| Angle °2θ | Intensity % |
|---|---|
| 20.8 | 20.8 |
| 21.6 | 13.3 |
| 22.7 | 12.6 |
| 23.1 | 34.6 |
| 24.1 | 34.7 |
| 24.4 | 20.9 |
| 24.6 | 13.5 |
| 24.8 | 15.3 |
| 25.7 | 19.7 |
| 25.9 | 20.3 |
| 26.1 | 17.2 |
| 26.3 | 20.9 |
| 27.1 | 14.4 |
| 27.4 | 11.3 |
| 27.8 | 13.6 |

TABLE 36

XRPD Peak Listings Compound I - Simulated

| Angle °2θ | Intensity % |
|---|---|
| 5.4 | 4.3 |
| 10.1 | 12.7 |
| 10.4 | 1.5 |
| 12.0 | 2.2 |
| 12.4 | 40.5 |
| 12.9 | 13.8 |
| 15.3 | 14.6 |
| 16.1 | 50.7 |
| 16.4 | 17.5 |
| 16.8 | 5.1 |
| 17.8 | 16.6 |
| 18.6 | 100.0 |
| 19.0 | 30.0 |
| 19.6 | 17.0 |
| 21.8 | 7.5 |
| 22.9 | 11.8 |
| 23.4 | 35.0 |
| 24.3 | 31.1 |
| 24.6 | 14.6 |
| 24.7 | 9.6 |
| 25.0 | 11.6 |
| 26.0 | 14.8 |
| 26.2 | 17.0 |
| 26.3 | 17.3 |
| 26.6 | 20.4 |
| 26.7 | 15.1 |
| 27.4 | 13.8 |
| 27.6 | 9.3 |

TABLE 37

Sample and Crystal Data for Compound I

| | |
|---|---|
| Empirical formula | $C_{21}H_{23}N_6O_2F_3$ |
| Formula weight | 448.45 |
| Temperature | 100(1) K |
| Wavelength | 1.5418 Å |
| Crystal size | 0.12 × 0.08 × 0.06 mm |
| Crystal habit | Colourless Prism |
| Crystal system | Orthorhombic |
| Space group | $P2_12_12_1$ |
| Unit cell dimensions | a = 9.9354(3) Å    α = 90° |
| | b = 18.6610(5) Å    β = 90° |
| | c = 32.9747(8) Å    γ = 90° |
| Volume | 6113.7(3) Å$^3$ |
| Z | 12 |
| Density (calculated) | 1.462 Mg/m$^3$ |

TABLE 37-continued

Sample and Crystal Data for Compound I

| | |
|---|---|
| Absorption coefficient | 0.990 mm$^{-1}$ |
| F(000) | 2808 |

TABLE 38

Data Collection and Structure Refinement

| | |
|---|---|
| Diffractometer | SuperNova, Dual, Cu at zero, Atlas |
| Radiation source | SuperNova (Cu) X-ray Source, CuKα |
| Data collection method | omega scans |
| Theta range for data collection | 3.58 to 62.24° |
| Index ranges | −11 ≤ h ≤ 10, −21 ≤ k ≤ 17, −28 ≤ l ≤ 37 |
| Reflections collected | 20039 |
| Independent reflections | 9449 [R(int) = 0.0261] |
| Coverage of independent reflections | 98.8% |
| Variation in check reflections | N/A |
| Absorption correction | Semi-empirical from equivalents |
| Max. and min. transmission | 1.00000 and 0.83924 |
| Structure solution technique | direct |
| Structure solution program | Bruker SHELXTL |
| Refinement technique | Full-matrix least-squares on F$^2$ |
| Refinement program | Bruker SHELXTL |
| Function minimized | $\Sigma w(F_o^2 - F_c^2)^2$ |
| Data/restraints/parameters | 9449/0/901 |
| Goodness-of-fit on F$^2$ | 1.003 |
| Δ/σ$_{max}$ | 0.002 |
| Final R indices | |
| 8667 data; I > 2σ(I) | R1 = 0.0305, wR2 = 0.0746 |
| all data | R1 = 0.0357, wR2 = 0.0780 |
| Weighting scheme | w = 1/[σ$^2$ (F$_o^2$) + (0.0490P)$^2$ + 0.9400P] where P = (F$_o^2$ + 2F$_c^2$)/3 |
| Absolute structure parameter | 0.00(7) |
| Largest diff. peak and hole | 0.162 and −0.229 eÅ$^{-3}$ |

TABLE 39

Atomic Coordinates and Equivalent Isotropic Atomic Displacement Parameters, (Å$^2$)

| | x/a | y/b | z/c | U(eq) |
|---|---|---|---|---|
| Molecule A | | | | |
| F1A | 1.09549(12) | 0.35377(6) | 0.88041(3) | 0.0249(3) |
| F2A | 1.38781(13) | 0.17383(7) | 0.92476(4) | 0.0357(3) |
| F3A | 1.08661(13) | 0.27893(7) | 1.01666(3) | 0.0303(3) |
| O1A | 0.07332(15) | 0.67476(7) | 0.95197(4) | 0.0219(3) |
| O2A | 0.65123(16) | 0.53089(7) | 1.02448(4) | 0.0262(3) |
| N1A | 0.98171(17) | 0.36898(8) | 0.95886(5) | 0.0175(4) |
| N2A | 0.77335(16) | 0.42190(8) | 0.94275(5) | 0.0171(4) |
| N3A | 0.82634(16) | 0.32208(9) | 0.90911(5) | 0.0165(4) |
| N4A | 0.49812(16) | 0.35951(8) | 0.85993(5) | 0.0165(4) |
| N5A | 0.55953(16) | 0.44692(8) | 0.91063(5) | 0.0170(4) |
| N6A | 0.36749(17) | 0.45912(9) | 0.87118(5) | 0.0197(4) |
| C1A | 1.1402(2) | 0.31148(10) | 0.91092(6) | 0.0182(4) |
| C2A | 1.2431(2) | 0.26423(11) | 0.90196(6) | 0.0223(5) |
| C3A | 1.2892(2) | 0.22220(11) | 0.93304(6) | 0.0233(5) |
| C4A | 1.2402(2) | 0.22646(11) | 0.97187(7) | 0.0251(5) |
| C5A | 1.1373(2) | 0.27435(11) | 0.97875(6) | 0.0203(4) |
| C6A | 1.08106(19) | 0.31822(10) | 0.94897(6) | 0.0158(4) |
| C7A | 0.8729(2) | 0.36914(10) | 0.93770(5) | 0.0157(4) |
| C8A | 0.67010(19) | 0.40822(10) | 0.91622(6) | 0.0150(4) |
| C9A | 0.4785(2) | 0.42002(10) | 0.88117(6) | 0.0167(4) |
| C10A | 0.61107(19) | 0.32113(10) | 0.86742(5) | 0.0163(4) |
| C11A | 0.7012(2) | 0.34518(10) | 0.89534(5) | 0.0156(4) |
| C12A | 0.3205(2) | 0.52037(10) | 0.89454(6) | 0.0176(4) |
| C13A | 0.2464(2) | 0.49735(10) | 0.93245(6) | 0.0226(5) |
| C14A | 0.1955(2) | 0.56187(10) | 0.95628(6) | 0.0219(5) |
| C15A | 0.1089(2) | 0.61046(10) | 0.93050(6) | 0.0186(4) |
| C16A | 0.1803(2) | 0.63215(10) | 0.89203(6) | 0.0212(5) |
| C17A | 0.2292(2) | 0.56664(11) | 0.86812(6) | 0.0208(4) |
| C18A | 0.7851(2) | 0.47837(10) | 0.97345(6) | 0.0201(4) |
| C19A | 0.6949(3) | 0.46310(11) | 1.01047(6) | 0.0295(5) |
| C20A | 0.6219(2) | 0.57029(11) | 0.98831(6) | 0.0218(5) |
| C21A | 0.7380(2) | 0.55371(11) | 0.95974(6) | 0.0202(4) |
| Molecule B | | | | |
| F1B | 1.56944(11) | 1.15917(6) | 0.79328(3) | 0.0199(3) |
| F2B | 1.91408(12) | 1.30876(6) | 0.74704(4) | 0.0317(3) |
| F3B | 1.59788(12) | 1.21904(6) | 0.65462(3) | 0.0246(3) |
| O1B | 0.58933(14) | 0.81098(7) | 0.71467(4) | 0.0189(3) |
| O2B | 1.11693(15) | 0.98817(7) | 0.64040(4) | 0.0239(3) |
| N1B | 1.46755(16) | 1.14057(9) | 0.71166(5) | 0.0170(4) |
| N2B | 1.25209(16) | 1.09215(8) | 0.72250(4) | 0.0158(4) |
| N3B | 1.31262(16) | 1.18159(9) | 0.76324(5) | 0.0150(3) |
| N4B | 0.98014(16) | 1.14120(8) | 0.80903(5) | 0.0156(4) |
| N5B | 1.03340(16) | 1.06641(8) | 0.75160(5) | 0.0158(4) |
| N6B | 0.83696(17) | 1.05176(9) | 0.78826(5) | 0.0171(4) |
| C1B | 1.62899(19) | 1.19409(10) | 0.76169(6) | 0.0154(4) |
| C2B | 1.74068(19) | 1.23459(10) | 0.77075(6) | 0.0182(4) |
| C3B | 1.80359(19) | 1.26822(11) | 0.73892(6) | 0.0204(4) |
| C4B | 1.7595(2) | 1.26320(11) | 0.69979(6) | 0.0217(5) |
| C5B | 1.64530(19) | 1.22273(10) | 0.69289(6) | 0.0175(4) |
| C6B | 1.57401(19) | 1.18589(10) | 0.72313(5) | 0.0153(4) |
| C7B | 1.3568(2) | 1.13989(10) | 0.73199(5) | 0.0148(4) |
| C8B | 1.1484(2) | 1.10274(10) | 0.74924(5) | 0.0141(4) |
| C9B | 0.95451(19) | 1.08799(10) | 0.78265(5) | 0.0140(4) |
| C10B | 1.09664(19) | 1.17787(10) | 0.80453(5) | 0.0151(4) |
| C11B | 1.18412(19) | 1.15958(10) | 0.77469(5) | 0.0164(4) |
| C12B | 0.7838(2) | 0.99797(10) | 0.76060(6) | 0.0164(4) |
| C13B | 0.8556(2) | 0.92626(10) | 0.76459(6) | 0.0187(4) |
| C14B | 0.7960(2) | 0.87168(10) | 0.73536(6) | 0.0186(4) |
| C15B | 0.6459(2) | 0.86186(10) | 0.74259(6) | 0.0173(4) |
| C16B | 0.57132(19) | 0.93273(10) | 0.74098(6) | 0.0176(4) |
| C17B | 0.63359(19) | 0.98823(10) | 0.76923(6) | 0.0192(4) |
| C18B | 1.2604(2) | 1.03957(10) | 0.68958(6) | 0.0185(4) |
| C19B | 1.1591(2) | 1.05603(11) | 0.65538(6) | 0.0245(5) |
| C20B | 1.1013(2) | 0.94490(11) | 0.67587(6) | 0.0212(5) |
| C21B | 1.2241(2) | 0.96182(10) | 0.70182(6) | 0.0211(5) |
| Molecule C | | | | |
| F1C | −0.09310(11) | 0.82865(6) | 0.95661(3) | 0.0201(3) |
| F2C | −0.43755(12) | 0.67619(6) | 0.91296(3) | 0.0263(3) |
| F3C | −0.13380(12) | 0.77063(6) | 0.81787(3) | 0.0265(3) |
| O1C | 0.88529(15) | 1.18600(7) | 0.88454(4) | 0.0224(3) |
| O2C | 0.32786(14) | 1.01173(7) | 0.80415(4) | 0.0231(3) |
| N1C | −0.00036(17) | 0.84924(8) | 0.87476(5) | 0.0181(4) |
| N2C | 0.21266(17) | 0.90023(8) | 0.88567(5) | 0.0164(4) |
| N3C | 0.16111(16) | 0.80601(8) | 0.92394(5) | 0.0156(4) |
| N4C | 0.49857(16) | 0.84534(8) | 0.96668(5) | 0.0167(4) |
| N5C | 0.43682(17) | 0.92302(8) | 0.91099(5) | 0.0167(4) |
| N6C | 0.64331(17) | 0.93138(9) | 0.94339(5) | 0.0176(4) |
| C1C | −0.15327(19) | 0.79268(10) | 0.92549(6) | 0.0164(4) |
| C2C | −0.2631(2) | 0.75089(10) | 0.93543(6) | 0.0186(4) |
| C3C | −0.3283(2) | 0.71737(10) | 0.90414(6) | 0.0190(4) |
| C4C | −0.2882(2) | 0.72334(10) | 0.86436(6) | 0.0193(4) |
| C5C | −0.1763(2) | 0.76521(10) | 0.85679(6) | 0.0189(4) |
| C6C | −0.10332(19) | 0.80218(10) | 0.88644(6) | 0.0160(4) |
| C7C | 0.1120(2) | 0.85011(10) | 0.89440(5) | 0.0172(4) |
| C8C | 0.3218(2) | 0.88710(10) | 0.91015(5) | 0.0144(4) |
| C9C | 0.5217(2) | 0.89889(10) | 0.94010(6) | 0.0163(4) |
| C10C | 0.3823(2) | 0.80847(10) | 0.96307(6) | 0.0168(4) |
| C11C | 0.29065(19) | 0.82805(10) | 0.93432(6) | 0.0155(4) |
| C12C | 0.6938(2) | 0.99069(10) | 0.91897(6) | 0.0178(4) |
| C13C | 0.6191(2) | 1.06075(10) | 0.92642(6) | 0.0186(4) |
| C14C | 0.6789(2) | 1.12046(10) | 0.90074(6) | 0.0205(4) |
| C15C | 0.8278(2) | 1.13090(10) | 0.90953(6) | 0.0200(4) |
| C16C | 0.9053(2) | 1.06127(10) | 0.90502(6) | 0.0193(4) |
| C17C | 0.84243(19) | 1.00010(11) | 0.92909(6) | 0.0206(4) |
| C18C | 0.1978(2) | 0.95725(10) | 0.85564(6) | 0.0174(4) |
| C19C | 0.2826(2) | 0.94341(11) | 0.81726(6) | 0.0243(5) |

TABLE 39-continued

Atomic Coordinates and Equivalent Isotropic
Atomic Displacement Parameters, (Å²)

|      | x/a       | y/b         | z/c        | U(eq)     |
|------|-----------|-------------|------------|-----------|
| C20C | 0.3626(2) | 1.04856(11) | 0.84084(6) | 0.0204(4) |
| C21C | 0.2462(2) | 1.03224(10) | 0.86940(6) | 0.0196(4) |

TABLE 40

Hydrogen Atom Coordinates and Isotropic
Atomic Displacement Parameters, (Å²)

|           | x/a      | y/b        | z/c       | U         |
|-----------|----------|------------|-----------|-----------|
| Molecule A |          |            |           |           |
| H1A       | 0.060(3) | 0.6649(13) | 0.9760(8) | 0.032(7)  |
| H3A       | 0.863(2) | 0.2777(13) | 0.9017(7) | 0.030(6)  |
| H6A       | 0.305(2) | 0.4331(12) | 0.8564(6) | 0.026(6)  |
| H2AA      | 1.2802   | 0.2611     | 0.8755    | 0.027     |
| H4AB      | 1.2758   | 0.1977     | 0.9931    | 0.030     |
| H10C      | 0.6273   | 0.2776     | 0.8533    | 0.020     |
| H12C      | 0.4004   | 0.5496     | 0.9027    | 0.021     |
| H13E      | 0.3075   | 0.4688     | 0.9498    | 0.027     |
| H13F      | 0.1693   | 0.4666     | 0.9248    | 0.027     |
| H14E      | 0.1426   | 0.5450     | 0.9798    | 0.026     |
| H14F      | 0.2734   | 0.5894     | 0.9667    | 0.026     |
| H15C      | 0.0245   | 0.5843     | 0.9231    | 0.022     |
| H1DB      | 0.2583   | 0.6628     | 0.8989    | 0.025     |
| H1DC      | 0.1183   | 0.6606     | 0.8749    | 0.025     |
| H17E      | 0.1508   | 0.5381     | 0.8590    | 0.025     |
| H17F      | 0.2791   | 0.5826     | 0.8438    | 0.025     |
| H18C      | 0.8809   | 0.4814     | 0.9826    | 0.024     |
| H19E      | 0.6170   | 0.4331     | 1.0026    | 0.035     |
| H19F      | 0.7464   | 0.4379     | 1.0318    | 0.035     |
| H20E      | 0.6171   | 0.6223     | 0.9940    | 0.026     |
| H20F      | 0.5353   | 0.5546     | 0.9764    | 0.026     |
| H21E      | 0.8112   | 0.5893     | 0.9627    | 0.024     |
| H21F      | 0.7075   | 0.5531     | 0.9312    | 0.024     |
| Molecule B |          |            |           |           |
| H1B       | 0.571(2) | 0.8333(13) | 0.6921(7) | 0.033(7)  |
| H3B       | 1.352(2) | 1.2229(12) | 0.7722(6) | 0.026(6)  |
| H6B       | 0.781(2) | 1.0708(10) | 0.8057(6) | 0.011(5)  |
| H2BA      | 1.7728   | 1.2391     | 0.7978    | 0.022     |
| H4BB      | 1.8053   | 1.2865     | 0.6782    | 0.026     |
| H10A      | 1.1172   | 1.2164     | 0.8223    | 0.018     |
| H12A      | 0.7947   | 1.0157     | 0.7322    | 0.020     |
| H13A      | 0.9526   | 0.9326     | 0.7587    | 0.022     |
| H13B      | 0.8468   | 0.9085     | 0.7927    | 0.022     |
| H14A      | 0.8110   | 0.8879     | 0.7071    | 0.022     |
| H14B      | 0.8423   | 0.8251     | 0.7389    | 0.022     |
| H15A      | 0.6345   | 0.8420     | 0.7705    | 0.021     |
| H16A      | 0.4762   | 0.9249     | 0.7487    | 0.021     |
| H16B      | 0.5728   | 0.9512     | 0.7128    | 0.021     |
| H17A      | 0.6213   | 0.9728     | 0.7977    | 0.023     |
| H17B      | 0.5868   | 1.0347     | 0.7657    | 0.023     |
| H18A      | 1.3536   | 1.0402     | 0.6781    | 0.022     |
| H19A      | 1.0813   | 1.0833     | 0.6660    | 0.029     |
| H19B      | 1.2024   | 1.0844     | 0.6336    | 0.029     |
| H20A      | 1.0989   | 0.8934     | 0.6687    | 0.025     |
| H20B      | 1.0173   | 0.9573     | 0.6904    | 0.025     |
| H21A      | 1.2991   | 0.9286     | 0.6958    | 0.025     |
| H21B      | 1.2022   | 0.9588     | 0.7311    | 0.025     |
| Molecule C |          |            |           |           |
| H1C       | 0.911(3) | 1.1680(13) | 0.8609(8) | 0.042(7)  |
| H3C       | 0.124(2) | 0.7616(13) | 0.9323(7) | 0.038(7)  |
| H6C       | 0.700(2) | 0.9120(12) | 0.9631(7) | 0.028(6)  |
| H2CA      | -0.2921  | 0.7456     | 0.9627    | 0.022     |
| H4CB      | -0.3352  | 0.6998     | 0.8431    | 0.023     |
| H10B      | 0.3643   | 0.7691     | 0.9805    | 0.020     |
| H12B      | 0.6853   | 0.9778     | 0.8896    | 0.021     |
| H13C      | 0.5228   | 1.0546     | 0.9196    | 0.022     |
| H13D      | 0.6255   | 1.0737     | 0.9555    | 0.022     |
| H14C      | 0.6669   | 1.1088     | 0.8717    | 0.025     |

TABLE 40-continued

Hydrogen Atom Coordinates and Isotropic
Atomic Displacement Parameters, (Å²)

|      | x/a    | y/b    | z/c    | U     |
|------|--------|--------|--------|-------|
| H14D | 0.6303 | 1.1657 | 0.9063 | 0.025 |
| H15B | 0.8363 | 1.1467 | 0.9384 | 0.024 |
| H16C | 0.9990 | 1.0687 | 0.9144 | 0.023 |
| H16D | 0.9085 | 1.0479 | 0.8760 | 0.023 |
| H17C | 0.8910 | 0.9551 | 0.9230 | 0.025 |
| H17D | 0.8522 | 1.0099 | 0.9584 | 0.025 |
| H18B | 0.1009 | 0.9606 | 0.8477 | 0.021 |
| H19C | 0.3599 | 0.9119 | 0.8236 | 0.029 |
| H19D | 0.2273 | 0.9203 | 0.7960 | 0.029 |
| H20C | 0.3707 | 1.1008 | 0.8361 | 0.024 |
| H20D | 0.4486 | 1.0304 | 0.8520 | 0.024 |
| H21C | 0.1736 | 1.0682 | 0.8665 | 0.024 |
| H21D | 0.2768 | 1.0313 | 0.8980 | 0.024 |

Example 6.12

Single Crystal X-Ray Structure of bis-Hydrate of Compound I

A small amount of Compound I was dissolved in acetone/water (50/50% v/v). The solution was slowly evaporated at room temperature. The crystals were isolated and observed by polarised light microscopy. A small crystal of plate morphology was isolated and analysed by single crystal X-ray diffraction. The approximate dimensions of the selected crystal were of 0.08×0.07×0.01 mm (80×70×10 μm), see FIG. 7.

The form has been identified as the bis-Hydrate of Compound I.

The asymmetric unit contains two independent molecules of Compound I, henceforth referred to as molecule A (FIG. 8A) and molecule B (FIG. 8B), and four molecules of water. Final $R_1[I>2\sigma(I)]=3.75\%$.

The absolute stereochemistry of Compound I has been determined. For the structure as presented with the chiral centre C18, (A and B), in the S configuration, the Flack parameter=0.13(17). For the inverted structure with C18, (A and B), in the R configuration the Flack parameter=0.81(17). On the basis of the former result, the absolute stereochemistry has been assigned as having S configuration at the C18 (A and B) chiral centre.

The single crystal structure shows that the C—N bond lengths for the imidazole moieties are 1.317 (4) Å [N3A-C7A] and 1.331 (4) Å [N3B-C7B] for molecules A and B (mean value: 1.324) respectively.

Conformational analysis on the substituted cyclohexanol ring reveals that this moiety is in a chair form for molecules A and B with both the amino and hydroxyl substituent occupying an equatorial position.

There are no other unusual structural features, and the final Fourier difference map is featureless, showing maximal and minimal electron densities of 0.223 and −0.230 eÅ$^{-3}$ respectively.

The experimental and simulated XRPD patterns for the bis-hydrate of Compound I are presented in FIG. 9. The experimental pattern was measured on the material as received. The two patterns match well, though it should be noted that there are small temperature shifts in some of the peaks owing to the fact that the experimental pattern was collected at room temperature and the calculated pattern is derived from data collected at 100K.

TABLE 41

XRPD Peak Listings bis-Hydrate of Compound I - Experimental

| Angle °2θ | Intensity % |
|---|---|
| 6.9 | 13.9 |
| 8.4 | 9.5 |
| 8.7 | 38.0 |
| 11.5 | 8.6 |
| 13.2 | 6.8 |
| 13.5 | 10.7 |
| 13.8 | 16.2 |
| 14.0 | 12.6 |
| 15.0 | 16.8 |
| 15.3 | 9.0 |
| 15.7 | 8.6 |
| 16.9 | 3.9 |
| 17.2 | 15.8 |
| 17.6 | 6.1 |
| 19.2 | 30.9 |
| 19.4 | 27.1 |
| 20.2 | 100.0 |
| 20.5 | 15.5 |
| 21.5 | 7.3 |
| 22.0 | 9.7 |
| 22.3 | 20.9 |
| 23.4 | 15.1 |
| 23.7 | 15.6 |
| 24.3 | 13.8 |
| 24.5 | 10.3 |
| 25.4 | 10.2 |
| 25.7 | 8.3 |
| 26.1 | 8.7 |
| 26.5 | 9.1 |
| 27.1 | 15.3 |
| 27.5 | 10.9 |
| 27.9 | 10.8 |
| 28.2 | 7.6 |
| 28.9 | 11.4 |

TABLE 42

XRPD Peak Listings bis-Hydrate of Compound I - Simulated

| Angle °2-θ | Intensity % |
|---|---|
| 6.9 | 18.5 |
| 8.6 | 13.2 |
| 8.7 | 44.4 |
| 11.6 | 9.1 |
| 12.9 | 1.5 |
| 13.2 | 6.2 |
| 13.6 | 13.3 |
| 13.8 | 6.6 |
| 14.0 | 12.9 |
| 14.1 | 10.0 |
| 15.2 | 14.4 |
| 15.4 | 9.4 |
| 15.9 | 7.3 |
| 17.0 | 3.4 |
| 17.3 | 15.3 |
| 17.7 | 6.1 |
| 19.3 | 20.0 |
| 19.4 | 24.0 |
| 19.7 | 27.1 |
| 20.5 | 100.0 |
| 20.9 | 14.0 |
| 21.9 | 5.1 |
| 22.2 | 10.5 |
| 22.4 | 26.3 |
| 23.2 | 7.1 |
| 23.7 | 13.1 |
| 23.8 | 9.9 |
| 24.1 | 11.7 |
| 24.5 | 19.9 |
| 24.8 | 4.4 |
| 25.1 | 3.3 |
| 25.9 | 14.6 |
| 26.2 | 7.9 |
| 26.5 | 4.1 |
| 26.6 | 3.7 |
| 26.8 | 6.0 |
| 27.4 | 13.0 |
| 27.7 | 5.4 |
| 27.8 | 8.4 |
| 28.2 | 5.7 |
| 28.4 | 7.5 |
| 29.2 | 11.3 |

TABLE 43

Sample and crystal data for bis-Hydrate of Compound I

| | |
|---|---|
| Empirical formula | $C_{21}H_{23}F_3N_6O_2, 2(H_2O)$ |
| Formula weight | 484.49 |
| Temperature | 100(1) K |
| Wavelength | 1.5418 Å |
| Crystal size | 0.08 × 0.07 × 0.01 mm |
| Crystal habit | Colourless Plate |
| Crystal system | Monoclinic |
| Space group | $P2_1$ |
| Unit cell dimensions | a = 11.1219(3) Å   α = 90° |
| | b = 8.0104(2) Å   β = 91.610(2)° |
| | c = 25.5814(5) Å   γ = 90° |
| Volume | 2278.17(9) Å$^3$ |
| Z | 4 |
| Density (calculated) | 1.413 Mg/m$^3$ |
| Absorption coefficient | 0.993 mm$^{-1}$ |
| F(000) | 1016 |

TABLE 44

Data Collection and Structure Refinement

| | |
|---|---|
| Diffractometer | SuperNova, Dual, Cu at zero, Atlas |
| Radiation source | SuperNova (Cu) X-ray Source, CuKα |
| Data collection method | omega scans |
| Theta range for data collection | 8.88 to 74.50° |
| Index ranges | −13 ≤ h ≤ 13, −10 ≤ k ≤ 9, −31 ≤ l ≤ 31 |
| Reflections collected | 48161 |
| Independent reflections | 9119 [R(int) = 0.0533] |
| Coverage of independent reflections | 99.4% |
| Variation in check reflections | N/A |
| Absorption correction | Semi-empirical from equivalents |
| Max. and min. transmission | 1.00000 and 0.80978 |
| Structure solution technique | direct |
| Structure solution program | Bruker SHELXTL |
| Refinement technique | Full-matrix least-squares on $F^2$ |
| Refinement program | Bruker SHELXTL |
| Function minimized | $\Sigma w(F_o^2 - F_c^2)^2$ |
| Data/restraints/parameters | 9119/1/660 |
| Goodness-of-fit on $F^2$ | 1.030 |
| $\Delta/\sigma_{max}$ | 0.001 |
| Final R indices | |
| 7404 data; I > 2σ(I) | R1 = 0.0375, wR2 = 0.0865 |
| all data | R1 = 0.0522, wR2 = 0.0956 |
| Weighting scheme | calc w = 1/[$\sigma^2$(Fo$^2$) + (0.0437P)$^2$ + 0.5115P] where P = (Fo$^2$ + 2Fc$^2$)/3 |
| Absolute structure parameter | 0.13(17) |
| Largest diff. peak and hole | 0.223 and −0.230 eÅ$^{-3}$ |

TABLE 45

Atomic Coordinates and Equivalent Isotropic Atomic Displacement Parameters, (Å$^2$) - U(eq) is defined as one third of the trace of the orthogonalized U$_{ij}$ tensor.

| | x/a | y/b | z/c | U(eq) |
|---|---|---|---|---|
| O3W | 0.93684(19) | 0.0100(4) | 0.97204(8) | 0.0279(5) |
| O4W | 0.43584(19) | 0.8719(4) | 0.47144(8) | 0.0265(5) |
| O5W | 0.18106(19) | 0.9861(4) | 0.53593(8) | 0.0245(5) |
| O6W | 0.32042(18) | 0.3998(4) | 0.96477(8) | 0.0241(5) |
| Molecule A | | | | |
| F1A | 0.55820(16) | 0.6954(3) | −0.05656(7) | 0.0272(5) |
| F2A | 0.21051(15) | 0.9176(3) | 0.01535(6) | 0.0310(5) |
| F3A | 0.23296(18) | 0.8522(3) | −0.16609(6) | 0.0383(5) |
| O1A | 0.69156(18) | 0.8923(3) | 0.19703(7) | 0.0404(5) |
| O2A | 0.58255(19) | 0.6132(3) | 0.44781(8) | 0.0215(5) |
| N1A | 0.4416(2) | 0.7971(4) | 0.03205(9) | 0.0196(6) |
| N2A | 0.4499(2) | 0.7035(4) | 0.11997(8) | 0.0165(5) |
| N3A | 0.3169(2) | 0.5769(4) | 0.06353(9) | 0.0183(6) |
| N4A | 0.4187(2) | 0.5362(4) | 0.19726(9) | 0.0170(5) |
| N5A | 0.2685(2) | 0.3203(4) | 0.18311(9) | 0.0205(6) |
| N6A | 0.3716(2) | 0.3508(4) | 0.26215(9) | 0.0232(6) |
| C1A | 0.3866(3) | 0.8058(4) | −0.01804(11) | 0.0184(7) |
| C2A | 0.2716(3) | 0.8683(5) | −0.02680(11) | 0.0211(7) |
| C3A | 0.2170(3) | 0.8820(5) | −0.07558(11) | 0.0271(7) |
| C4A | 0.2835(3) | 0.8378(5) | −0.11770(11) | 0.0266(8) |
| C5A | 0.3992(3) | 0.7775(5) | −0.11284(12) | 0.0245(7) |
| C6A | 0.4472(3) | 0.7607(4) | −0.06283(11) | 0.0191(6) |
| C7A | 0.3998(2) | 0.6932(4) | 0.06968(11) | 0.0168(6) |
| C8A | 0.3955(3) | 0.5777(4) | 0.14784(10) | 0.0157(6) |
| C9A | 0.3128(2) | 0.5023(5) | 0.11316(10) | 0.0162(6) |
| C10A | 0.2495(3) | 0.3700(5) | 0.13355(10) | 0.0200(6) |
| C11A | 0.3518(2) | 0.4050(4) | 0.21269(10) | 0.0171(6) |
| C12A | 0.4554(3) | 0.4296(4) | 0.29884(10) | 0.0183(6) |
| C13A | 0.4761(3) | 0.3112(5) | 0.34478(12) | 0.0259(8) |
| C14A | 0.5582(3) | 0.3859(5) | 0.38736(11) | 0.0240(7) |
| C15A | 0.5068(3) | 0.5503(4) | 0.40567(11) | 0.0194(7) |
| C16A | 0.4943(3) | 0.6722(4) | 0.36008(11) | 0.0203(7) |
| C17A | 0.4087(3) | 0.5976(5) | 0.31830(11) | 0.0205(7) |
| C18A | 0.5296(3) | 0.8324(5) | 0.14171(11) | 0.0212(7) |
| C19A | 0.4783(3) | 0.9258(5) | 0.18868(11) | 0.0282(7) |
| C20A | 0.5889(3) | 0.9490(5) | 0.22506(11) | 0.0436(9) |
| C21A | 0.6485(3) | 0.7643(5) | 0.16337(12) | 0.0276(7) |
| Molecule B | | | | |
| F1B | 1.05538(16) | 0.1901(3) | 0.44127(7) | 0.0274(5) |
| F2B | 0.71239(16) | −0.0409(3) | 0.51571(7) | 0.0338(5) |
| F3B | 0.72750(18) | 0.0249(3) | 0.33400(6) | 0.0384(5) |
| O1B | 1.05513(19) | −0.1313(3) | 0.71224(7) | 0.0382(5) |
| O2B | 1.08661(18) | 0.2679(3) | 0.94658(8) | 0.0212(5) |
| N1B | 0.9422(2) | 0.0870(4) | 0.53079(9) | 0.0203(6) |
| N2B | 0.9468(2) | 0.1772(4) | 0.61921(9) | 0.0179(6) |
| N3B | 0.8166(2) | 0.3068(4) | 0.56247(9) | 0.0183(6) |
| N4B | 0.9126(2) | 0.3408(4) | 0.69665(9) | 0.0183(6) |
| N5B | 0.7633(2) | 0.5574(4) | 0.68262(9) | 0.0197(6) |
| N6B | 0.8621(2) | 0.5217(4) | 0.76251(9) | 0.0218(6) |
| C1B | 0.8863(3) | 0.0761(4) | 0.48059(11) | 0.0187(7) |
| C2B | 0.7717(3) | 0.0098(5) | 0.47328(12) | 0.0236(7) |
| C3B | 0.7150(3) | −0.0068(5) | 0.42469(11) | 0.0256(7) |
| C4B | 0.7805(3) | 0.0411(5) | 0.38235(11) | 0.0259(8) |
| C5B | 0.8948(3) | 0.1042(5) | 0.38592(11) | 0.0243(7) |
| C6B | 0.9443(3) | 0.1222(4) | 0.43570(11) | 0.0198(7) |
| C7B | 0.8998(3) | 0.1883(4) | 0.56851(11) | 0.0167(6) |
| C8B | 0.8924(3) | 0.3015(4) | 0.64683(11) | 0.0170(6) |
| C9B | 0.8108(2) | 0.3800(5) | 0.61232(10) | 0.0176(6) |
| C10B | 0.7467(2) | 0.5094(5) | 0.63245(10) | 0.0198(6) |
| C11B | 0.8459(3) | 0.4711(4) | 0.71241(10) | 0.0180(7) |
| C12B | 0.9506(3) | 0.4440(4) | 0.79838(10) | 0.0185(7) |
| C13B | 0.9065(3) | 0.2764(5) | 0.81869(11) | 0.0207(7) |
| C14B | 0.9946(3) | 0.2052(4) | 0.85996(11) | 0.0183(7) |
| C15B | 1.0085(3) | 0.3296(5) | 0.90452(10) | 0.0187(7) |
| C16B | 1.0595(3) | 0.4928(5) | 0.88544(11) | 0.0202(7) |
| C17B | 0.9747(3) | 0.5664(5) | 0.84330(11) | 0.0233(8) |
| C18B | 1.0235(2) | 0.0451(4) | 0.64125(11) | 0.0178(7) |
| C19B | 1.1375(3) | 0.1082(5) | 0.67104(11) | 0.0262(7) |
| C20B | 1.1417(3) | 0.0007(5) | 0.71997(12) | 0.0471(8) |
| C21B | 0.9600(3) | −0.0587(5) | 0.68266(11) | 0.0263(7) |

TABLE 46

Hydrogen Atom Coordinates and Isotropic Atomic Displacement Parameters, (Å$^2$)

| | x/a | y/b | z/c | U |
|---|---|---|---|---|
| H3WA | 0.865(3) | 0.062(5) | 0.9692(13) | 0.042 |
| H3WB | 0.936(3) | −0.044(5) | 1.0007(14) | 0.042 |
| H4WA | 0.428(3) | 0.961(5) | 0.4943(14) | 0.040 |
| H4WB | 0.357(3) | 0.858(5) | 0.4652(12) | 0.040 |
| H5WA | 0.246(3) | 1.053(5) | 0.5407(13) | 0.037 |
| H5WB | 0.185(3) | 0.945(5) | 0.5073(14) | 0.037 |
| H6WA | 0.308(3) | 0.455(5) | 0.9942(14) | 0.036 |
| H6WB | 0.253(3) | 0.358(5) | 0.9612(13) | 0.036 |
| Molecule A | | | | |
| H$_2$OA | 0.549(4) | 0.694(8) | 0.460(2) | 0.078(14) |
| H1NA | 0.517(3) | 0.845(5) | 0.0366(13) | 0.042(11) |
| H6NA | 0.329(2) | 0.278(4) | 0.2736(10) | 0.009(7) |
| H3A | 0.1365 | 0.9205 | −0.0799 | 0.033 |
| H5A | 0.4440 | 0.7488 | −0.1426 | 0.029 |
| H10A | 0.1915 | 0.3135 | 0.1121 | 0.024 |
| H12A | 0.5335 | 0.4479 | 0.2813 | 0.022 |
| H13A | 0.5123 | 0.2064 | 0.3320 | 0.031 |
| H13B | 0.3976 | 0.2830 | 0.3599 | 0.031 |
| H14A | 0.5656 | 0.3075 | 0.4172 | 0.029 |
| H14B | 0.6394 | 0.4042 | 0.3735 | 0.029 |
| H15A | 0.4250 | 0.5289 | 0.4194 | 0.023 |
| H16A | 0.5741 | 0.6928 | 0.3451 | 0.024 |
| H16B | 0.4622 | 0.7800 | 0.3725 | 0.024 |
| H17A | 0.3282 | 0.5820 | 0.3331 | 0.025 |
| H17B | 0.4004 | 0.6760 | 0.2885 | 0.025 |
| H18A | 0.5466 | 0.9152 | 0.1136 | 0.025 |
| H19A | 0.4437 | 1.0348 | 0.1779 | 0.034 |
| H19B | 0.4156 | 0.8589 | 0.2057 | 0.034 |
| H20A | 0.5986 | 1.0681 | 0.2347 | 0.052 |
| H20B | 0.5802 | 0.8830 | 0.2575 | 0.052 |
| H21A | 0.6362 | 0.6592 | 0.1829 | 0.033 |
| H21B | 0.7052 | 0.7434 | 0.1350 | 0.033 |
| Molecule B | | | | |
| H$_2$OB | 1.050(3) | 0.180(5) | 0.9588(13) | 0.025 |
| H1NB | 1.024(3) | 0.073(4) | 0.5329(10) | 0.018(8) |
| H6NB | 0.821(3) | 0.623(6) | 0.7722(15) | 0.061(14) |
| H3B | 0.6355 | −0.0490 | 0.4208 | 0.031 |
| H5B | 0.9378 | 0.1339 | 0.3557 | 0.029 |
| H10B | 0.6895 | 0.5664 | 0.6107 | 0.024 |
| H12B | 1.0270 | 0.4260 | 0.7795 | 0.022 |
| H13C | 0.8977 | 0.1969 | 0.7892 | 0.025 |
| H13D | 0.8266 | 0.2910 | 0.8342 | 0.025 |
| H14C | 0.9638 | 0.0978 | 0.8733 | 0.022 |
| HMD | 1.0736 | 0.1845 | 0.8443 | 0.022 |
| H15B | 0.9273 | 0.3516 | 0.9188 | 0.022 |
| H16C | 1.1398 | 0.4737 | 0.8709 | 0.024 |
| H16D | 1.0686 | 0.5720 | 0.9150 | 0.024 |
| H17C | 0.8975 | 0.5966 | 0.8592 | 0.028 |
| H17D | 1.0107 | 0.6697 | 0.8293 | 0.028 |
| H18B | 1.0482 | −0.0305 | 0.6124 | 0.021 |
| H19C | 1.2101 | 0.0914 | 0.6502 | 0.031 |
| H19D | 1.1304 | 0.2280 | 0.6799 | 0.031 |
| H20C | 1.2232 | −0.0465 | 0.7257 | 0.057 |
| H20D | 1.1215 | 0.0684 | 0.7509 | 0.057 |
| H21D | 0.9099 | 0.0132 | 0.7048 | 0.032 |
| H21C | 0.9083 | −0.1455 | 0.6661 | 0.032 |

Example 6.13

A Phase 1, Open-Label, Single-Center Study to Evaluate the Effects of Gender, Age and Food on the Pharmacokinetics of Compound I in Healthy Subjects Methods: This was an open-label study conducted at a single study center in conformance with good clinical practice (GCP). Thirty-six eligible healthy male and female subjects were enrolled and distributed into 3 groups as follows:

Group 1—A total of 12 females between 18 to 55 years of age, inclusive (±5 years age-matched and ±10% weight-matched to subjects in Group 2).

Group 2—A total of 12 males between 18 to 55 years of age, inclusive (±5 years age-matched and ±10% weight-matched to subjects in Group 1).

Group 3—A total of 12 males and females between 65 and 85 years of age, inclusive (weight and gender-matched to subjects in Groups 1 and 2), with a minimum of 3 subjects of each gender. Seven of the subjects in Group 3 were age 70 or above, with 2 of those subjects being >75 years of age.

Group 1 (Healthy Females) and Group 3 (Elderly Males and Females): Subjects were screened within 21 days of dosing and eligible subjects were admitted to the study center on Day −1 (i.e., at least 12 hours predose) for baseline assessments and confirmation of eligibility. A single oral dose of 100 mg Compound I was administered on Day 1 following an overnight fast of at least 8 hours. Subjects were discharged from the study center the morning of Day 3 upon completion of study procedures and returned to the study center for PK blood draws and safety assessments on Days 4, 5, and 6. The end-of-study (EOS) evaluation also occurred on Day 6. Subjects returned to the study center for a follow-up visit between 7 and 10 days from EOS. Serial blood samples were collected predose and up to 120 hours postdose for the determination of plasma Compound I concentrations. Safety was monitored throughout the study; safety evaluations included AE reporting, physical examinations, vital sign measurements, ECGs, and clinical laboratory safety tests. All AEs and concomitant medications were assessed and recorded throughout the study from the time the ICF was signed through follow-up.

Group 2 (Healthy Males): Subjects in Group 2 participated in this portion of the study to evaluate food effect using a randomized, open-label, single dose, 2-period (Period 1 and Period 2), 2-sequence, 2-way crossover design. Subjects were screened within 21 days of dosing and eligible subjects were admitted to the study center on Day −1 (i.e., at least 12 hours predose) for baseline assessments and confirmation of eligibility. On Day 1 of Period 1, following an overnight fast of at least 8 hours, subjects were randomized to receive 100 mg Compound I either with or without food (6 subjects received Compound I with food and 6 subjects received Compound I without food) according to a random code. Subjects were discharged from the study center the morning of Day 3 upon completion of study procedures and returned to the study center for PK blood draws and safety assessments on Days 4, 5, and 6.

Demographics and Other Baseline Characteristics: Summary demographics for subjects participating in the evaluation of effect of food, effect of gender, and effect of age are presented in Table 47, Table 48 and Table 49, respectively. There were 19 male and 17 female subjects in this study. The mean age of the 36 subjects enrolled in this study was 52.1±15.88 years (range: 24 to 82 years). The mean height was 168.76±8.84 cm (range: 148.8 to 186.8 cm). The mean weight was 74.89±8.63 kg (range: 60.8 to 90.0 kg) and the mean BMI was 26.35±2.90 kg/m2 (range: 21.2 to 31.0 kg/m2). Twenty-eight subjects (77.8%) were White, 7 subjects (19.4%) were Black or African American, and 1 subject (2.8%) was American Indian or Alaska Native.

TABLE 47

Demographic for Analysis of Food Effect

| | MALES (Group 2) N = 12 |
|---|---|
| RACE | |
| White: | 6 |
| Black or African American: | 6 |
| AGE (year) | |
| Mean ± SD: | 42.6 ± 10.59 |
| Range: | 24-55 |
| HEIGHT (cm) | |
| Mean ± SD: | 176.55 ± 6.59 |
| Range: | 164.0-186.8 |
| WEIGHT (kg) | |
| Mean ± SD: | 74.90 ± 7.955 |
| Range: | 65.1-84.6 |
| BMI (kg/m$^2$) | |
| Mean ± SD: | 24.06 ± 2.63 |
| Range: | 21.2-30.3 |

TABLE 48

Demographic for Analysis of Gender Effect

| | MALES | | FEMALES | |
|---|---|---|---|---|
| | Young N = 12 | Elderly N = 7 | Young N = 12 | Elderly N = 5 |
| RACE: | | | | |
| White: | 6 | 7 | 10 | 5 |
| Black or African American: | 6 | 0 | 1 | 0 |
| American Indian or Alaska Native | 0 | 0 | 1 | 0 |
| AGE (year) | | | | |
| Mean ± SD: | 42.6 ± 10.59 | 71.3 ± 5.12 | 42.8 ± 9.33 | 70.2 ± 6.10 |
| Range: | 24-55 | 66-82 | 28-55 | 65-80 |
| HEIGHT (cm) | | | | |
| Mean ± SD: | 176.55 ± 6.59 | 170.80 ± 6.19 | 163.34 ± 6.21 | 160.18 ± 5.50 |
| Range | 164.0-186.8 | 160.5-178.5 | 148.8-173.5 | 154.5-166.5 |
| WEIGHT (kg) | | | | |
| Mean ± SD: | 74.90 ± 7.95 | 82.23 ± 5.94 | 74.02 ± 8.71 | 66.72 ± 6.02 |
| Range | 65.1-84.6 | 71.2-90.0 | 60.8-84.6 | 61.0-73.2 |

TABLE 48-continued

Demographic for Analysis of Gender Effect

| | MALES | | FEMALES | |
|---|---|---|---|---|
| | Young N = 12 | Elderly N = 7 | Young N = 12 | Elderly N = 5 |
| BMI (kg/m$^2$) | | | | |
| Mean ± SD: | 24.06 ± 2.63 | 28.20 ± 1.90 | 27.68 ± 2.25 | 26.04 ± 2.78 |
| Range: | 21.2-30.3 | 25.5-31.0 | 24.1-30.4 | 23.7-30.7 |

TABLE 49

Demographic for Analysis of Age Effect

| | YOUNG N = 24 | | ELDERLY N = 12 | |
|---|---|---|---|---|
| | Males N = 12 | Females N = 12 | Males N = 7 | Females N = 5 |
| RACE: | | | | |
| White: | 6 | 10 | 7 | 5 |
| Black or African American: | 6 | 1 | 0 | 0 |
| American Indian or Alaska Native | 0 | 1 | 0 | 0 |
| AGE (year) | | | | |
| Mean ± SD: | 42.6 ± 10.59 | 42.8 ± 9.33 | 71.3 ± 5.12 | 70.2 ± 6.10 |
| Range: | 24-55 | 28-55 | 66-82 | 65-80 |
| HEIGHT (cm) | | | | |
| Mean ± SD: | 176.55 ± 6.59 | 163.34 ± 6.21 | 170.80 ± 6.19 | 160.18 ± 5.50 |
| Range: | 164.0-186.8 | 148.8-173.5 | 160.5-178.5 | 154.5-166.5 |
| WEIGHT (kg) | | | | |
| Mean ± SD: | 74.90 ± 7.95 | 74.02 ± 8.71 | 82.23 ± 5.94 | 66.72 ± 6.02 |
| Range: | 65.1-84.6 | 60.8-84.6 | 71.2-90.0 | 61.0-73.2 |
| BMI (kg/m$^2$) | | | | |
| Mean ± SD: | 24.06 ± 2.63 | 27.68 ± 2.25 | 28.20 ± 1.90 | 26.04 ± 2.78 |
| Range: | 21.2-30.3 | 24.1-30.4 | 25.5-31.0 | 23.7-30.7 |

Following an interdose interval of 10 to 15 days (i.e., at least 10 days and no more than 15 days from the dosing day (Day 1) of Period 1 to Day 1 of Period 2), subjects were re-admitted to the study center on Day −1 of Period 2 (i.e., at least 12 hours predose) for baseline assessments and reconfirmation of eligibility. On Day 1 of Period 2, assigned treatment was switched. Subjects who received Compound I with food in Period 1 received Compound I without food in Period 2 and subjects who received Compound I without food in Period 1 received Compound I with food in Period 2. Subjects were discharged from the study center the morning of Day 3 upon completion of study procedures and returned to the study center for PK blood draws and safety assessments on Days 4, 5, and 6. Day 6 of Period 2 also served as the EOS evaluation. Subjects returned to the study center for a follow-up visit between 7 and 10 days from EOS. In each study period, serial blood samples were collected predose and up to 120 hours postdose for the determination of plasma Compound I concentrations. Safety was monitored throughout the study; safety evaluations included AE reporting, physical examinations, vital sign measurements, ECGs, and clinical laboratory safety tests. All AEs and concomitant medications were assessed and recorded throughout the study from the time the ICF was signed through follow-up.

The effect of age and gender on the PK of Compound I was assessed using data from all healthy subjects who were administered Compound I under fasting conditions (Group 1, Group 2 under fasting conditions, and Group 3). The effect of food on the PK of Compound I was assessed using data from the healthy male subjects in Group 2 who were administered Compound I under fasting and fed conditions in a crossover fashion.

Blood samples from subjects in Groups 1, 2 (both study periods) and 3 were collected predose (0-hr) and at 0.5, 1, 1.5, 2, 2.5, 3, 4, 8, 12, 24, 36, 48, 72, 96, and 120 hours postdose. Acceptable PK sample collection windows were provided to the site prior to study initiation. Specific instructions regarding the collection, handling, processing, storage, and shipment of PK samples were provided to the site via a separate, stand-alone PK Manual. At each time point, approximately 5 mL blood was collected into a pre-chilled $K_2$-EDTA tube. Within 30 minutes of blood collection, each sample was centrifuged at 1,500 g (3,000 rpm) for 10 minutes at 4° C. to obtain plasma. The plasma was divided into 2 aliquots and transferred into 2 polypropylene tubes (approximately 1 mL plasma per tube). Within 60 minutes of blood collection, plasma samples were transferred into a −70° C. freezer where they remained stored until they were shipped to the bioanalytical laboratory. Plasma samples were assayed for Compound I using a validated liquid chromatography and tandem mass spectroscopy (LC/MS/MS) method.

Pharmacokinetics: The following non-compartmental PK parameters were calculated from plasma concentration-time data using WinNonlin (Professional Version 5.1.1). Actual sampling times were used in the calculations:

$AUC_{0-t}$: Area under the plasma concentration-time curve from time zero to time t, where t is the last measurable time point $AUC_{0-\infty}$: Area under the plasma concentration-time curve from time zero extrapolated to infinity $C_{max}$: Maximum observed plasma concentration $T_{max}$: Time to maximum observed plasma concentration $t_{1/2}$: Estimate of the terminal elimination half-life in plasma CL/F: Apparent total plasma clearance when dosed orally Vz/F: Apparent total volume of distribution when dosed orally The PK profiles of Compound I after a 100 mg single oral dose were characterized and compared to assess the effects of food, age, and gender. In general, the PK of Compound I was similar to that observed in previous studies in healthy subjects with rapid absorption (median $T_{max}$ of 1 to 2 hours under fasting conditions; 4 hours with food) and relatively slow elimination (mean $t_{1/2}$ ranging from approximately 23 to 34 hours).

Following a single oral dose of 100 mg Compound I with or without food, the median $T_{max}$ increased from 1 hour under the fasting condition to 4 hours under the fed condition. When Compound I was given with food, the geometric mean values of $AUC_{0-\infty}$ and $C_{max}$ of Compound I were 16177.79 ng*hr/mL and 571.69 ng/mL, respectively, as compared to 15584.10 ng*hr/mL and 658.46 ng/mL, respectively, without food. When a single oral dose of 100 mg Compound I was given to young and elderly healthy subjects, the PK parameters (geometric mean) were similar in both age groups with respective $AUG_{0-\infty}$ and $C_{max}$ of Compound I being 14398.28 ng*hr/mL and 602.02 ng/mL for young subjects and 14239.14 ng*hr/mL and 648.81 ng/mL for elderly subjects. The median $T_{max}$ was approximately 1.5 hours in both groups. Following a single oral dose of 100 mg Compound I to males and females, the systemic exposures of Compound I were comparable between the two genders with respective $AUC_{0-\infty}$ and $C_{max}$ of Compound I being 14983.12 ng*hr/mL and 645.79 ng/mL for male subjects and 13663.99 ng*hr/mL and 586.80 ng/mL for female subjects. The median $T_{max}$ was 1.5 and 2.0 hours in males and females, respectively.

TABLE 50

Pharmacokinetic Parameters

| | | $AUC_{0-t}$ (ng*hr/mL) | $AUC_{0-inf}$ (ng*hr/mL) | $C_{max}$ (ng/mL) | $T_{max}$ (hr) | $T_{1/2}$ (hr) | CL/F (mL/min) | Vz/F (L) |
|---|---|---|---|---|---|---|---|---|
| Group 1 | N | 12 | 12 | 12 | 12 | 12 | 12 | 12 |
| | Mean | 13045.64 | 13783.07 | 594.36 | 2.59 | 25.78 | 129.76 | 275.30 |
| | SD | 3201.05 | 3871.12 | 222.01 | 1.90 | 9.29 | 35.91 | 91.88 |
| | SE | 924.06 | 1117.50 | 64.09 | 0.55 | 2.68 | 10.37 | 26.52 |
| | CV % | 24.5 | 28.1 | 37.4 | 73.4 | 36.0 | 27.7 | 33.4 |
| | Geometric Mean | 12680.52 | 13302.69 | 550.41 | 2.19 | 24.42 | 125.29 | 264.89 |
| | Geometric CV % | 25.6 | 28.4 | 45.3 | 60.5 | 34.9 | 28.4 | 27.7 |
| | Median | 12571.98 | 12954.65 | 639.65 | 2.00 | 26.33 | 128.72 | 241.37 |
| | Min | 7869.39 | 8296.41 | 256.90 | 1.00 | 14.67 | 80.33 | 188.44 |
| | Max | 18237.04 | 20746.86 | 1017.00 | 8.00 | 48.63 | 200.89 | 537.44 |
| Group 2 Fasting | N | 12 | 12 | 12 | 12 | 12 | 12 | 12 |
| | Mean | 14741.80 | 15993.48 | 684.25 | 1.42 | 32.99 | 110.39 | 307.70 |
| | SD | 3192.36 | 3479.60 | 178.82 | 0.56 | 8.77 | 32.33 | 87.16 |
| | SE | 921.55 | 1004.47 | 51.62 | 0.16 | 2.53 | 9.33 | 25.16 |
| | CV % | 21.7 | 21.8 | 26.1 | 39.3 | 26.6 | 29.3 | 28.3 |
| | Geometric Mean | 14376.45 | 15584.10 | 658.46 | 1.33 | 31.97 | 106.95 | 295.96 |
| | Geometric CV % | 24.8 | 25.4 | 31.3 | 38.0 | 26.5 | 25.4 | 30.3 |
| | Median | 14921.75 | 16352.16 | 704.95 | 1.00 | 31.14 | 101.97 | 305.95 |
| | Min | 7906.69 | 8397.22 | 349.00 | 1.00 | 21.25 | 81.09 | 177.33 |
| | Max | 19176.18 | 20554.44 | 924.00 | 2.50 | 49.99 | 198.48 | 452.26 |
| Group 2 Fed | N | 12 | 12 | 12 | 12 | 12 | 12 | 12 |
| | Mean | 15057.83 | 16538.73 | 582.41 | 4.00 | 34.83 | 105.71 | 314.04 |
| | SD | 2984.99 | 3391.01 | 120.23 | 1.41 | 10.84 | 27.36 | 108.88 |
| | SE | 861.69 | 978.90 | 34.71 | 0.41 | 3.13 | 7.90 | 31.43 |
| | CV % | 19.8 | 20.5 | 20.6 | 35.4 | 31.1 | 25.9 | 34.7 |
| | Geometric Mean | 14744.60 | 16177.79 | 571.69 | 3.81 | 33.59 | 103.02 | 299.51 |
| | Geometric CV % | 22.7 | 23.1 | 20.1 | 32.4 | 27.5 | 23.1 | 31.8 |
| | Median | 15540.80 | 16631.59 | 556.80 | 4.00 | 34.08 | 100.23 | 278.38 |
| | Min | 8304.73 | 9286.64 | 432.50 | 2.00 | 23.43 | 79.47 | 203.52 |
| | Max | 19837.09 | 20972.93 | 817.90 | 8.00 | 64.60 | 179.47 | 571.23 |
| Group 3 Male | N | 7 | 7 | 7 | 7 | 7 | 7 | 7 |
| | Mean | 13896.05 | 14492.26 | 678.47 | 1.93 | 23.58 | 123.50 | 235.95 |
| | SD | 3606.17 | 3892.69 | 248.88 | 1.13 | 6.91 | 37.66 | 44.43 |
| | SE | 1363.00 | 1471.30 | 94.07 | 0.43 | 2.61 | 14.23 | 16.79 |
| | CV % | 26.0 | 26.9 | 36.7 | 58.8 | 29.3 | 30.5 | 18.8 |
| | Geometric Mean | 13467.74 | 14006.29 | 624.63 | 1.70 | 22.56 | 119.00 | 232.41 |
| | Geometric CV % | 28.1 | 29.6 | 50.9 | 56.6 | 34.5 | 29.5 | 18.9 |
| | Median | 14895.20 | 15372.97 | 796.60 | 1.50 | 26.80 | 108.42 | 219.20 |
| | Min | 8829.53 | 8958.19 | 260.80 | 1.00 | 12.73 | 87.29 | 179.57 |
| | Max | 18415.05 | 19094.08 | 880.50 | 4.00 | 31.60 | 186.05 | 297.22 |
| Group 3 Female | N | 5 | 5 | 5 | 5 | 5 | 5 | 5 |
| | Mean | 14519.99 | 15166.06 | 832.02 | 2.02 | 25.84 | 119.06 | 268.64 |
| | SD | 4388.19 | 4786.99 | 473.26 | 0.83 | 6.29 | 37.85 | 121.76 |
| | SE | 1962.46 | 2140.81 | 211.65 | 0.37 | 2.81 | 16.93 | 54.45 |

TABLE 50-continued

Pharmacokinetic Parameters

| | | $AUC_{0-t}$ (ng*hr/mL) | $AUC_{0-inf}$ (ng*hr/mL) | $C_{max}$ (ng/mL) | $T_{max}$ (hr) | $T_{1/2}$ (hr) | CL/F (mL/min) | Vz/F (L) |
|---|---|---|---|---|---|---|---|---|
| | CV % | 30.2 | 31.6 | 56.9 | 41.0 | 24.3 | 31.8 | 45.3 |
| | Geometric Mean | 13981.33 | 14571.65 | 684.24 | 1.88 | 25.17 | 114.38 | 249.20 |
| | Geometric CV % | 31.9 | 32.6 | 91.3 | 46.8 | 26.7 | 32.6 | 44.2 |
| | Median | 13777.13 | 14030.00 | 932.80 | 2.00 | 29.81 | 118.79 | 203.89 |
| | Min | 9078.62 | 9470.65 | 203.90 | 1.00 | 17.51 | 75.10 | 174.19 |
| | Max | 20564.58 | 22193.62 | 1271.00 | 3.12 | 31.37 | 175.98 | 454.33 |
| Group 3 | N | 12 | 12 | 12 | 12 | 12 | 12 | 12 |
| All | Mean | 14156.03 | 14773.01 | 742.45 | 1.97 | 24.52 | 121.65 | 249.57 |
| | SD | 3768.13 | 4088.83 | 348.54 | 0.98 | 6.47 | 36.05 | 82.16 |
| | SE | 1087.77 | 1180.34 | 100.62 | 0.28 | 1.87 | 10.14 | 23.72 |
| | CV % | 26.6 | 27.7 | 46.9 | 49.6 | 26.4 | 29.6 | 32.9 |
| | Geometric Mean | 13679.40 | 14239.14 | 648.81 | 1.77 | 23.61 | 117.05 | 239.26 |
| | Geometric CV % | 28.3 | 29.4 | 64.6 | 50.4 | 30.6 | 29.4 | 29.9 |
| | Median | 14336.17 | 14701.49 | 798.70 | 1.50 | 27.06 | 113.61 | 215.02 |
| | Min | 8829.53 | 8958.19 | 209.30 | 1.00 | 12.73 | 75.10 | 174.19 |
| | Max | 20564.58 | 22193.62 | 1271.00 | 4.00 | 31.60 | 186.05 | 454.33 |
| Groups | N | 24 | 24 | 24 | 24 | 24 | 24 | 24 |
| 1 & 2 | Mean | 13893.72 | 14888.27 | 639.30 | 2.00 | 29.39 | 120.07 | 291.50 |
| Fasting | SD | 3244.25 | 3772.56 | 202.42 | 1.50 | 9.57 | 34.85 | 89.14 |
| | SE | 662.23 | 770.07 | 41.32 | 0.31 | 1.95 | 7.11 | 18.19 |
| | CV % | 23.4 | 25.3 | 31.7 | 74.6 | 32.6 | 29.0 | 30.6 |
| | Geometric Mean | 13501.88 | 14398.28 | 602.02 | 1.71 | 27.94 | 115.75 | 279.99 |
| | Geometric CV % | 25.5 | 27.6 | 39.1 | 56.8 | 33.5 | 27.6 | 29.0 |
| | Median | 13886.76 | 14568.72 | 661.75 | 1.52 | 28.63 | 114.47 | 262.90 |
| | Min | 7869.39 | 8296.41 | 256.90 | 1.00 | 14.67 | 80.33 | 177.33 |
| | Max | 19176.18 | 20746.86 | 1017.00 | 8.00 | 49.99 | 200.89 | 537.44 |
| All Males | N | 19 | 19 | 19 | 19 | 19 | 19 | 19 |
| Fasting | Mean | 14430.21 | 15440.40 | 682.12 | 1.61 | 29.52 | 115.22 | 281.27 |
| | SD | 3276.95 | 3606.06 | 200.49 | 0.83 | 9.20 | 33.96 | 81.02 |
| | SE | 751.78 | 827.29 | 46.00 | 0.19 | 2.11 | 7.79 | 18.59 |
| | CV % | 22.7 | 23.4 | 29.4 | 51.5 | 31.2 | 29.5 | 28.8 |
| | Geometric Mean | 14034.74 | 14983.12 | 645.79 | 1.45 | 28.12 | 111.24 | 270.74 |
| | Geometric CV % | 25.5 | 26.7 | 38.0 | 45.7 | 33.9 | 26.7 | 28.8 |
| | Median | 14895.20 | 15977.10 | 733.80 | 1.50 | 29.17 | 104.32 | 261.52 |
| | Min | 7906.69 | 8397.22 | 260.80 | 1.00 | 12.73 | 81.09 | 177.33 |
| | Max | 19176.18 | 20554.44 | 924.00 | 4.00 | 49.99 | 198.48 | 452.26 |
| All | N | 17 | 17 | 17 | 17 | 17 | 17 | 17 |
| Females | Mean | 13479.27 | 14189.83 | 664.26 | 2.42 | 25.80 | 126.62 | 273.34 |
| | SD | 3512.57 | 4056.27 | 319.90 | 1.65 | 8.32 | 35.64 | 97.57 |
| | SE | 851.92 | 983.79 | 77.59 | 0.40 | 2.02 | 8.64 | 23.66 |
| | CV % | 26.1 | 28.6 | 48.2 | 68.1 | 32.3 | 28.1 | 35.7 |
| | Geometric Mean | 13050.01 | 13663.99 | 586.80 | 2.09 | 24.64 | 121.97 | 260.18 |
| | Geometric CV % | 26.9 | 28.9 | 58.0 | 55.6 | 31.8 | 28.9 | 31.8 |
| | Median | 12613.73 | 13238.69 | 643.50 | 2.00 | 27.22 | 125.89 | 239.94 |
| | Min | 7869.39 | 8296.41 | 203.90 | 1.00 | 14.67 | 75.10 | 174.19 |
| | Max | 20564.58 | 22193.62 | 1271.00 | 8.00 | 48.63 | 200.89 | 537.44 |

Food Effect: Plasma PK parameters of Compound I in Group 2 (male subjects between 18 and 55 years of age), when administered with and without food, were used to evaluate the effect of food on the PK of Compound I. The effect of food on $AUC_{0-t}$, $AUG_{0-\infty}$, and $C_{max}$ was analyzed on natural log-transformed data using an analysis of variance model (ANOVA) with treatment, sequence, and period as fixed effects and subject nested within sequence as a random effect. From this ANOVA, geometric means, percent ratios of the geometric means, and 90% confidence intervals (CIs) for the ratio of geometric means were obtained. For $T_{max}$, a non-parametric analysis was used to produce a median difference between the two treatments.

Following a single oral dose of 100 mg Compound I with or without food, the median $T_{max}$ increased from 1 hour under the fasting condition to 4 hours under the fed condition, indicating that the rate of drug absorption was delayed by food. However, the systemic exposure and $t_{1/2}$ (geometric mean) of Compound I appeared to be unaffected by food intake (see Table 51).

TABLE 51

Food Effect: Geometric Mean (Geometric CV %) Plasma PK Parameters of Compound I

| Parameter | 100 mg Compound I, Fasting (N = 12) | 100 mg Compound I, Fed (N = 12) |
|---|---|---|
| $T_{max}$ (hr)[a] | 1.00 (1.00-2.50) | 4.00 (2.00-8.00) |
| $C_{max}$ (ng/mL) | 658.46 (31.3) | 571.69 (20.1) |
| $AUC_{0-t}$ (ng · hr/mL) | 14376.45 (24.8) | 14744.60 (22.7) |
| $AUC_{0-\infty}$ (ng*hr/mL) | 15584.10 (25.4) | 16177.79 (23.1) |
| $t_{1/2}$(hr) | 31.97 (26.5) | 33.59 (27.5) |

Pharmacokinetic parameters of subjects from Group 2 were included in the analysis. The results are presented in Table 52 and Table 53. The 90% CIs for the ratio (fed/fast) of geometric means were (97.3, 108.1) for $AUC_{0-t}$, (98.5, 109.4) for $AUG_{0-\infty}$, and (71.6, 105.3) for $C_{max}$. The 90% CI of the median difference between the 2 treatments (fed-fast) was (2.00, 3.00) (p-value=0.0005).

TABLE 52

Statistical Analysis of Food Effect: $C_{max}$, $AUC_{0-t}$, and $AUC_{0-\infty}$ of Compound I of Group 2

| Parameter | Treatment | N | Geometric Means | % Ratio of Geometric Means | 90% CI of Ratio of Geometric Means | Intra-subject CV % |
|---|---|---|---|---|---|---|
| $AUC_{0-t}$ (h*ng/mL) | Compound I fed | 12 | 14744.6 | 102.6 | (97.3, 108.1) | 7.1 |
| | Compound I fasting | 12 | 14376.4 | | | |
| $AUC_{0-\infty}$ (h*ng/mL) | Compound I fed | 12 | 16177.8 | 103.8 | (98.5, 109.4) | 7.1 |
| | Compound I fasting | 12 | 15584.1 | | | |
| $C_{max}$ (ng/mL) | Compound I fed | 12 | 571.7 | 86.8 | (71.6, 105.3) | 26.5 |
| | Compound I fasting | 12 | 658.5 | | | |

TABLE 53

Statistical Analysis of Food Effect: $T_{max}$ of Compound I of Group 2

| Parameter | Treatment | N | Median | Median Difference | 90% CI of Median Difference | P-value |
|---|---|---|---|---|---|---|
| $T_{max}$ (hr) | Compound I fed | 12 | 4.00 | 2.50 | (2.00, 3.00) | 0.0005 |
| | Compound I fasting | 12 | 1.50 | | | |

Age and Gender Effect: Plasma PK parameter data from Group 1, Group 2 (under fasting conditions only), and Group 3 were used to evaluate the effect of age and gender.

Results summarized in Table 54 indicate that when a single oral dose of 100 mg Compound I was given to young and elderly healthy subjects, the PK parameters were similar in both age groups.

TABLE 54

Age Effect: Geometric Mean (Geometric CV %) Plasma PK Parameters of Compound I

| Parameter | 100 mg Compound I, Young (N = 24) | 100 mg Compound I, Elderly (N = 12) |
|---|---|---|
| $T_{max}$ (hr)$^a$ | 1.52 (1.00-8.00) | 1.50 (1.00-4.00) |
| $C_{max}$ (ng/mL) | 602.02 (39.1) | 648.81 (64.6) |
| $AUC_{0-t}$ (ng*hr/mL) | 13501.88 (25.5) | 13679.40 (28.3) |
| $AUC_{0-\infty}$ (ng*hr/mL) | 14398.28 (27.6) | 14239.14 (29.4) |
| $t_{1/2}$ (hr) | 27.94 (33.5) | 23.61 (30.6) |

Pharmacokinetic parameters of subjects from Group 1, Group 2 (under fasting conditions only), and Group 3 were included in the statistical analysis. Analysis of variance (ANOVA) was performed on natural log-transformed $AUC_{0-t}$, $AUC_{0-\infty}$ and $C_{max}$. The model included age, gender, and age by gender interaction as fixed effects. The age by gender interaction was tested at a significance level of 0.05. Since the age by gender interaction was not statistically significant for $AUC_{0-t}$, $AUC_{0-\infty}$ and $C_{max}$, the comparison between elderly and young subjects was based on the main effect of age. Nonparametric methods (Hodges-Lehmann estimate and Wilcoxon rank-sum test) were used to compare $T_{max}$ between elderly and young subjects. The results are presented in Table 55 and Table 56. The 90% CIs for the ratio (elderly/young) of geometric means were (86.7, 119.1) for $AUC_{0-t}$, (84.0, 117.3) for $AUC_{0-\infty}$, and (82.0, 143.8) for $C_{max}$. The 90% CI of the median difference between the 2 age groups (elderly-young) was −0.5, 0.5 (p-value=0.7821).

TABLE 55

Statistical Analysis of Age Effect: $C_{max}$, $AUC_{0-t}$, and $AUC_{0-\infty}$, of Compound I

| Parameter | Age Group | N | Geometric Means | % Ratio of Geometric Means | 90% CI of Ratio of Geometric Means |
|---|---|---|---|---|---|
| $AUC_{0-t}$ (h*ng/mL) | Elderly | 12 | 13722.1 | 101.6 | (86.7, 119.1) |
| | Young | 24 | 13501.9 | | |
| $AUC_{0-\infty}$ (h*ng/mL) | Elderly | 12 | 14286.2 | 99.2 | (84.0, 117.3) |
| | Young | 24 | 14398.3 | | |
| $C_{max}$ (ng/mL) | Elderly | 12 | 653.8 | 108.6 | (82.0, 143.8) |
| | Young | 24 | 602.0 | | |

TABLE 56

Statistical Analysis of Age Effect: $T_{max}$ of Compound I

| Parameter | Age Group | N | Median | Median Difference | 90% CI of Median Difference | P-value |
|---|---|---|---|---|---|---|
| $T_{max}$ (hr) | Elderly | 12 | 2.00 | 0 | (−0.50, 0.50) | 0.7821 |
| | Young | 24 | 1.75 | | | |

Following a single oral dose of 100 mg Compound I to males and females, the PK parameters of Compound I were similar as shown in Table 57.

TABLE 57

Gender Effect: Geometric Mean (Geometric CV %) Plasma PK Parameters of Compound I

| Parameter | 100 mg Compound I, Males (N = 19) | 100 mg Compound I, Females (N = 17) |
|---|---|---|
| $T_{max}$ (hr)$^a$ | 1.50 (1.00-4.00) | 2.00 (1.00-8.00) |
| $C_{max}$ (ng/mL) | 645.79 (38.0) | 586.80 (58.0) |
| $AUC_{0-t}$ (ng*hr/mL) | 14034.74 (25.5) | 13050.01 (26.9) |
| $AUC_{0-\infty}$ (ng*hr/mL) | 14983.12 (26.7) | 13663.99 (28.9) |
| $t_{1/2}$ (hr) | 28.12 (33.9) | 24.64 (31.8) |

The gender effect was analyzed using the same data and the same statistical methods as in the analysis of age effect. Since the age by gender interaction was not statistically significant for $AUC_{0-t}$, $AUC_{0-\infty}$, and $C_{max}$, the comparison between male and female was based on the main effect of gender. The results are presented in Table 58 and Table 59. The 90% CIs for the ratio (female/male) of geometric means were (81.7, 112.1) for $AUC_{0-t}$, (79.7, 111.4) for $AUC_{0-\infty}$, and (72.3, 126.7) for $C_{max}$. The 90% CI of the median difference between gender (female-male) was (0.00, 1.00) (p-value=0.0207).

TABLE 58

Statistical Analysis of Gender Effect:
$C_{max}$, $AUC_{0-t}$, and $AUC_{0-\infty}$ of Compound I

| Parameter | Gender | N | Geometric Means | % Ratio of Geometric Means | 90% CI of Ratio of Geometric Means |
|---|---|---|---|---|---|
| $AUC_{0-t}$ (h*ng/mL) | Female | 17 | 13315.0 | 95.7 | (81.7, 112.1) |
|  | Male | 19 | 13914.7 |  |  |
| $AUC_{0-\infty}$ (h*ng/mL) | Female | 17 | 13922.7 | 94.2 | (79.7, 111.4) |
|  | Male | 19 | 14774.1 |  |  |
| $C_{max}$ (ng/mL) | Female | 17 | 613.7 | 95.7 | (72.3, 126.7) |
|  | Male | 19 | 643.1 |  |  |

TABLE 59

Statistical Analysis of gender Effect: $T_{max}$ of Compound I

| Parameter | Gender | N | Median | Median Difference | 90% CI of Median Difference | P-value |
|---|---|---|---|---|---|---|
| $T_{max}$ (hr) | Female | 17 | 2.06 | 0.5 | (0.00, 1.00) | 0.0207 |
|  | Male | 19 | 1.50 |  |  |  |

Overall, there was no clinically relevant effect of food, age or gender on the PK of Compound I. Compound I was well tolerated in subjects of all age groups, of each gender, and when administered under fasting and fed conditions in this study.

While the invention has been described with respect to the particular embodiments, it will be apparent to those skilled in the art that various changes and modifications may be made without departing from the spirit and scope of the invention as defined in the claims. Such modifications are also intended to fall within the scope of the appended claims. A number of references have been cited, the disclosures of which are incorporated herein by reference in their entirety.

What is claimed is:

1. A pharmaceutical formulation comprising a solid form of a compound having the structure:

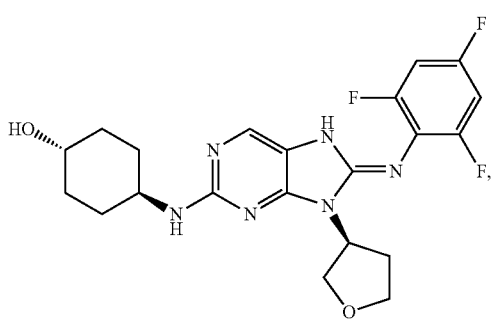 [SMILES: O[C@H]1CC[C@H](Nc2ncc3[nH]/c(=N\c4c(F)cc(F)cc4F)n([C@H]4CCOC4)c3n2)CC1]

and silicified microcrystalline cellulose.

2. The pharmaceutical formulation of claim 1, where said solid form is Form A, having an XRPD pattern comprising peaks at 12.4, 16.0 and 18.5±0.1 degrees 2θ.

3. The pharmaceutical formulation of claim 2, wherein said solid form is Form A, having an XRPD pattern further comprising peaks at 17.7, 23.2 and 24.1 degrees 2θ(±0.1).

4. The pharmaceutical formulation of claim 1, wherein the weight ratio of silicified microcrystalline cellulose over said solid form is from about 0.1 to about 10.

5. The pharmaceutical formulation of claim 4, further comprising a diluent wherein the weight ratio of the diluent over said solid form is from about 0.1 to about 1.

6. The pharmaceutical formulation of claim 5, wherein the diluent is lactose.

7. The pharmaceutical formulation of claim 6, further comprising a disintegrant wherein the weight ratio of the disintegrant over said solid form is from about 0.01 to about 0.5.

8. The pharmaceutical formulation of claim 7, wherein the disintegrant is croscarmellose sodium.

9. The pharmaceutical formulation of claim 8, further comprising a lubricant wherein the weight ratio of the lubricant over said solid form is from about 0.005 to about 0.1.

10. The pharmaceutical formulation of claim 9, wherein the lubricant is magnesium stearate.

11. The pharmaceutical formulation of claim 10, comprising 25, 100, or 200 mg of said solid form.

12. The pharmaceutical formulation of claim 1, comprising said solid form and silicified microcrystalline cellulose, lactose, croscarmellose sodium, and magnesium stearate.

13. The pharmaceutical formulation of claim 12, comprising from about 20 to about 60% by weight of said solid form by weight, and from about 25 to about 60% by weight of silicified microcrystalline cellulose, from about 5 to about 25% by weight of lactose, from about 1 to about 5% by weight of croscarmellose sodium, and from about 0.5 to about 2.5% by weight of magnesium stearate.

14. The pharmaceutical formulation of claim 1, in the form of a capsule.

15. The pharmaceutical formulation of claim 1, in the form of a coated tablet.

16. The pharmaceutical formulation of claim 1, wherein said solid form further comprises a compound having the structure:

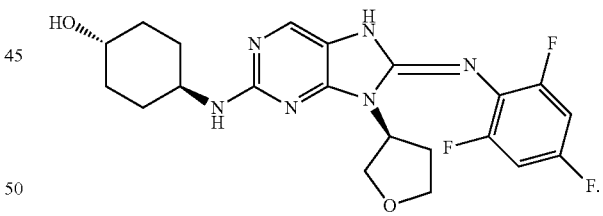

17. A method for treating a cancer, an inflammatory condition, an immunological condition, an autoimmune condition, a metabolic condition or a fibrotic condition, comprising administering to a subject having a cancer, an inflammatory condition, an immunological condition, an autoimmune condition or a metabolic condition, the pharmaceutical formulation of claim 1, wherein:

(a) the cancer is of the head, neck, eye, mouth, throat, esophagus, bronchus, larynx, pharynx, chest, bone, lung, colon, rectum, stomach, prostate, urinary bladder, uterine, cervix, breast, ovaries, testicles, skin, thyroid, blood, lymph nodes, kidney, liver, pancreas, brain or central nervous system;

(b) the inflammatory condition is asthma, allergic rhinitis, bronchitis, chronic obstructive pulmonary disease, cystic fibrosis, inflammatory bowel disease, irritable bowel syndrome, Crohn's disease, mucous colitis, ulcerative colitis, diabetes or obesity;

(c) the immunological condition is rheumatoid arthritis, rheumatoid spondylitis, osteoarthritis, multiple sclerosis, lupus, inflammatory bowel disease, ulcerative colitis, Crohn's disease, myasthenia gravis, Grave's disease or diabetes;

(d) the autoimmune condition is rheumatoid arthritis, rheumatoid spondylitis, osteoarthritis, multiple sclerosis, lupus, inflammatory bowel disease, ulcerative colitis, Crohn's disease, myasthenia gravis, Grave's disease, Type I diabetes or systemic sclerosis;

(e) the metabolic condition is obesity or diabetes; and (f) the fibrotic condition is idiopathic pulmonary fibrosis, myelofibrosis, hepatic fibrosis, renal fibrosis, chronic allograft nephropathy, glomerulonephritis, glomerular nephropathy, glomerulopathies, steatofibrosis, steatohepatitis, or scleroderma.

18. A method for preparing a pharmaceutical formulation, comprising: (i) weighing out the desired amount of a solid form of a compound having the structure:

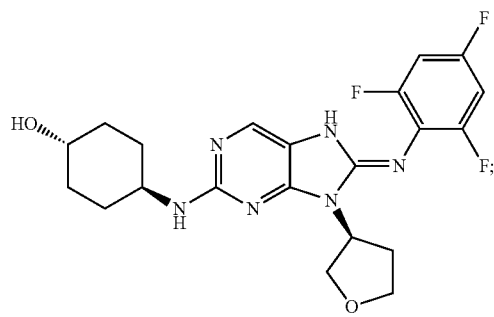 [SMILES: O[C@H]1CC[C@H](Nc2ncc3[nH]/c(=N\c4c(F)cc(F)cc4F)n([C@H]4CCOC4)c3n2)CC1]

(ii) passing said solid form through a screen;
(iii) weighing out the desired amount of the excipients; and
(iv) combining said solid form with one or more of the excipients and blending, wherein the excipients comprise a binder, a diluent, a disintegrant and a lubricant, and wherein the binder is silicified microcrystalline cellulose, the diluent is anhydrous lactose, the disintegrant is croscarmellose sodium and the lubricant is magnesium stearate.

* * * * *